(12) United States Patent
Polukhtin et al.

(10) Patent No.: US 11,639,342 B2
(45) Date of Patent: May 2, 2023

(54) 1,3-DIPOLAR CYCLOADDITIONS, AND STAUDINGER LIGATIONS FOR CONJUGATING BIOMOLECULES USING CLICK CHEMISTRY

(71) Applicant: Bioconjugate Technologies, LLC, Scottsdale, AZ (US)

(72) Inventors: Andrei Polukhtin, Scottsdale, AZ (US); Peter J. An, Scottsdale, AZ (US); Alexandra Kulyashova, Scottsdale, AZ (US); Jakub M. Labedz, Scottsdale, AZ (US); Valentin A. Rassadin, Scottsdale, AZ (US); Nikita V. Savelyev, Scottsdale, AZ (US); Kostiantyn Ziabrev, Scottsdale, AZ (US)

(73) Assignee: BIOCONJUGATE TECHNOLOGIES, LLC, Scottsdale, AZ (US)

( * ) Notice: Subject to any disclaimer, the term of this patent is extended or adjusted under 35 U.S.C. 154(b) by 415 days.

(21) Appl. No.: 16/740,153

(22) Filed: Jan. 10, 2020

(65) Prior Publication Data

US 2021/0214338 A1 Jul. 15, 2021

(51) Int. Cl.
| | | |
|---|---|---|
| *C07D 249/04* | (2006.01) |
| *C07D 403/12* | (2006.01) |
| *C07D 403/14* | (2006.01) |
| *C07D 491/147* | (2006.01) |
| *C07D 401/14* | (2006.01) |
| *C07D 405/12* | (2006.01) |
| *G01N 33/543* | (2006.01) |
| *C07D 405/14* | (2006.01) |

(52) U.S. Cl.
CPC ......... *C07D 401/14* (2013.01); *C07D 249/04* (2013.01); *C07D 403/12* (2013.01); *C07D 403/14* (2013.01); *C07D 405/12* (2013.01); *C07D 405/14* (2013.01); *C07D 491/147* (2013.01); *G01N 33/54306* (2013.01)

(58) Field of Classification Search
CPC .. C07D 249/04; C07D 403/12; C07D 403/14; C07D 491/147
See application file for complete search history.

(56) References Cited

U.S. PATENT DOCUMENTS

2015/0274701 A1* 10/2015 Taran .................. C07D 403/12
548/255

* cited by examiner

*Primary Examiner* — Brian E McDowell
(74) *Attorney, Agent, or Firm* — Birch, Stewart, Kolasch & Birch, LLP

(57) ABSTRACT

Compositions, methods, and kits for the labeling, detecting, isolating and/or analysis of biomolecules modified by attachment of chemical handles are disclosed. These embodiments involve a compound of the formula:

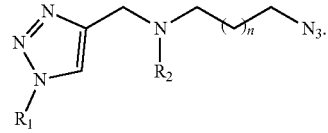

14 Claims, 1 Drawing Sheet

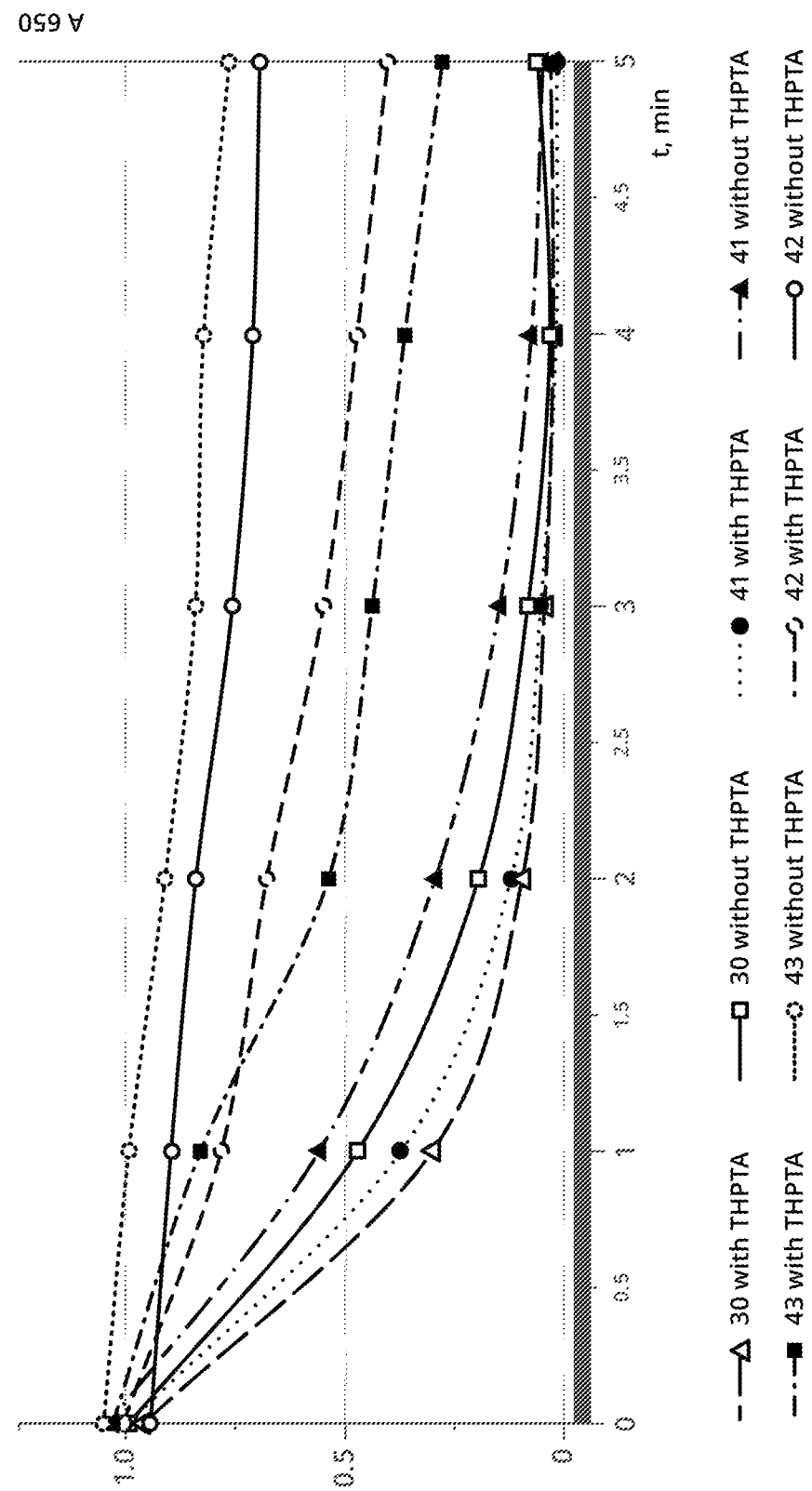

1,3-DIPOLAR CYCLOADDITIONS, AND STAUDINGER LIGATIONS FOR CONJUGATING BIOMOLECULES USING CLICK CHEMISTRY

FIELD OF THE INVENTION

This invention relates to click chemistry, 1,3-dipolar cycloadditions, and Staudinger ligations for conjugating biomolecules.

BACKGROUND

Click chemistry was developed by K. Barry Sharpless as a robust and specific method of ligating two molecules together. See, e.g., Kolb et al. Angew. Chemie Intern. 40(11): 2004-21 (2001). The copper-catalyzed azide-alkyne cycloaddition reaction, or CuAAC, has been used extensively for the conjugation, immobilization, and purification of biomolecules as well as for monitoring various biological processes. Recent advances in design of copper chelating ligands such as THTPA or BTTAA improved kinetics of copper-catalyzed azide-alkyne cycloaddition reaction and greatly increased sensitivity of alkyne detection. In spite of many recent improvements this reaction still remains slow for detection of low abundance targets and for monitoring the kinetics of biological processes that take place within the minute time scale. The next step in improving kinetics of CuAAC was introduction of copper chelating moiety into azide reports, which raises the effective concentration of Cu(I) at the reaction site. Up to date the only practically useful azides bearing an internal copper-chelating motif are electron-donating picolylazides, however these compound are not readily available and require multi-step synthesis. In addition, the kinetics of the click reaction with picolyl azide still needs to be improved.

SUMMARY OF THE INVENTION

In one aspect, the invention provides a compound of the formula:

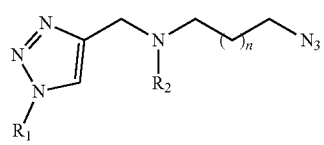

(I)

wherein:
n=0, 1, 2, 3 or 4
$R_1$, and $R_2$, are independently selected from a hydrogen, carboxylic acid, a salt of carboxylic acid, amino, alkyl, heteroalkyl, cycloalkyl, heterocycloalkyl, substituted alkyl, substituted heteroalkyl, substituted cycloalkyl, substituted heterocycloalkyl, aryl, heteroaryl, substituted aryl, arylalkyl, substituted arylalkyl, and substituted heteroaryl, arylcarboxamido,
at least one substituent selected from $R_1$, and $R_2$ comprises X-L-, wherein:
X is selected from a reporter molecule, a carrier molecule, a solid phase, a therapeutic molecule such as peptide, a protein, an antibody, a polysaccharide, a nucleic acid polymer, an ion complexing moiety, a lipid or a non-biological organic polymer or polymeric micro or nano particle, that are optionally bound to one or more additional fluorophores; or
X is a reactive group such as carboxylic acid, an activated ester of carboxylic acid, an amine, a hydrazine, a haloacetamide, an alkyl halide, an isothiocynate or a maleimide group; and
L is an independently a single covalent bond or L is covalent linkage having 1-24 non-hydrogen atoms selected from the group consisting of C, N, O, P and S and composed of any combinations of single, double, triple or aromatic carbon-carbon bonds, carbon-nitrogen bonds, nitrogen-nitrogen bonds, carbon-oxygen bonds, carbon-sulfur bonds, phosphorus-oxygen bonds and phosphorus-nitrogen bonds in the form of alkyl, heteroalkyl, cycloalkyl, heterocycloalkyl, alkoxy, substituted alkoxy, substituted alkyl, substituted heteroalkyl, substituted cycloalkyl, substituted heterocycloalkyl, aryl, heteroaryl, substituted aryl, arylalkyl, substituted arylalkyl, and substituted heteroaryl;

In yet another aspect, the invention provides compounds of the formula:

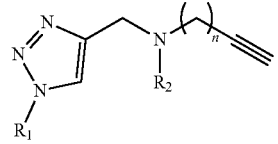

(II)

wherein:
n=1, 2, 3 or 4
$R_1$, and $R_2$, are independently selected from a hydrogen, carboxylic acid, a salt of carboxylic acid, amino, alkyl, heteroalkyl, cycloalkyl, heterocycloalkyl, substituted alkyl, substituted heteroalkyl, substituted cycloalkyl, substituted heterocycloalkyl, aryl, heteroaryl, substituted aryl, arylalkyl, substituted arylalkyl, and substituted heteroaryl, arylcarboxamido,
at least one substituent selected from $R_1$, and $R_2$ comprises X-L-, wherein:
X is selected from a reporter molecule, a carrier molecule, a solid phase, a therapeutic molecule such as peptide, a protein, an antibody, a polysaccharide, a nucleic acid polymer, an ion complexing moiety, a lipid or a non-biological organic polymer or polymeric micro or nano particle, that are optionally bound to one or more additional fluorophores; or
X is a reactive group such as carboxylic acid, an activated ester of carboxylic acid, an amine, a hydrazine, a haloacetamide, an alkyl halide, an isothiocynate or a maleimide group; and
L is an independently a single covalent bond or L is covalent linkage having 1-24 non-hydrogen atoms selected from the group consisting of C, N, O, P and S and composed of any combinations of single, double, triple or aromatic carbon-carbon bonds, carbon-nitrogen bonds, nitrogen-nitrogen bonds, carbon-oxygen bonds, carbon-sulfur bonds, phosphorus-oxygen bonds and phosphorus-nitrogen bonds in the form of alkyl, heteroalkyl, cycloalkyl, heterocycloalkyl, alkoxy, substituted alkoxy, substituted alkyl, substituted heteroalkyl, substituted cycloalkyl, substituted heterocycloalkyl, aryl, heteroaryl, substituted aryl, arylalkyl, substituted arylalkyl, and substituted heteroaryl;

In yet another embodiment, the invention provides a compound of the formula:

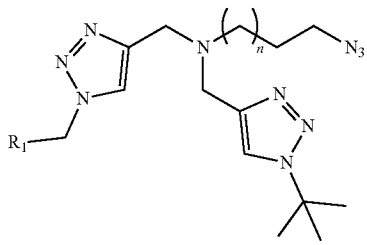

(III)

wherein:

n=0, 1, 2, 3 or 4

$R_1$, and $R_2$, are independently selected from a hydrogen, carboxylic acid, a salt of carboxylic acid, amino, alkyl, heteroalkyl, cycloalkyl, heterocycloalkyl, substituted alkyl, substituted heteroalkyl, substituted cycloalkyl, substituted heterocycloalkyl, aryl, heteroaryl, substituted aryl, arylalkyl, substituted arylalkyl, and substituted heteroaryl, arylcarboxamido, at least one substituent selected from $R_1$, comprises X-L-, wherein:

X is selected from a reporter molecule, a carrier molecule, a solid phase, a therapeutic molecule such as peptide, a protein, an antibody, a polysaccharide, a nucleic acid polymer, an ion complexing moiety, a lipid or a non-biological organic polymer or polymeric micro or nano particle, that are optionally bound to one or more additional fluorophores; or X is a reactive group such as carboxylic acid, an activated ester of carboxylic acid, an amine, a hydrazine, a haloacetamide, an alkyl halide, an isothiocynate or a maleimide group; and L is an independently a single covalent bond or L is covalent linkage having 1-24 non-hydrogen atoms selected from the group consisting of C, N, O, P and S and composed of any combinations of single, double, triple or aromatic carbon-carbon bonds, carbon-nitrogen bonds, nitrogen-nitrogen bonds, carbon-oxygen bonds, carbon-sulfur bonds, phosphorus-oxygen bonds and phosphorus-nitrogen bonds in the form of alkyl, heteroalkyl, cycloalkyl, heterocycloalkyl, alkoxy, substituted alkoxy, substituted alkyl, substituted heteroalkyl, substituted cycloalkyl, substituted heterocycloalkyl, aryl, heteroaryl, substituted aryl, arylalkyl, substituted arylalkyl, and substituted heteroaryl;

In another embodiment, the invention provides a compound of the formula:

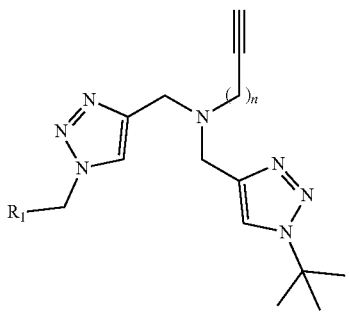

(IV)

wherein $R_1$, and $R_2$, are independently selected from a hydrogen, carboxylic acid, a salt of carboxylic acid, amino, alkyl, heteroalkyl, cycloalkyl, heterocycloalkyl, substituted alkyl, substituted heteroalkyl, substituted cycloalkyl, substituted heterocycloalkyl, aryl, heteroaryl, substituted aryl, arylalkyl, substituted arylalkyl, and substituted heteroaryl, arylcarboxamido, at least one substituent selected from $R_1$, and $R_2$ comprises X-L-, wherein:

X is selected from a reporter molecule, a carrier molecule, a solid phase, a therapeutic molecule such as peptide, a protein, an antibody, a polysaccharide, a nucleic acid polymer, an ion complexing moiety, a lipid or a non-biological organic polymer or polymeric micro or nano particle, that are optionally bound to one or more additional fluorophores; or X is a reactive group such as carboxylic acid, an activated ester of carboxylic acid, an amine, a hydrazine, a haloacetamide, an alkyl halide, an isothiocynate or a maleimide group; and L is an independently a single covalent bond or L is covalent linkage having 1-24 non-hydrogen atoms selected from the group consisting of C, N, O, P and S and composed of any combinations of single, double, triple or aromatic carbon-carbon bonds, carbon-nitrogen bonds, nitrogen-nitrogen bonds, carbon-oxygen bonds, carbon-sulfur bonds, phosphorus-oxygen bonds and phosphorus-nitrogen bonds in the form of alkyl, heteroalkyl, cycloalkyl, heterocycloalkyl, alkoxy, substituted alkoxy, substituted alkyl, substituted heteroalkyl, substituted cycloalkyl, substituted heterocycloalkyl, aryl, heteroaryl, substituted aryl, arylalkyl, substituted arylalkyl, and substituted heteroaryl.

In some embodiments, the compound of the formula (I), (II), (III) or (IV) is selected from the group consisting of:

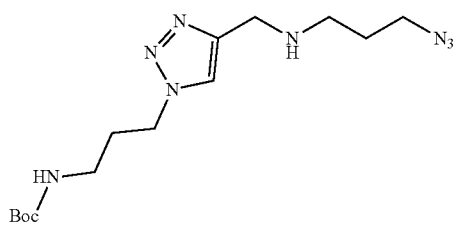

-continued
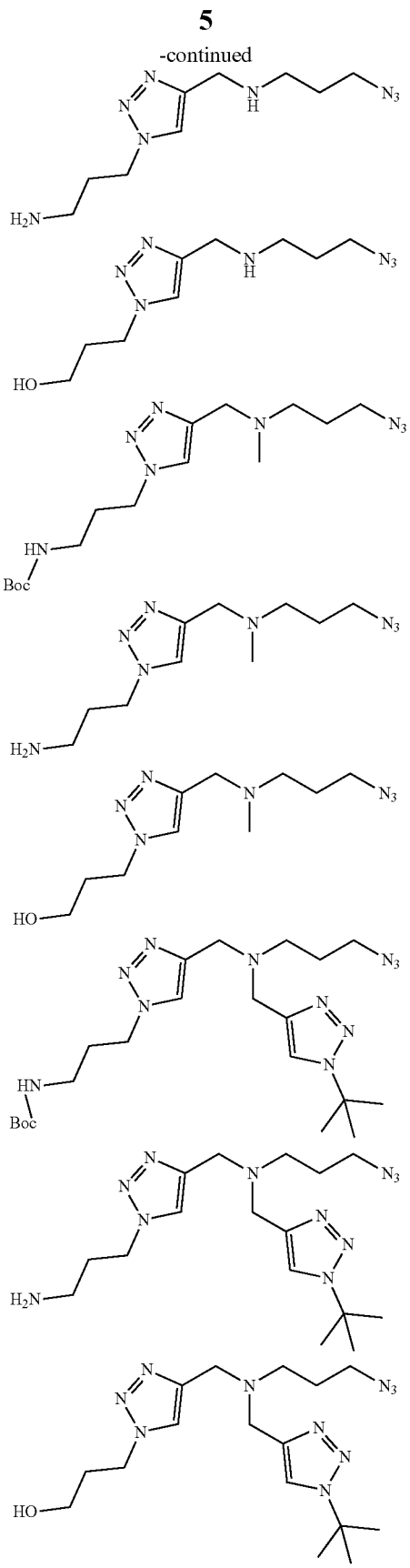
In yet another embodiment, the compound of the formula (I), (II), (III) or (IV) is selected from the group consisting of:
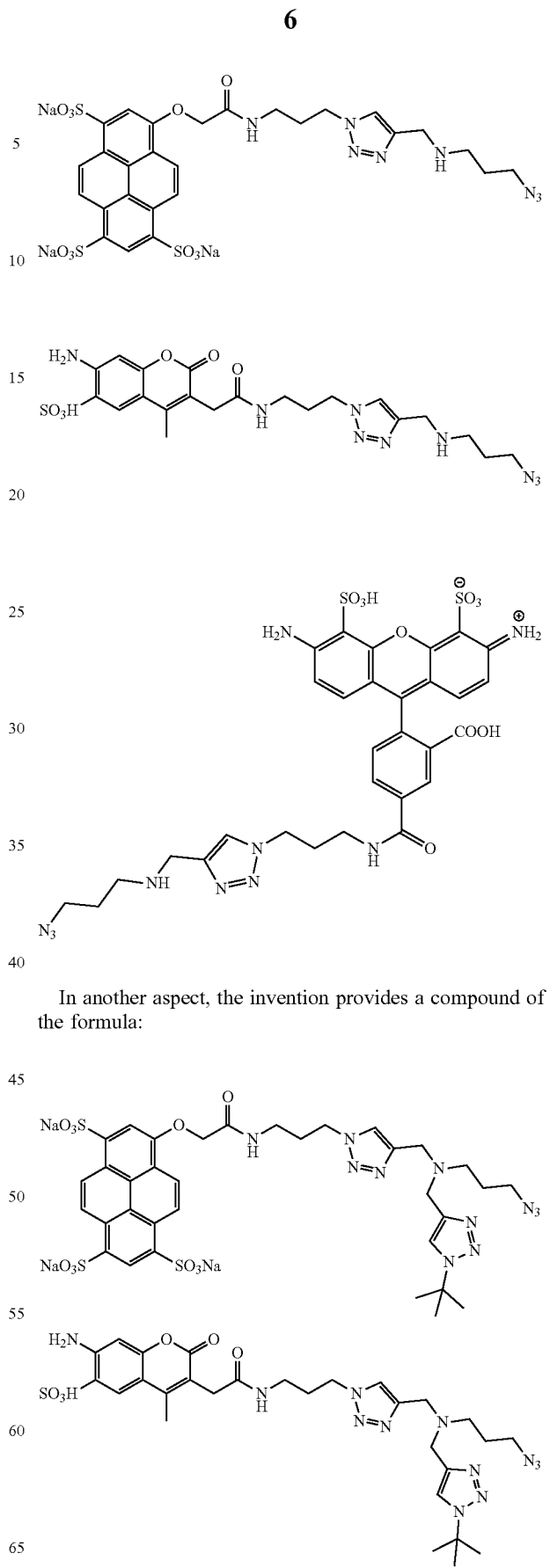
In another aspect, the invention provides a compound of the formula:

-continued

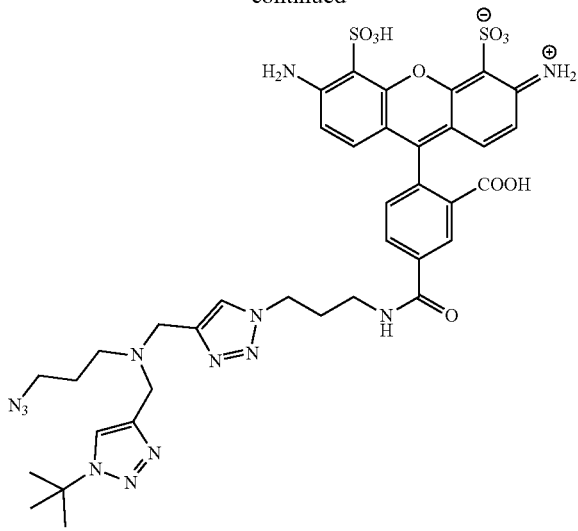

In some embodiments of the compound of the formula (I), (II), (III), or (IV), the reporter molecule comprises a chromophore, fluorophore, fluorescent protein, phosphorescent dye, tandem dye, particle, hapten, enzyme, or radioisotope. In some of these, the fluorophore is a xanthene, coumarin, cyanine, pyrene, oxazine, borapolyazaindacene, or carbopyranine. In others, the enzyme is horseradish peroxidase, alkaline phosphatase, beta-galactosidase, or beta-lactamase. In others, the particle is a semiconductor nanocrystal.

In some embodiments of the compound of the formula (I), (II), (III), or (IV), the carrier molecule is an amino acid, peptide, protein, polysaccharide, nucleoside, nucleotide, oligonucleotide, nucleic acid, hapten, psoralen, drug, hormone, lipid, lipid assembly, tyramine, synthetic polymer, polymeric microparticle, biological cell, cellular component, ion chelating moiety, enzymatic substrate, or virus.

In some embodiments of the compound of the formula (I), (II), (III), or (IV), the carrier molecule is an antibody, antibody fragment, antigen, avidin, streptavidin, biotin, dextran, IgG binding protein, fluorescent protein, agarose, or non-biological microparticle.

In some embodiments of the compound of the formula (I), (II), (III), or (IV), the solid support is an aerogel, hydrogel, resin, bead, biochip, microfluidic chip, silicon chip, multi-well plate, membrane, conducting metal, nonconducting metal, glass, or magnetic support.

In some embodiments of the compound of the formula (I), (II), (III), or (IV), the solid support is a silica gel, polymeric membrane, particle, derivatized plastic film, glass bead, cotton, plastic bead, alumina gel, polysaccharide, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene, nylon, latex bead, magnetic bead, paramagnetic bead, superparamagnetic bead, or starch.

In some embodiments of the compound of the formula (I), (II), (III), or (IV), the therapeutic molecule is taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoid, procaine, tetracaine, lidocaine, propranolol, puromycin, or analogs or homologs thereof.

In some embodiments of the compound of the formula (I), (II), (III), or (IV) the therapeutic molecule is an antimetabolite, alkylating agent, anthracycline, antibiotic, or anti-mitotic agent.

In another aspect, the invention provides a method of modifying a biomolecule comprising the step of reacting in a solution a biomolecule comprising an azide reactive moiety with a compound of the formula (II), or (V), wherein the therapeutic molecule is an antimetabolite, alkylating agent, anthracycline, antibiotic, or anti-mitotic agent to provide a modified biomolecule.

In another aspect, the invention provides a method of modifying a biomolecule comprising the step of reacting in a solution a biomolecule comprising an alkyne reactive moiety with a compound of the formula (I), or (III) wherein the therapeutic molecule is an antimetabolite, alkylating agent, anthracycline, antibiotic, or anti-mitotic agent to provide a modified biomolecule.

In some embodiments, the solution further comprises copper ions. In some of these, the solution further comprises at least one reducing agent. In some of these, the at least one reducing agent is ascorbate, Tris(2-Carboxyethyl)Phosphine (TCEP), TCP (2,4,6-trichlorophenol), NADH, NADPH, thiosulfate, 2-mercaptoethanol, dithiothreitol, glutathione, cysteine, metallic copper, quinone, hydroquinone, vitamin K1, Fe2+, Co2+, or an applied electric potential. In some of these, the at least one reducing agent is ascorbate.

In some of these, the solution further comprises a copper chelator. In some of these, the copper chelator is a copper I chelator. In some cases the copper chelator is THPTA, BTTAA, BTTP, BTTES, TBTA, N,N,N',N'-tetrakis(2-pyridylmethyl)ethylenediamine (TPEN), EDTA, neocuproine, N-(2-acetamido)iminodiacetic acid (ADA), pyridine-2,6-dicarboxylic acid (PDA), S-carboxymethyl-L-cysteine (SCMC), 1,10 phenanthroline, or a derivative thereof, trientine, glutathione, histidine, polyhistidine tetraethylenepolyamine (TEPA).

In others, the copper chelator is 1,10 phenanthroline, bathophenanthroline disulfonic acid (4,7-diphenyl-1,10-phenanthroline disulfonic acid), or bathocuproine disulfonic acid (2,9-dimethyl-4,7-diphenyl-1,10-phenanthroline disulfonate).

In another aspect, the invention is a kit comprising a compound of the formula (I), (II), (III), or (IV).

In some embodiments, the kit further comprises a copper ion source.

In some embodiments, the kit further comprises at least one reducing agent. In some of these, the at least one reducing agent is ascorbate, Tris(2-Carboxyethyl)Phosphine (TCEP), TCP (2,4,6-trichlorophenol), NADH, NADPH, thiosulfate, 2-mercaptoethanol, dithiothreitol, glutathione, cysteine, metallic copper, quinone, hydroquinone, vitamin K1, Fe2+, Co2+, or an applied electric potential. In others, the at least one reducing agent is ascorbate.

In some embodiments, the kit further comprises a copper chelator. In some of these, the copper chelator is a copper I chelator.

BRIEF DESCRIPTION OF THE DRAWINGS

The FIGURE presents the data for the kinectic analysis of Example 24.

DETAILED DESCRIPTION

The present invention has utility in the study of biomolecules, both in vivo and in vitro.

The present invention provides compositions, methods, and kits for the labeling, detecting, isolating and/or analysis of biomolecules modified by attachment of chemical handles.

Definitions and Abbreviations

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a ligand" includes a plurality of ligands and reference to "an antibody" includes a plurality of antibodies and the like.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds described herein may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY 5$^{TH}$ ED., Longman Scientific and Technical Ltd., Essex, 1991, pp. 809-816; and Heller, *Acc. Chem. Res.* 23: 128 (1990).

The compounds disclosed herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention. Where a disclosed compound includes a conjugated ring system, resonance stabilization may permit a formal electronic charge to be distributed over the entire molecule. While a particular charge may be depicted as localized on a particular ring system, or a particular heteroatom, it is commonly understood that a comparable resonance structure can be drawn in which the charge may be formally localized on an alternative portion of the compound.

Selected compounds having a formal electronic charge may be shown without an appropriate biologically compatible counterion. Such a counterion serves to balance the positive or negative charge present on the compound. As used herein, a substance that is biologically compatible is not toxic as used, and does not have a substantially deleterious effect on biomolecules. Examples of negatively charged counterions include, among others, chloride, bromide, iodide, sulfate, alkanesulfonate, arylsulfonate, phosphate, perchlorate, tetrafluoroborate, tetraarylboride, nitrate and anions of aromatic or aliphatic carboxylic acids. Preferred counterions may include chloride, iodide, perchlorate and various sulfonates. Examples of positively charged counterions include, among others, alkali metal, or alkaline earth metal ions, ammonium, or alkylammonium ions.

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkenyl") and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include derivatives of alkyl, such as those defined below, including heteroalkyl, cycloalkyl, heterocycloalkyl, substituted alkyl, substituted heteroalkyl, substituted cycloalkyl, and substituted heterocycloalkyl. Alkyl groups that are limited to hydrocarbon groups are termed "homoalkyl".

In some embodiments, an alkyl group contains between 1 and 25 carbons, between 1 and 20 carbons (i.e., $C_1$ to $C_{20}$ alkyl), between 1 and 15 carbons (i.e., $C_1$ to $C_{15}$ alkyl), between 1 and 10 carbons (i.e., $C_1$ to $C_{10}$ alkyl), or between 1 and 8 carbons (i.e., $C_1$ to $C_8$ alkyl). Straight, branched or cyclic hydrocarbon chains having eight or fewer carbon atoms may also be referred to herein as "lower alkyl". In addition, the term "alkyl" as used herein may further include one or more substitutions at one or more carbon atoms of the hydrocarbon chain fragment.

The term "carboxyalkyl" as used herein refers to a straight or branched-chain alkyl including cycloalkyl comprising at least one —COOH substituent. The terms "alkoxy," "alkylamino" and "alkylthio" (or thioalkoxy) are used in their conventional sense, and refer to heteroalkyl groups attached to the remainder of the molecule via an oxygen atom, an amino group, or a sulfur atom, respectively.

The term "acyl" or "alkanoyl" by itself or in combination with another term, means, unless otherwise stated, a stable straight or branched chain, or cyclic alkyl, or combinations thereof, with an acyl radical on at least one terminus of the alkyl. An "acyl radical" is a group derived from a carboxylic acid by removing the —OH moiety therefrom.

The term "amino" or "amine group" refers to the group —NR'R" where R' and R" are independently selected from hydrogen, alkyl, heteroalkyl, cycloalkyl, heterocycloalkyl, substituted alkyl, substituted heteroalkyl, substituted cycloalkyl, substituted heterocycloalkyl, aryl, heteroaryl, substituted aryl, arylalkyl, substituted arylalkyl, and substituted heteroaryl. In a primary amine group, both R' and R" are hydrogen, whereas in a secondary amine group, either, but not both, R' or R" is hydrogen. In a tertiary amine group, neither R' nor R" is a hydrogen. A substituted amine is an amine group wherein R' and/or R" is other than hydrogen. In addition, the terms "amine" and "amino" can include protonated and quaternized versions of nitrogen, comprising the group —NRR'R" and its biologically compatible anionic counterions.

As used herein, the term "heteroatom" includes oxygen (O), nitrogen (N), sulfur (S), phosphorus (P), silicon (Si), and selenium (Se).

The term "heteroalkyl," by itself or in combination with another term, means, unless otherwise stated, a straight or branched chain, or cyclic carbon-containing radical, or combinations thereof, consisting of the stated number of carbon atoms and at least one heteroatom selected from the group consisting of O, N, Si, P, S, and Se and wherein the nitrogen, phosphorous, sulfur, and selenium atoms are optionally oxidized, and the nitrogen heteroatom is optionally quaternized. The heteroatom(s) O, N, P, S, Si, and Se may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic moiety that can be a single ring or multiple rings (preferably from 1 to 3 rings), which are fused together or linked covalently. In some embodiments, an aryl group contains twenty or fewer carbon atoms, e.g., phenyl, naphthyl, biphenyl, and anthracenyl. One or more carbon atoms of the aryl group may also be substituted with, e.g., alkyl; aryl; heteroaryl; a halogen; nitro; cyano; hydroxyl, alkoxyl or aryloxyl; thio or mercapto, alkyl-, or arylthio; amino, alkylamino, arylamino, dialkyl-, diaryl-, or arylalkylamino; aminocarbonyl, alkylaminocarbonyl, arylaminocarbonyl, dialkylaminocarbonyl, di arylaminocarbonyl, or aryl alkylaminocarbonyl; carboxyl, or alkyl- or aryloxycarbonyl; aldehyde; aryl- or alkylcarbonyl; iminyl, or aryl- or alkyliminyl; sulfo; alkyl- or alkylcarbonyl; sulfo; alkyl- or arylsufonyl; hydroximinyl, or aryl- or alkoximinyl. In addition, two or more alkyl or heteroalkyl substituents of an aryl group may be combined to form fused aryl-alkyl or aryl-heteroalkyl ring systems (e.g., tetrahydronaphthyl). Substituents including heterocyclic groups (e.g., heteroaryloxy, and heteroaralkylthio) are defined by analogy to the above-described terms.

The term "heteroaryl" refers to aryl groups (or rings) that contain from one to four heteroatoms selected from N, O, S, and Se, wherein the nitrogen, sulfur, and selenium atoms are optionally oxidized, and the nitrogen atom(s) are optionally quaternized. A heteroaryl group can be attached to the remainder of the molecule through a heteroatom. Nonlimiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3] dioxol-5-yl and 6-quinolyl. Substituents for aryl and heteroaryl ring systems are selected from the group of acceptable substituents described below. For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxyl)propyl, and the like).

Each of the above terms (e.g., "alkyl," "heteroalkyl," "aryl," "heteroaryl," etc.) includes both substituted and unsubstituted forms of the indicated radical. Nonlimiting exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR, =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R, R", R"' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"'R"")=NR"", —NR—C(NR'R") =NR"', —S(O)R', —S(O)$_2$R', —S(O)$_2$NR'R", —NRSO$_2$R', —CN and —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted aryl and substituted or unsubstituted heteroaryl. When a compound includes more than one R group, for example, each of the R groups is independently selected as are each R', R", R"' and R"" groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R"')$_d$—, where s and d are independently integers of from 0 to 3, and X is —O—, —NR'—, —S—, —S(O)—, —S(O)$_2$—, or —S(O)$_2$NR'—. The substituents R, R', R" and R"' are preferably independently selected from hydrogen or substituted or unsubstituted ($C_1$-$C_6$)alkyl.

The term "chain length," as used herein, refers to the smallest number of carbon and/or heteroatoms between two substituents. As a nonlimiting example, the chain length between X and Y in the molecule X—($CH_2$)$_3$—CH($CH_2CH_3$)—NH—Y is 5.

The term "activated alkyne," as used herein, refers to a cyclooctyne that selectively reacts with an azide on another molecule to form a covalent chemical bond between the activated alkyne group and the alkyne reactive group. Activated alkynes include, but are not limited to, cyclooctynes and difluorocyclooctynes, described, e.g., in Agard et al., J. Am. Chem. Soc., 2004, 126 (46):15046-15047; dibenzocyclooctynes, described, e.g., in Boon et al., WO2009/067663 A1 (2009); and aza-dibenzocyclooctynes, described, e.g., in Debets et al., Chem. Comm, 2010, 46:97-99. These dibenzocyclooctynes (including the aza-dibenzocyclooctynes) described above are collectively referred to herein as cyclooctyne groups.

The term "affinity," as used herein, refers to the strength of the binding interaction of two molecules, such as an antibody and an antigen, or a positively charged moiety and a negatively charged moiety. For bivalent molecules such as antibodies, affinity is typically defined as the binding strength of one binding domain for the antigen, e.g. one Fab fragment for the antigen. The binding strength of both binding domains together for the antigen is referred to as "avidity". As used herein "high affinity" refers to a ligand that binds to an antibody having an affinity constant ($K_a$) greater than $10^4$ $M^{-1}$, typically $10^5$-$10^{11}M^{-1}$; as determined by inhibition ELISA or an equivalent affinity determined by comparable techniques such as, for example, Scatchard plots or using $K_d$/dissociation constant, which is the reciprocal of the $K_a$.

The term "alkyne reactive," as used herein, refers to a chemical moiety that selectively reacts with an alkyne, such as a terminal alkyne or an activated alkyne, on another molecule to form a covalent chemical bond between the alkyne modified group and the alkyne reactive group. Examples of alkyne-reactive groups include, but are not limited to, azide and nitrones. "Alkyne-reactive" can also refer to a molecule that contains a chemical moiety that selectively reacts with an alkyne group.

The term "antibody," as used herein, refers to a protein of the immunoglobulin (Ig) superfamily that binds noncovalently to certain substances (e.g. antigens and immunogens) to form an antibody-antigen complex. Antibodies can be polyclonal or monoclonal. Antibodies can also be chimeric, humanized, or human antibodies. It is understood that the term "antibody" as used herein includes within its scope any of the various classes or sub-classes of immunoglobulin derived from any of the animals conventionally used, or from human.

The term "antibody fragments," as used herein, refers to fragments of antibodies that retain the principal selective binding characteristics of the whole antibody. Nonlimiting exemplary antibody fragment include Fab, Fab', F(ab')$_2$, Fv, and single-chain Fv (scFv). Further nonlimiting exemplary antibody fragments include (i) the Fd fragment, consisting of the VH and CH1 domains; (ii) the dAb fragment (Ward, et al., *Nature* 341, 544 (1989)), which consists of a VH domain; and (iii) isolated CDR regions. In addition, arbitrary fragments can be made using recombinant technology that retains antigen-recognition characteristics.

The term "antigen," as used herein, refers to a molecule or molecules to which an antibody binds selectively. An antigen may comprise any type of molecule, such as, for example, protein, oligonucleotide, polysaccharide, or small molecule. In some embodiments, an antigen comprises more than one molecule, such as for example, a heterodimeric receptor, a receptor bound to its ligand, or a complex comprising a protein and a small molecule or oligonucleotide. In some embodiments, a target is an antigen.

The term "aqueous solution," as used herein, refers to a solution that is at least 50% water. In some embodiments, an aqueous solution retains the solution characteristics of water.

The term "azide reactive," as used herein, refers to a chemical moiety that selectively reacts with an azide on another molecule to form a covalent chemical bond between the azido modified group and the azide reactive group. Examples of azide-reactive groups include, but are not limited to, alkyne, including, but not limited to, terminal alkynes and activated alkynes; and phosphines, including, but not limited to, triarylphosphines. "Azide-reactive" can also refer to a molecule that contains a chemical moiety that selectively reacts with an azido group.

The term "biomolecule," as used herein, refers to proteins, peptides, amino acids, glycoproteins, nucleic acids, nucleotides, nucleosides, oligonucleotides, sugars, oligosaccharides, lipids, hormones, proteoglycans, carbohydrates, polypeptides, polynucleotides, polysaccharides, drugs, prodrugs, etc., which may be found in a living organism (including an isolated cell). A biomolecule need not be a naturally-occurring molecule, but may be a molecule that has been introduced into the living organism or an ancestor of the living organism, e.g., directly, through transgenic methods, or otherwise.

The term "carrier molecule," as used herein, refers to a biological or a non-biological moiety that is covalently bonded to a compound of the present invention, and which confers a desirable property on the compound and/or on a biomolecule conjugated thereto. Nonlimiting exemplary such desirable properties include binding properties, such as, for example, the ability to specifically bind to another moiety (e.g., a member of a binding pair); increasing half-life; increasing solubility; and directing the compound to a particular location in a cell or organism. Such moieties include, but are not limited to, amino acids, peptides, proteins, polysaccharides, nucleosides, nucleotides, oligonucleotides, nucleic acids, haptens, psoralens, drugs, hormones, lipids, lipid assemblies, synthetic polymers, polymeric microparticles, biological cells, viruses, and combinations thereof.

The term, "chemical handle," as used herein, refers to a functional group that is capable of undergoing a click reaction, a 1,3-dipolar cycloaddition, and/or a Staudinger ligation. Nonlimiting exemplary chemical handles include alkyne-reactive moieties, such as azide; and azide-reactive moieties, such as alkynes, including, but not limited to, terminal alkynes and activated alkynes; and phosphines, including, but not limited to, a triarylphosphine; and the like.

The term "complementary chemical handle," as used herein, refers to a functional group that is capable of undergoing a click reaction, a 1,3-dipolar cycloaddition, and/or a Staudinger ligation with a specified chemical handle. For example, for an azide chemical handle, complementary chemical handles include, but are not limited to, alkynes, such as terminal alkynes and activated alkynes, and phosphines, such as triarylphosphines.

The terms "click chemistry" and "click reaction," as used herein, refer to copper ion-catalyzed 1,3-dipolar cycloadditions between an azide and a terminal alkyne to form a 1,2,3-triazole.

The term "1,3-dipolar cycloaddition," as used herein, refers to reactions between an azide and an alkyne to form a 1,2,3-triazole.

The term "copper ion source," as used herein, refers to any source of Cu(I) ions, whether or not formation of Cu(I) ions involves other agents, such as reducing agents. Nonlimiting exemplary copper ion sources include copper salts, such as $Cu(NO_3)_2 Cu(OAc)_2$ or $CuSO_4$; copper halides, such as CuBr and CuI; and copper-containing metals, such as copper wire.

The terms "copper ion chelator" and "copper chelator," as used herein, refer to a moiety that binds to, and stabilizes, Cu(I) ions. Nonlimiting exemplary copper chelators are discussed herein.

The term "halogen," as used herein, refers to an atom selected from F, Cl, Br, and I.

The term "linker" or "L", as used herein, refers to a single covalent bond or a series of stable covalent bonds incorporating 1-30 nonhydrogen atoms selected from the group consisting of C, N, O, S, P, Si, and Se. Exemplary linking members include moieties that includes —C(O)NH—, —C(O)O—, —NH—, —S—, —O—, and the like. In some embodiments, a linker has a chain length of 1-30 atoms, or 1-25 atoms, or 1-20 atoms, or 1-15 atoms, or 1-10 atoms, or 1-5 atoms. A "cleavable linker" is a linker that has one or more covalent bonds that can be broken under particular reaction conditions or in the presence of a particular molecule or enzyme, such that the moiety on one side of the cleavable linker is no longer covalently bound to the moiety on the other side of the cleavable linker. The term "cleavable group" refers to a moiety that allows for release of a portion, e.g., a reporter molecule, carrier molecule or solid support, of a conjugate from the remainder of the conjugate by cleaving a bond linking the released moiety to the remainder of the conjugate. Such cleavage (for both cleavable linkers and cleavable groups) is either chemical in nature, or enzymatically mediated. Exemplary enzymatically cleavable linkers and groups include natural amino acids or peptide sequences that end with a natural amino acid. In addition to enzymatically cleavable linkers and groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleavable groups are known in the art. See, for example, Jung et al., *Biochem. Biophys. Acta*, 761: 152-162 (1983); Joshi et al., *J. Biol. Chem.*, 265: 14518-14525 (1990); Zarling et al., *J. Immunol.*, 124: 913-920 (1980); Bouizar et al., *Eur. J. Biochem.*, 155: 141-147 (1986); Park et al., *J. Biol. Chem.*, 261: 205-210 (1986); Browning et al., *J. Immunol.*, 143: 1859-1867 (1989). Moreover a broad range of cleavable, bifunctional (both homo- and heterobifunctional) spacer arms are commercially available. An exemplary cleavable linker or group, an ester, may be cleaved by a reagent, e.g. sodium hydroxide, resulting in a carboxylate-containing product and a hydroxyl-containing product.

The term "low copper," as used herein, refers to a copper concentration of less than 1 millimolar.

The term "modified biomolecule" as used herein refers to a biomolecule which has been modified by covalent attachment of at least one chemical handle. A biomolecule may be modified in vitro or in vivo.

The term "phosphine reactive" as used herein refers to a chemical moiety that selectively reacts via Staudinger ligation with a phosphine group, including but not limited to a triarylphosphine group, on another molecule to form a covalent chemical bond. Examples of phosphine reactive groups include, but are not limited to, azide.

The terms "protein" and "polypeptide" are used herein in a generic sense to refer to polymers of amino acid residues of any length. The term "peptide" is used herein to refer to polypeptides having fewer than 100 amino acid residues, typically fewer than 10 amino acid residues. The amino acid residues in a polypeptide, protein, or peptide may be naturally-occurring amino acid residues or non-naturally occurring amino acid residues.

The term "reducing agent," as used herein, refers to an agent that is capable of reducing Cu(II) to Cu(I). Nonlimiting exemplary reducing agents include ascorbate, tris(2-carboxyethyl)phosphine (TCEP), NADH, NADPH, thiosulfate, metallic copper, hydroquinone, vitamin $K_1$, glutathione, cysteine, 2-mercaptoethanol, dithiothreitol, and an applied electric potential. Nonlimiting exemplary metals that may act as reducing agents include Al, Be, Co, Cr, Fe, Mg, Mn, Ni, Zn, Au, Ag, Hg, Cd, Zr, Ru, Fe, Co, Pt, Pd, Ni, Rh, and W.

The term "reporter molecule" refers to a moiety that is directly or indirectly detectable. In some embodiments, and as a non-limiting example, a reporter molecule may be directly detectable, e.g., due to its spectral properties. In some embodiments, and as a non-limiting example, a reporter molecule may be indirectly detectable, e.g., due to its enzymatic activity, wherein the enzymatic activity produces a directly detectable signal. Such reporter molecules include, but are not limited to, radiolabels; pigments, dyes, and other chromogens; spin labels; fluorescent labels (i.e., fluorophores such as coumarins, cyanines, benzofurans, quinolines, quinazolinones, indoles, benzazoles, borapolyazaindacenes, and xanthenes, including fluoresceins, rhodamines, and rhodols); chemiluminescent substances, wherein the detectable signal is generated by chemical modification of substance; metal-containing substances; enzymes, wherein the enzyme activity generates a signal (such as, for example, by forming a detectable product from a substrate; haptens that can bind selectively to another molecule (such as, for example, an antigen that binds to an antibody; or biotin, which binds to avidin and streptavidin). Many reporter molecules are known in the art, some of which are described, e.g., in Richard P. Haugland, Molecular Probes Handbook of Fluorescent Probes and Research Products ($9^{th}$ edition, CD-ROM, September 2002), supra.

The term "solid support," as used herein, refers to a material that is substantially insoluble in a selected solvent system, or which can be readily separated (e.g., by precipitation) from a selected solvent system in which it is soluble. Solid supports useful in practicing the present invention may include groups that are activated or capable of activation such that one or more compounds described herein will bind to the solid support.

The terms "structural integrity of the [biomolecule] is not reduced" or "preservation of the structural integrity of the [biomolecule]", as used herein, mean that either: 1) when analyzed by gel electrophoresis and detection (such as staining), a band or spot arising from the labeled biomolecule is not reduced in intensity by more than 20%, and preferably not reduced by more than 10%, with respect to the corresponding band or spot arising from the same amount of the electrophoresed unlabeled biomolecule, arising from the labeled biomolecule analyzed; or 2) when analyzed by gel electrophoresis, a band or spot arising from the labeled biomolecule is not observed to be significantly less sharp than the corresponding band or spot arising from the same amount of the electrophoresed unlabeled biomolecule, where "significantly less sharp" (synonymous with "significantly more diffuse") means the detectable band or spot takes up at least 5% more, preferably 10% more, more preferably 20% more area on the gel than the corresponding unlabeled biomolecule. Other reproducible tests for structural integrity of labeled biomolecules include, without limitation detection of released amino acids or peptides, or mass spectrometry.

The term "therapeutic molecule" refers to a molecule that can be used to treat and/or alleviate a condition and/or symptom in a subject, and/or can be used to affect biological processes in cells in vitro. Therapeutic molecules include, but are not limited to, antimetabolites, alkylating agents, anthracyclines, antibiotics, and anti-mitotic agents. Nonlimiting exemplary therapeutic molecules include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoid, procaine, tetracaine, lidocaine, propranolol, puromycin, abrin, ricin A, *pseudomonas* exotoxin, diphtheria toxin, tumor necrosis factor, γ-interferon, α-interferon, nerve growth factor, platelet derived growth factor, tissue plasminogen activator, interleukin-1, interleukin-2, interleukin-6, granulocyte macrophage colony stimulating factor, or granulocyte colony stimulating factor, and analogs or homologs thereof.

The present invention provides low-copper click reactions, 1,3-dipolar cycloadditions, and Staudinger ligations involving a modified biomolecule and a compound of any one of Formulas (I) to (XIII). In some embodiments, the modified biomolecule comprises an azide moiety and the compound of any one of Formulas (I) to (XIII) comprises a terminal alkyne. In some embodiments, the modified biomolecule comprises an alkyne, such as a terminal alkyne or an activated alkyne, or a phosphine, such as a triarylphosphine, and the compound of any one of Formulas (I) to (XIII) comprises an azide moiety.

Accordingly, provided herein are compounds, compositions, methods, and kits for the labeling, detecting, isolating and/or analysis of biomolecules. In some embodiments, presented are novel compounds comprising an azide moiety or an alkyne moiety. In some embodiments, methods are provided for covalently attaching the novel compounds to modified biomolecules using a click reaction, a 1,3-dipolar cycloaddition, or a Staudinger ligation. In some such embodiments, the method comprises labeling, detecting, isolating and/or analyzing the biomolecule.

Click Chemistry

Azides and terminal alkynes can undergo Cu(I)-catalyzed Azide-Alkyne Cycloaddition (CuAAC) at room temperature. Such Cu(I)-catalyzed azide-alkyne cycloadditions, sometimes referred to as click chemistry, typically results in formation of a 1,2,3-triazole. Various exemplary click reactions are known in the art, and are described, e.g., in U.S. Publication No. 2005/0222427.

Click reactions can be performed in a variety of aqueous solutions, including, but not limited to, water, and mixtures of water and various miscible or partially miscible organic solvents. Nonlimiting such organic solvents include alcohols, dimethyl sulfoxide (DMSO), dimethyl formamide (DMF), tert-butanol (tBuOH) and acetone.

In some embodiments, the copper used as a catalyst in a click reaction is Cu(I) ions. Exemplary sources of Cu(I) ions include, but are not limited to, cuprous halides such as cuprous bromide or cuprous iodide. In some embodiments, a click reaction is carried out in the presence of Cu(II) ions and a reducing agent, which reduces the Cu(II) to Cu(I) in situ. Exemplary sources of Cu(II) ions include, but are not limited to, $Cu(NO_3)_2$, $Cu(OAc)_2$, and $CuSO_4$. Nonlimiting exemplary reducing agents include ascorbate, tris(2-carboxyethyl)phosphine (TCEP), NADH, NADPH, thiosulfate, metallic copper, hydroquinone, vitamin $K_1$, glutathione, cysteine, 2-mercaptoethanol, dithiothreitol, $Fe^{2+}$, $Co^{2+}$, and an applied electric potential. In some embodiments, a reducing agent is a metal selected from Al, Be, Co, Cr, Fe, Mg, Mn, Ni, Zn, Au, Ag, Hg, Cd, Zr, Ru, Fe, Co, Pt, Pd, Ni, Rh, and W.

In some embodiments, the reducing agent is included in a click reaction in a micromolar to millimolar range. In some embodiments, the concentration of the reducing agent is between 100 μM and 100 mM, between 10 μM and 10 mM, or between 1 μM and 1 mM.

In some embodiments, a click reaction includes a chelator that stabilizes Cu(I) ions. Nonlimiting exemplary such chelators are described herein.

In some embodiments, at least one copper chelator is included in a click reaction. In some such embodiments, the copper chelator is added after a Cu(II) source has been contacted with a reducing agent. In some embodiments, the copper chelator is added at the same time the Cu(II) source is contacted with a reducing agent. In some embodiments, a copper chelator is added to a solution containing one or both of the click reactants (i.e., a solution containing one or both of the azide-containing reactant and the alkyne-containing reactant), and a solution containing the Cu(II) source and the reducing agent is subsequently added to initiate the click reaction.

Activated Alkyne Chemistry (1,3-Dipolar Cycloadditions)

In some instances, azides and alkynes can undergo catalyst-free 1,3-dipolar cycloaddition when an activated alkyne is used. In some embodiments, alkynes can be activated by ring strain such as, by way of example only, eight membered ring structures, including seven to ten-membered ring structures with electron-withdrawing groups appended thereon. In some embodiments, alkynes can be activated by the addition of a Lewis acid such as, by way of example only, Au(I) or Au(III). Nonlimiting exemplary activated alkynes include cyclooctynes and difluorocyclooctynes, which are described, e.g., in Agard et al., *J. Am. Chem. Soc.,* 2004, 126 (46):15046-15047; dibenzocyclooctynes, which are described, e.g., in Boon et al., WO2009/067663 A1; and aza-dibenzocyclooctynes, which are described, e.g., in Debets et al., *Chem. Comm.,* 2010, 46:97-99.

Typically, an activated alkyne conjugated with fluorophores or antibody undergoes cycloaddition to azide in one to twelve hour at room temperature. The reaction can be carried out in organic or aqueous solvents, buffers like PBS, TRIS or mixtures of buffers and organic solvents.

In some embodiments of the methods described herein, a modified biomolecule comprises an activated alkyne and a compound of any one of Formulas (I) to (XIII) comprises an azide.

Staudinger Ligation

In a Staudinger ligation, an azide is reacted with a triarylphosphine comprising an electrophilic trap (typically, a methyl ester). Following formation of an aza-ylide intermediate, the intermediate rearranges to produce a ligated product having an amide linkage, and a phosphine oxide. Such ligations are described, e.g., in U.S. Publication No. 2006/0276658. In some embodiments, the phosphine comprises an acyl group such as an ester, thioester or N-acyl imidazole (i.e. a phosphinoester, phosphinothioester, phosphinoimidazole) to trap the aza-ylide intermediate and form an amide bond upon hydrolysis. In some embodiments, the phosphine can be a di- or triarylphosphine to stabilize the phosphine. The phosphines used in Staudinger ligation methods described herein include, but are not limited to, cyclic or acyclic, halogenated, bisphosphorus, or polymeric phosphines.

Compounds for Conjugating Biomolecules

In some embodiments, the present invention provides compounds having the formula:

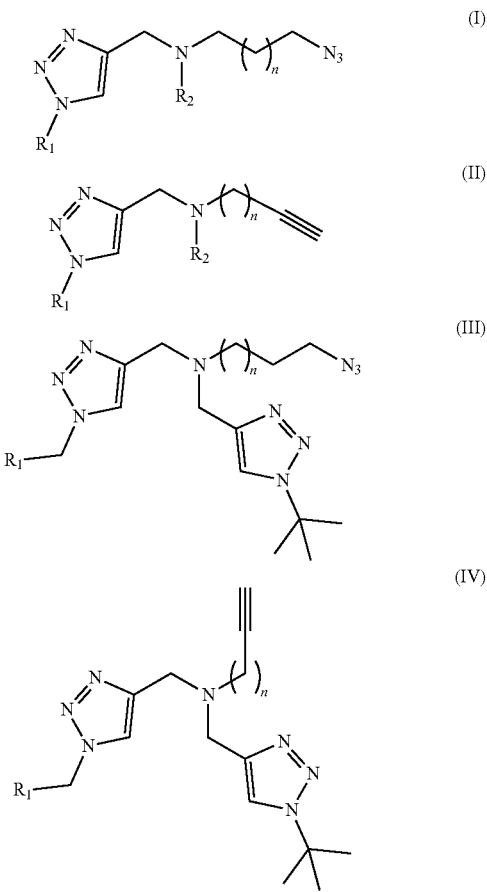

wherein: R1, and R2, are independently selected from hydrogen, halogen, —SO3X, a carboxylic acid, a salt of carboxylic acid, CN, nitro, hydroxyl, amino, hydrazine, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido, alkyl and aryl portions are optionally substituted one or more times by halogen, —SO₃X, a carboxylic acid, a salt of carboxylic acid, CN, nitro, hydroxyl, amino, hydrazine, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido, at least one substituent selected from $R_1$, and $R_2$ comprises X-L-, wherein:

X is selected from a reporter molecule, a carrier molecule, a solid phase, a therapeutic molecule such as peptide, a protein, an antibody, a polysaccharide, a nucleic acid polymer, an ion complexing moiety, a lipid or a non-biological organic polymer or polymeric micro or nano particle, that are optionally bound to one or more additional fluorophores; or X is a reactive group such as carboxylic acid, an activated ester of carboxylic acid, an amine, a hydrazine, a haloacetamide, an alkyl halide, an isothiocynate or a maleimide group; and L is an independently a single covalent bond or L is covalent linkage having 1-24 non-hydrogen atoms selected from the group consisting of C, N, O, P and S and composed of any combinations of single, double, triple or aromatic carbon-carbon bonds, carbon-nitrogen bonds, nitrogen-nitrogen bonds, carbon-oxygen bonds, carbon-sulfur bonds, phosphorus-oxygen bonds and phosphorus-nitrogen bonds in the form of alkyl, heteroalkyl, cycloalkyl, heterocycloalkyl, alkoxy, substituted alkoxy, substituted alkyl, substituted heteroalkyl, substituted cycloalkyl, substituted heterocycloalkyl, aryl, heteroaryl, substituted aryl, arylalkyl, substituted arylalkyl, and substituted heteroaryl;

In some embodiments, the compound is of the formula:

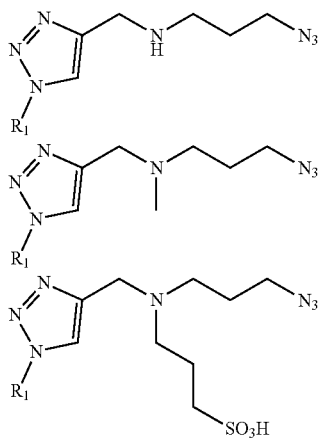

In some embodiments, the compound is of the formula:

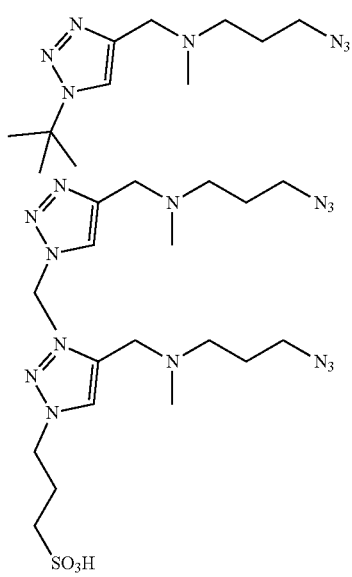

In yet other embodiments, the compound is of the formula:

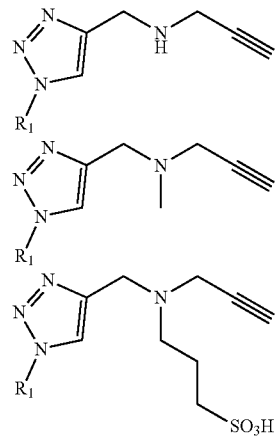

In yet other embodiments, the compound is of the formula:

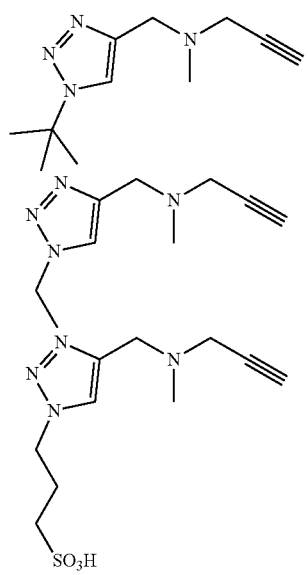

wherein $R_1$ comprises X-L-, wherein:
X is selected from a reporter molecule, a carrier molecule, a solid phase, a therapeutic molecule such as peptide, a protein, an antibody, a polysaccharide, a nucleic acid polymer, an ion complexing moiety, a lipid or a non-biological organic polymer or polymeric micro or nano particle, that are optionally bound to one or more additional fluorophores; or X is a reactive group such as carboxylic acid, an activated ester of carboxylic acid, an amine, a hydrazine, a haloacetamide, an alkyl halide, an isothiocynate or a maleimide group; and L is an independently a single covalent bond or L is covalent linkage having 1-24 non-hydrogen atoms selected from the group consisting of C, N, O, P and S and composed of any combinations of single, double, triple or aromatic carbon-carbon bonds, carbon-nitrogen bonds, nitrogen-nitrogen bonds, carbon-oxygen bonds, carbon-sulfur bonds, phosphorus-oxygen bonds and phosphorus-nitrogen bonds in the form of alkyl, heteroalkyl, cycloalkyl, heterocycloalkyl, alkoxy, substituted alkoxy, substituted alkyl, substituted heteroalkyl, substituted cycloalkyl, substituted heterocycloalkyl, aryl, heteroaryl, substituted aryl, arylalkyl, substituted arylalkyl, and substituted heteroaryl;

In some embodiments, the reporter molecule comprises a chromophore, fluorophore, fluorescent protein, phosphorescent dye, tandem dye, particle, hapten, enzyme, or radioisotope. In some embodiments, the fluorophore is a xanthene, coumarin, cyanine, pyrene, oxazine, borapolyazaindacene, or carbopyranine. In some embodiments, the enzyme is horseradish peroxidase, alkaline phosphatase, beta-galactosidase, or beta-lactamase. In some embodiments, the particle is a semiconductor nanocrystal.

In some embodiments, the carrier molecule is an amino acid, peptide, protein, polysaccharide, nucleoside, nucleotide, oligonucleotide, nucleic acid, hapten, psoralen, drug, hormone, lipid, lipid assembly, tyramine, synthetic polymer, polymeric microparticle, biological cell, cellular component, ion chelating moiety, enzymatic substrate, or virus. In some embodiments, the carrier molecule is an antibody, antibody fragment, antigen, avidin, streptavidin, biotin, dextran, IgG binding protein, fluorescent protein, agarose, or non-biological microparticle.

In some embodiments, the solid support is an aerogel, hydrogel, resin, bead, biochip, microfluidic chip, silicon chip, multi-well plate, membrane, conducting metal, non-conducting metal, glass, or magnetic support. In some embodiments, the solid support is a silica gel, polymeric membrane, particle, derivatized plastic film, glass bead, cotton, plastic bead, alumina gel, polysaccharide, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene, nylon, latex bead, magnetic bead, paramagnetic bead, superparamagnetic bead, or starch.

In some embodiments, the therapeutic molecule is taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoid, procaine, tetracaine, lidocaine, propranolol, puromycin, or analogs or homologs thereof. In some embodiments, the therapeutic molecule is an antimetabolite, alkylating agent, anthracycline, antibiotic, or anti-mitotic agent. In some embodiments, the therapeutic molecule is abrin, ricin A, *pseudomonas* exotoxin, diphtheria toxin, tumor necrosis factor, γ-interferon, α-interferon, nerve growth factor, platelet derived growth factor, tissue plasminogen activator, interleukin-1, interleukin-2, interleukin-6, granulocyte macrophage colony stimulating factor, or granulocyte colony stimulating factor.

Reporter Molecules

In some embodiments, a compound of any one of Formulas (I) to (IV) comprises a reporter molecule. The reporter molecules used in the methods and compositions provided herein include any directly or indirectly detectable reporter molecule that can be covalently attached as a substituent of a compound of any one of Formulas (I) to (IV).

Reporter molecules used in the methods and compositions described herein include, but are not limited to, chromophores, fluorophores, fluorescent proteins, phosphorescent dyes, tandem dyes, particles, haptens, enzymes, and radioisotopes. In some embodiments, a reporter molecule is a fluorophore, a fluorescent protein, a hapten, or an enzyme.

A fluorophore is any chemical moiety that exhibits an absorption maximum at wavelengths greater than 280 nm, and retains its spectral properties when covalently attached to a biomolecule following reaction of a compound of any one of Formulas (I) to (IV) comprising the fluorophore with the modified biomolecule. Fluorophores include, without limitation, pyrenes; anthracenes; naphthalenes; acridines; stilbenes; indoles and benzindoles; oxazoles and benzoxazoles; thiazoles and benzothiazoles; 4-amino-7-nitrobenz-2-oxa-1,3-diazoles (NBD); cyanines; carbocyanines; carbostyryls; porphyrina; salicylates; anthranilates; azulenes; perylenes; pyridines; quinolines; borapolyazaindacenes; xanthenes (including, but not limited to, fluoresceins (such as benzo- or dibenzofluoresceins, seminaphthofluoresceins, or naphthofluoresceins), rhodols (such as eminaphthorhodafluors), and rhodamine); oxazines and benzoxazines (including, but not limited to, resorufins, aminooxazinones, diaminooxazines, and their benzo-substituted analogs); carbazines; phenalenones; coumarins; benzofurans; benzphenalenones; carbopyranines, semiconductor nanocrystals; and derivatives of any of the above.

In some embodiments, a reporter molecule is selected from a xanthene (including, but not limited to, sulfonated xanthenes, fluorinated xanthenes, rhodol, rhodamine, fluorescein and derivatives thereof), coumarin (including, but not limited to, sulfonated coumarin and fluorinated coumarin), cyanine (including, but not limited to, sulfonated cyanine), pyrene, oxazine, borapolyazaindacene, carbopyranine, and semiconductor nanocrystal.

One skilled in the art can select a fluorophore to be included as a substituent of a compound of any one of Formulas (I) to (IV) according to the particular application. Physical properties of a fluorophore that can be used for detection of modified biomolecules include, but are not limited to, spectral characteristics (absorption, emission, and stokes shift), fluorescence intensity, lifetime, polarization and photo-bleaching rate, and combinations thereof. In various embodiments, one or more of the physical properties can be used to distinguish one fluorophore from another, and thereby allow for multiplexed analysis. In some embodiments, the fluorophore has an absorption maximum at wavelengths greater than 480 nm, at wavelengths between 488 nm to 514 nm (particularly suitable for excitation by the output of the argon-ion laser excitation source), or at wavelengths near 546 nm (particularly suitable for excitation by a mercury arc lamp).

Many of fluorophores can also function as chromophores and thus the described fluorophores may also be used as chromophore reporter molecules in the methods and compositions described herein.

In some embodiments, a reporter molecule is an enzyme. In some embodiments, an enzyme is a desirable label because it can amplify the detectable signal, thus increasing assay sensitivity. In some embodiments, the enzyme itself is not directly detectable, but its activity can be used to create a detectable signal when the enzyme is contacted with an appropriate substrate, such that the converted substrate produces, for example, a fluorescent, colorimetric, or luminescent signal. Various substrates are known in the art, some of which are described in the Molecular Probes Handbook, supra.

In some embodiments, when an enzyme reporter molecule is an oxidoreductase such as, by way of example only, horseradish peroxidase, suitable substrates include, but are not limited to, 3,3'-diaminobenzidine (DAB) or 3-amino-9- ethylcarbazole (AEC), 2,2-azino-bis(3-ethylbenzothiazoline-6-sulfonic acid) (ABTS), o-phenylenediamine (OPD), 3,3',5,5'-tetramethylbenzidine (TMB), o-dianisidine, 5-aminosalicylic acid, 4-chloro-1-naphthol, 4-hydroxy-3-methoxyphenylacetic acid, reduced phenoxazines and reduced benzothiazines, including Amplex® Red reagent and its variants (U.S. Pat. No. 4,384,042), Amplex UltraRed and its variants (WO05/042504), reduced dihydroxanthenes, including dihydrofluoresceins and dihydrorhodamines, including dihydrorhodamine 123. Peroxidase substrates that may be used with the enzymatic reporter molecules described herein also include, but are not limited to, tyramides (U.S. Pat. Nos. 5,196,306; 5,583,001 and 5,731,158), which can be intrinsically detectable before action of the enzyme but are "fixed in place" by the action of a peroxidase in the process described as tyramide signal amplification (TSA). In various embodiments, such substrates may be used, for example, to label targets in samples that are cells, tissues or arrays for their subsequent detection by microscopy, flow cytometry, optical scanning and fluorometry.

In some embodiments, when an enzyme reporter molecule is a phosphatase enzyme such as, by way of example only, an acid phosphatases or an alkaline phosphatase, suitable substrates include, but are not limited to, 5-bromo-6-chloro-3-indolyl phosphate (BCIP), 6-chloro-3-indolyl phosphate, 5-bromo-6-chloro-3-indolyl phosphate, p-nitrophenyl phosphate, and o-nitrophenyl phosphate. Nonlimiting fluorogenic substrates include, but are not limited to, 4-methylumbelliferyl phosphate, 6,8-difluoro-7-hydroxy-4-methylcoumarinyl phosphate (DiFMUP, U.S. Pat. No. 5,830,912), fluorescein diphosphate, 3-O-methylfluorescein phosphate, resorufin phosphate, 9H-(1,3-dichloro-9,9-dimethylacridin-2-one-7-yl)phosphate (DDAO phosphate), ELF 97, ELF 39, and related phosphates (U.S. Pat. Nos. 5,316,906 and 5,443,986).

In some embodiments, when an enzyme reporter molecule is a glycosidase such as, by way of example only, a beta-galactosidase, beta-glucuronidase, or beta-glucosidase, suitable substrates include, but are not limited to, 5-bromo-4-chloro-3-indolylbeta-D-galactopyranoside (X-gal) and similar indolyl galactosides, glucosides, and glucuronides, o-nitrophenyl beta-D-galactopyranoside (ONPG), p-nitrophenyl beta-D-galactopyranoside, resorufin beta-D-galactopyranoside, fluorescein digalactoside (FDG), fluorescein diglucuronide and their structural variants, 4-methylumbelliferyl beta-D-galactopyranoside, carboxyumbelliferyl beta-D-galactopyranoside, and fluorinated coumarin beta-D-galactopyranosides.

Enzyme reporter molecules also include, but are not limited to, hydrolases such as cholinesterases and peptidases, oxidases such as glucose oxidase and cytochrome oxidases, and reductases, for which suitable substrates are known. Additional nonlimiting exemplary enzyme reporter molecules include luciferases and aequorins. In addition, the chemiluminescence-producing substrates for phosphatases, glycosidases and oxidases such as those containing stable dioxetanes, luminol, isoluminol and acridinium esters can also be used with the enzyme reporter molecules described herein.

In some embodiments, a reporter molecule is a hapten. Nonlimiting exemplary haptens include hormones, naturally occurring and synthetic drugs, pollutants, allergens, affector molecules, growth factors, chemokines, cytokines, lymphokines, amino acids, peptides, chemical intermediates, nucleotides, biotin and the like. In some embodiments, a hapten is not directly detectable, but it can bind to another molecule that is detectable. As a nonlimiting example, a hapten may be an antigen that can be bound by an antibody specific to that antigen, wherein the antibody comprises a detectable label, or wherein the antibody can be bound by a secondary antibody comprising a detectable label.

In some embodiments, a reporter molecule is a fluorescent protein. Nonlimiting exemplary fluorescent proteins include green fluorescent protein (GFP) and the phycobiliproteins and derivatives thereof. In some embodiments, a fluorescent protein is used in conjunction with a fluorophore in order to obtain a larger stokes shift from the fluorescent protein's absorption spectra. In some embodiments, the fluorescent protein and fluorophore function as an energy transfer pair, wherein the fluorescent protein emits at the wavelength at which the fluorophore absorbs and the fluorophore then emits at a wavelength farther from the fluorescent protein's emission wavelength than could have been obtained with only the fluorescent protein. In some such embodiments, a compound of any one of Formulas (I) to (IV) comprises a fluorescent protein as one substituent and a fluorophore as another substituent. In some embodiments, a compound of any one of Formulas (I) to (IV) comprises both the fluorescent protein and the fluorophore as a single substituent, wherein the fluorescent protein and the fluorophore are connected to one another by a linker. Nonlimiting exemplary fluorescent protein/fluorophore pairs include phycobiliproteins and sulforhodamine fluorophores, sulfonated cyanine fluorophores, or sulfonated xanthene fluorophores. In some embodiments, the fluorophore functions as the energy donor and the fluorescent protein as the energy acceptor. Nonlimiting exemplary radioisotopes that may be used as reporter molecules include For example, the compounds may be radiolabeled with radioactive isotopes, such as for example tritium ($3H$), iodine-125 ($125I$) or carbon-14 ($14C$), sulfur-35 ($35S$), etc. All isotopic variations of the compounds of the present invention, whether radioactive or not, are intended to be encompassed within the scope of the present invention.

Methods of attaching reporter molecules as substituents of compounds of Formulas (I) to (IV) are known in the art. Nonlimiting exemplary methods include the molecule comprising an N-hydroxysuccinimidyl (NHS) ester is reacted with a precursor of a compound of any one of Formulas (I) to (IV) bearing a primary amine on at least one substituent. SDP esters, TFP, PFP, carbamates, thiocarbamates and maleimides may also be used in place of NHS esters.

Carrier Molecules

In some embodiments, a compound of any one of Formulas (I) to (IV) comprises a carrier molecule as a substituent.

Carrier molecules include, but are not limited to, antigens, steroids, vitamins, drugs, haptens, metabolites, toxins, environmental pollutants, amino acids, peptides, proteins, nucleic acids, nucleic acid polymers, carbohydrates, lipids, and polymers. In some embodiments, a carrier molecule comprises an amino acid, a peptide, a protein, an antibody or fragment thereof, an antigen, avidin, streptavidin, biotin, a dextran, an IgG binding protein (such as protein A or protein G), agarose, a polysaccharide, a nucleoside, a nucleotide, an oligonucleotide, a nucleic acid, a hapten, a psoralen, a drug, a hormone, a lipid, a lipid assembly, a synthetic polymer, a non-biological microparticle (such as a polymeric microparticle), an ion chelating moiety, an enzymatic substrate, a biological cell, a cellular component, a virus, or combinations thereof.

In some embodiments, when the carrier molecule is an enzymatic substrate, the enzymatic substrate is selected from an amino acid, a peptide, a sugar, an alcohol, alkanoic acid, 4-guanidinobenzoic acid, a nucleic acid, a lipid, sulfate, phosphate, —CH$_2$OCO-alkyl, and combinations thereof. In certain embodiments, such enzyme substrates can be cleaved by enzymes selected from peptidases, phosphatases, glycosidases, dealkylases, esterases, guanidinobenzotases, sulfatases, lipases, peroxidases, histone deacetylases, exonucleases, reductases, endoglycoceramidases and endonucleases.

In some embodiments, when the carrier molecule comprises an amino acid, a peptide, or protein, the carrier molecule is selected from a neuropeptide, a cytokine, a toxin, a protease substrate, and a protein kinase substrate. In some embodiments, a carrier is a peptide that functions as an organelle localization peptide, that is, a peptide that serves to target the conjugated compound for localization within a particular cellular substructure by cellular transport mechanisms, including, but not limited to, a nuclear localization signal sequence.

In some embodiments, a carrier molecule is a protein selected from an enzyme, an antibody, a lectin, a glycoprotein, a histone, an albumin, a lipoprotein, protein A, protein G, a phycobiliprotein or other fluorescent protein, a hormone, a toxin, and a growth factor. In some embodiments, a carrier molecule is a protein selected from an antibody, an antibody fragment, avidin, streptavidin, a toxin, a lectin, or a growth factor. In some embodiments, a carrier molecule comprises a hapten such as, for example, biotin, digoxigenin, or a fluorophore.

In some embodiments, a carrier molecule comprises a nucleic acid base, nucleoside, nucleotide or a nucleic acid polymer, a peptide nucleic acid (PNA), or a locked nucleic acid (LNA), single- or multi-stranded, natural or synthetic DNA or RNA oligonucleotide, or DNA/RNA hybrid, optionally containing an additional linker or spacer for attachment of a fluorophore or other ligand. In some embodiments, a nucleic acid carrier molecule (including, but not limited to, LNA, PNA, DNA, and RNA) comprises fewer than 50 nucleotides, or fewer than 25 nucleotides.

In some embodiments, a carrier molecule comprises a carbohydrate or polyol, including a polysaccharide, such as dextran, FICOLL, heparin, glycogen, amylopectin, mannan, inulin, starch, agarose and cellulose, or a polymer such as a poly(ethylene glycol). In some embodiments, a carrier molecule comprises dextran, agarose, or FICOLL.

In some embodiments, a carrier molecule comprises a lipid including, but not limited to, glycolipids, phospholipids, and sphingolipids. In some embodiments, such lipids contain 6-25 carbons. In some embodiments, a carrier molecule includes a lipid vesicle, such as a liposome, or is a lipoprotein. Some lipophilic substituents are useful, in some embodiments, for facilitating transport of a conjugated molecule into cells or cellular organelles.

In some embodiments, a carrier molecule is a cell, cellular fragment, or subcellular particle, including virus particles, bacterial particles, virus components, biological cells (such as animal cells, plant cells, bacteria, or yeast), or cellular components. Non-limiting examples of such cellular components include lysosomes, endosomes, cytoplasm, nuclei, histones, mitochondria, Golgi apparatus, endoplasmic reticulum and vacuoles.

In some embodiments, a carrier molecule comprises a specific binding pair member. In some such embodiments, the presence of the carrier molecule, and therefore the biomolecule to which it is conjugated through a compound of any one of Formulas (I) to (IV), can be detected using a complementary specific binding pair member comprising a detectable label. Nonlimiting exemplary binding pairs are set forth in Table 2.

TABLE 2

Exemplary Specific Binding Pairs

| Antigen | Antibody |
| --- | --- |
| Biotin | avidin (or streptavidin or anti-biotin) |
| IgG* | protein A or protein G |
| Drug | drug receptor |
| Folate | folate binding protein |
| Toxin | toxin receptor |
| Carbohydrate | lectin or carbohydrate receptor |
| Peptide | peptide receptor |
| Protein | protein receptor |
| enzyme substrate | Enzyme |
| DNA (RNA) | cDNA (cRNA)† |
| Hormone | hormone receptor |
| Ion | Chelator |

*IgG is an immunoglobulin
†cDNA and cRNA are the complementary strands used for hybridization In some embodiments, a carrier molecule is an antibody-binding moiety, such as, but not limited to, anti-Fc, an anti-Fc isotype, anti-J chain, anti-kappa light chain, anti-lambda light chain, or a single-chain fragment variable protein, an anti-Fc Fab fragment; or a non-antibody peptide or protein, such as, for example but not limited to, soluble Fc receptor, protein G, protein A, protein L, lectins, or a fragment thereof.

Methods of attaching carrier molecules as substituents of compounds of Formulas (I) to (V) are known in the art. Nonlimiting exemplary methods include as examples amides, thioamides, ethers, thioethers, carbamates, thiocarbamates, sulfhydryl groups, amino groups, etc.

Solid Supports

In some embodiments, a compound of any one of Formulas (I) to (IV) comprises a solid support as a substituent.

A large number of solid supports are known in the art and can be used, in some embodiments, as a substituent of a compound of any one of Formulas (I) to (IV). Nonlimiting exemplary solid supports include solid and semi-solid matrixes, such as aerogels and hydrogels, resins, beads, biochips (including thin film coated biochips), microfluidic chip, a silicon chip, multi-well plates (also referred to as microtiter plates or microplates), membranes, conducting and nonconducting metals, glass (including microscope slides) and magnetic supports. Other nonlimiting examples of solid supports include silica gels, polymeric membranes, particles, derivatized plastic films, derivatized glass, derivatized silica, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like. In some embodiments, the solid supports used in the methods and compositions described herein are substantially insoluble in liquid phases.

In some embodiments, a solid support may comprise a reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, azide, alkyne, or phosphine, wherein such functional groups are used to covalently attach the solid support to a precursor of a compound of any one of Formulas (I) to (IV).

A suitable solid phase support used in the methods and compositions described herein, can be selected on the basis of desired use. By way of example only, where amide bond formation is desirable to attach the precursor of a compound of any one of Formulas (I) to (IV) to the solid support, resins generally useful in peptide synthesis may be employed, such as polystyrene, POLYHIPE™ resin, polyamide resin, polystyrene resin grafted with polyethylene glycol, polydimethyl-acrylamide resin, or PEGA beads. In some embodiments, precursors to compounds of Formulas (I) to (IV) are deposited onto a solid support in an array format. In some such deposition is accomplished by direct surface contact between the support surface and a delivery mechanism, such as a pin or a capillary, or by ink jet technologies which utilize piezoelectric and other forms of propulsion to transfer liquids from miniature nozzles to solid surfaces.

Modified Biomolecules

The modification of biomolecules to incorporate chemical handles allows chemical attachment of another moiety (such as a reporter molecule or solid support) through a subsequent click reaction. In some embodiments, the chemical handle of the modified biomolecule is selected from azide, alkyne (such as a terminal alkyne or an activated alkyne), and phosphine. In some embodiments, a biomolecule is modified in vivo, for example, using cellular biosynthetic pathways, such as, for example, glycosylation of proteins, DNA replication, or transcription of RNA. In some embodiments, a biomolecule is modified in vivo by contacting a cell with a reagent that modifies a particular biomolecule or class of biomolecules. In some embodiments, a biomolecule is modified in vitro using a reagent that modifies a biomolecule.

Various methods and reagents for modifying biomolecules in vivo are known in the art. For example, in some embodiments, glycoproteins may be modified in vivo by contacting a cell with non-native glycans that comprise chemical handles. The non-native glycans are used by the cell to glycosylate glycoproteins, resulting in covalent attachment of chemical handles to such glycoproteins. Nonlimiting exemplary non-native glycans that may be used to modify glycoproteins with chemical handles include tetraacetylated N-azidoacetylglucosamine, tetraacetylated N-azidoacetylgalactosamine, tetraacetylated N-azidoacetylmannosamine, and tetraacetylfucose alkyne.

In some embodiments, a protein may be modified by incorporating non-native amino acids comprising chemical handles. Such modification may occur in vivo, during protein synthesis, or in an in vitro protein translation system. Nonlimiting exemplary non-native amino acids that may be used to modify proteins with chemical handles include, but are not limited to, 4-azido-L-phenylalanine, L-azidohomoalanine, and L-homopropargylglycine.

In some embodiments, a prenylated protein may be modified, for example, by contacting a cell with a farnesyl alcohol azide or a geranylgeranyl alcohol azide.

In some embodiments, a protein may be modified during fatty acid acylation of the protein, for example, by contacting a cell with a non-native fatty acid comprising a chemical handle. Nonlimiting exemplary non-native fatty acids that may be used to modify proteins with chemical handles include, but are not limited to, palmitic acid azide, myristic acid azide, and the fatty acid analogs described, e.g., in International Application No. PCT/US10/61768.

In some embodiments, DNA may be modified in vivo or in vitro using various non-native nucleoside triphosphates that comprise chemical handles. In some embodiments, the DNA is modified during replication through incorporation of a non-native nucleoside by DNA polymerase. In some embodiments, the DNA is modified during apoptosis through incorporation of a non-native nucleoside by terminal nucleotidyl transferase (TdT). Nonlimiting exemplary such non-native nucleoside triphosphates include C-8-alkyne-dUTP and/or C8-alkyne-dCTP. Following incorporation, the DNA comprises one or more covalently attached alkyne groups. In some embodiments, DNA may be modified during chemical DNA synthesis using, for example, phophoramidites comprising chemical handles.

In some embodiments, RNA may be modified in vivo or in vitro using various non-native nucleoside triphosphates that comprise chemical handles. In some embodiments, the RNA is modified during replication through incorporation of a non-native nucleoside by RNA polymerase. Nonlimiting exemplary such non-native nucleoside triphosphates include C-8-alkyne-UTP and/or C8-alkyne-CTP. Following incorporation, the RNA comprises one or more covalently attached alkyne groups. In some embodiments, RNA may be modified during chemical RNA synthesis using, for example, phophoramidites comprising chemical handles.

In some embodiments, a biomolecule may be modified in vitro using a reagent that covalently attaches a chemical handle through a particular group on the biomolecule. For example, in some embodiments, a biomolecule that comprises a primary amine (—NH2) may be modified using a reagent such as NHS-azide, NHS-phosphine, and sulfo-NHS-phosphine, SDP-azide, TFP-azide, PFP-azide, carbamate-azide, thiocarbamate-azide and maleimide-azide may also be used in place of NHS-azides.

Copper Ion Sources

In some embodiments, a click reaction comprises a copper ion source that provides Cu(I) ions. In some embodiments, a copper ion source provides Cu(I) ions in the presence of a reducing agent. In some such embodiments, a copper ion source provides Cu(II) ions, which are reduced to Cu(I) ions in the presence of a reducing agent. Nonlimiting exemplary copper ion sources that produce Cu(I) ions include CuBr, CuI, tetrakis(acetonitrile)Cu(I) hexafluorophosphate, tetrakis(acetonitrile)Cu(I) tetrafluoroborate, tetrakis(acetonitrile)Cu(I) triflate, CuCN, Cu(I) butanethiolate, Cu(I) thiophenolate, Cu(I) triflate. In some embodiments, a copper ion source that produces Cu(I) ions is included in a click reaction at a concentration between 0.01 mM and 10 mM, between 0.01 mM and 5 mM, between 0.05 mM and 5 mM, between 0.1 mM and 5 mM, between 0.5 mM and 5 mM, between 0.5 mM and 4 mM, or between 0.5 mM and 3 mM. Nonlimiting exemplary copper ion sources that produce Cu(II) ions include Cu(NO3)2 Cu(OAc)2 or CuSO4, metallic Cu and metallic Cu with sonication. In some embodiments, a copper ion source that produces Cu(II) ions is included in a click reaction at a concentration between 0.01 mM and 10 mM, between 0.01 mM and 5 mM, between 0.05 mM and 5 mM, between 0.1 mM and 5 mM, between 0.5 mM and 5 mM, between 0.5 mM and 4 mM, or between 0.5 mM and 3 mM.

In some embodiments, a copper ion source is copper-containing metal, such as copper wire. Nonlimiting exemplary reducing agents that may be used to reduce Cu(II) ions to Cu(I) ions include ascorbate, tris(2-carboxyethyl)phosphine (TCEP), NADH, NADPH, thiosulfate, metallic copper, hydroquinone, vitamin K1, glutathione, cysteine, 2-mercaptoethanol, and dithiothreitol. Nonlimiting exemplary metals that may act as reducing agents include Al, Be, Co, Cr, Fe (including Fe2+), Mg, Mn, Ni, Zn, Au, Ag, Hg, Cd, Zr, Ru, Fe, Co (including Co2+), Pt, Pd, Ni, Rh, and W. In some embodiments, a reducing agent is included in a click reaction at a concentration 1 micromolar to 5 molar.

In some embodiments, a reducing agent is an applied electric potential. In this case, a ligand such as TBTA, THPTA, benxzimidazole, BCS, etc is used employed and an electric potential of −30 to −300 mV is applied in a two compartment cell using a combination of working and reference electrodes. Standard buffers can be used (HEPES, Tris, etc) and the electric potential may be applied during the course of the reaction. See Chem Bio Chem 2008, 9, 1481-1486. for further details and experimental information.

Copper Ion Chelators

Without limitation to any specific mechanism, it is known that copper can promote the cleavage of biomolecules, such as proteins and nucleic acids. The addition of a copper chelator in a click reaction may reduce the detrimental effects of copper, thereby preserves the structural integrity of biomolecules.

In some embodiments, a click reaction comprises a copper chelator. In some embodiments, a copper chelator stabilizes Cu(I) ions against oxidation, precipitation, and/or disproportionation. By including a copper chelator, in some embodiments, a lower concentration of copper ions can be used in a click reaction to achieve the same efficiency as would be obtained in the presence of higher concentrations of copper ions in the absence of a chelator.

Nonlimiting exemplary copper ion chelators include compounds: THPTA, BTTAA, BTTP, BTTES, TBTA, N,N,N',N'-tetrakis(2-pyridylmethyl)ethylenediamine (TPEN), EDTA, neocuproine, N-(2-acetamido)iminodiacetic acid (ADA), pyridine-2,6-dicarboxylic acid (PDA), S-carboxymethyl-L-cysteine (SCMC), 1,10 phenanthroline, or a derivative thereof, trientine, glutathione, histidine, polyhistidine tetra-ethylenepolyamine (TEPA).

In others, the copper chelator is 1,10 phenanthroline, bathophenanthrolinedisulfonic acid (4,7-diphenyl-1,10-phenanthroline disulfonic acid), or bathocuproinedisulfonic acid (2,9-dimethyl-4,7-diphenyl-1,10-phenanthroline disulfonate).

In some embodiments, a copper chelator is included in a click reaction at molar ratio of 1:1, 2:1, 3:1, 4:1, 5:1, 6:1, 7:1, 8:1, 9:1, 10:1, or greater than 10:1, relative to the concentration of copper in the click reaction. That is, in some embodiments, if copper is included in a click reaction at a concentration of 2 mM, a copper chelator may be included in the click reaction at a concentration of 2 mM (1:1), 4 mM (2:1), 6 mM (3:1), etc. In some embodiments, the concentration of a copper chelator in a click reaction is between 1 µM and 100 mM, between 10 µM and 10 mM, between 50 µM and 10 mM, or between 1 mM and 10 mM.

Compositions

In some embodiments, compositions are provided. In some embodiments, a composition comprises a compound of any one of Formulas (I) to (IV). In some embodiments, a composition comprises a compound of any one of Formulas (I) to (IV) and a modified biomolecule. In some such embodiments, the compound of any one of Formulas (I) to (IV) comprises an azide and the biomolecule comprises an alkyne, such as a terminal alkyne or an activated alkyne, or a phosphine, such as a triarylphosphine. In some embodiments, the compound of any one of Formulas (I) to (IV) comprises an alkyne and the biomolecule comprises an azide.

In some embodiments, a composition comprises a first compound of any one of Formulas (I) to (IV) and a second compound of any one of Formulas (I) to (IV), wherein the first and second compounds of Formulas (I) to (IV) are distinguishable from one another. For example, in some embodiments, the first compound of any one of Formulas (I) to (IV) comprises a first reporter molecule and the second compound of any one of Formulas (I) to (IV) comprises a second reporter molecule, wherein the first and second reporter molecules are detectably different. In some embodiments, the first compound of any one of Formulas (II) to (IV) comprises an alkyne and the second compound of any one of Formulas (I) to (III) comprises an azide. In some such embodiments, the composition comprises a first biomolecule comprising an alkyne reactive group and a second biomolecule comprising an azide reactive group. In some embodiments, a composition comprises three, four, five, or more compounds of Formulas (I) to (IV). In some such embodiments, the compounds of Formulas (I) to (IV) in a composition can each be independently detected. That is, in some embodiments, two or more of the compounds comprise detectably different reporter molecules and/or can be separated from one another prior to detection, etc.

In some embodiments, a composition further comprises a copper ion source and/or a reducing agent and/or a copper ion chelator.

Various buffering agents can be included in the compositions described herein, including inorganic and organic buffering agents. In some embodiments buffering agent is a zwitterionic buffering agent. Exemplary buffering agents include phosphate (such as, for example, in phosphate buffered saline (PBS)), succinate, citrate, borate, maleate, cacodylate, N-(2-Acetamido)iminodiacetic acid (ADA), 2-(N-morpholino)-ethanesulfonic acid (IVIES, N-(2-acetamido)-2-aminoethanesulfonic acid (ACES), piperazine-N,N'-2-ethanesulfonic acid (PIPES), 2-(N-morpholino)-2-hydroxypropanesulfonic acid (MOPSO), N,N-bis-(hydroxyethyl)-2-aminoethanesulfonic acid (BES), 3-(N-morpholino)-propanesulfonic acid (MOPS), N-tris-(hydroxymethyl)-2-ethanesulfonic acid (TES), N-2-hydroxyethyl-piperazine-N-2-ethanesulfonic acid (HEPES), 3-(N-tris-(hydroxymethyl)methylamino)-2-hydroxypropanesulfonic acid (TAPSO), 3-(N,N-Bis[2-hydroxyethyl]amino)-2-hydroxypropanesulfonic acid (DIPSO), N-(2-Hydroxyethyl)piperazine-N'-(2-hydroxypropanesulfonic acid) (HEPPSO), 4-(2-Hydroxyethyl)-1-piperazinepropanesulfonic acid (EPPS), N-[Tris(hydroxymethyl)methyl]glycine (Tricine), N,N-Bis(2-hydroxyethyl)glycine (Bicine), (2-Hydroxy-1,1-bis(hydroxymethyl)ethyl)amino]-1-propanesulfonic acid (TAPS), N-(1,1-Dimethyl-2-hydroxyethyl)-3-amino-2-hydroxypropanesulfonic acid (AMPSO), tris (hydroxy methyl)amino-methane (Tris), TRIS-Acetate-EDTA (TAE), glycine, bis[2-hydroxyethyl]iminotris [hydroxymethyl]methane (BisTris), and combinations thereof. In some embodiments, a composition further comprises ethylene diamine tetraacetic acid (EDTA).

The concentration of such buffering agents in a composition, in some embodiments, is between 0.1 mM and 1 M, between 10 mM and 1 M, between 20 mM and 500 mM, between 50 mM and 300 mM, between 0.1 mM and 50 mM, and between 0.5 mM and 20 mM.

One skilled in the art can select a suitable composition pH according to the intended application. In order to retain the structural integrity of biomolecules, in some embodiments, the pH is maintained in a physiological range, such as, for example, between about 6.5 and 8. In some embodiments, a composition has a pH of between 5 and 9 at 25° C., between 6 and 8.5 at 25° C., between 6 and 8 at 25° C., between 6.5 and 8 at 25° C., or between 6.5 and 7.5 at 25° C.

In some embodiments, a composition comprises one or more non-ionic detergents. Non-limiting examples of such non-ionic detergents include polyoxyalkylene diols, ethers of fatty alcohols (such as alcohol ethoxylates), alkyl phenol ethoxylates, ethylene oxide/propylene oxide block copolymers, polyoxyethylene ester of a fatty acids, alkyl phenol surfactants, polyoxyethylene mercaptan analogs of alcohol ethoxylates, polyoxyethylene adducts of alkyl amines, polyoxyethylene alkyl amides, sorbitan esters, and alcohol phenol ethoxylate. Non-limiting examples of sorbitan esters include polyoxyethylene(20) sorbitan monolaurate (TWEEN20), polyoxyethylene(20) sorbitan monopalmitate (TWEEN40), polyoxyethylene(20) sorbitan monostearate (TWEEN60) and polyoxyethylene(20) sorbitan monooleate (TWEEN 80). In some embodiments, the concentration of such non-ionic detergents in a composition is between 0.005 and 0.5%, between 0.01 and 0.4%, between 0.01 and 0.3%, between 0.01 and 0.2%, or between 0.01 and 0.2%.

Conjugation of Modified Biomolecules

In various embodiments, the modified biomolecules described herein may be linked to at least one moiety selected from a reporter molecule, a carrier molecule, a solid phase, and a therapeutic molecule, by conjugating the modified biomolecule to a compound of any one of Formulas (I) to (IV) using a click reaction, a 1,3-dipolar cycloaddition reaction, or Staudinger ligation reaction. In some embodiments, the reaction is carried out at room temperature in aqueous solution.

In some embodiments, a click reaction is carried out in the presence of copper, such as Cu(I) ions. In some embodiments, a click reaction is carried out in the presence of a reducing agent. In some embodiments, the click reaction is carried out in the presence of a copper chelator. In some embodiments, the resulting conjugated product is stable in an aqueous environment for sufficient time to allow manipulation, quantification, and/or detection of the biomolecule.

In some embodiments, the click reaction, 1,3-dipolar cycloaddition reaction, or Staudinger ligation reaction is carried out in a cell, in a cell lysate, in a solution comprising an isolated modified biomolecule, or with a modified biomolecule immobilized on a solid support.

In some embodiments, a modified biomolecule comprises more than one type of chemical handle. As a nonlimiting example, in some embodiments, a modified biomolecule comprises an azide and an alkyne, such as a terminal alkyne or an activated alkyne. In some such embodiments, the modified biomolecule may be conjugated to a compound of any one of Formulas (I) to (IV) comprising a terminal alkyne and/or a compound of any one of Formulas (I) to (IV) comprising an azide, using click chemistry. In some embodiments, the modified biomolecule may be conjugated to a compound of any one of Formulas (I) to (IV) comprising an azide using click chemistry, and may be conjugated to another compound that comprises a phosphine using a Staudinger ligation or comprises an alkyne, such as a terminal alkyne or activated alkyne, using a 1,3-bipolar cycloaddition. Alternatively, in some embodiments, the modified biomolecule may be conjugated to a compound of any one of Formulas (I) to (IV) comprising a terminal alkyne, and may be conjugated to another compound that comprises an azide, both using click chemistry. Numerous combinations of chemical handles and conjugating reagents are possible, and can be selected according to the intended application by one skilled in the art.

Conjugation in a Cell

In some embodiments, methods of conjugating a modified biomolecule to a compound of any one of Formulas (I) to (IV) in a cell are provided. In some such embodiments, the conjugated biomolecule is separated from the cell following conjugation. In some embodiments, the conjugated biomolecule is identified, detected, and/or quantified in the cellular environment following conjugation (such as, for example, in the live cell, or in a cell that has been fixed and/or permeabilized prior to identification, detection and/or quantification of the biomolecule).

In some embodiments, a method of conjugating a modified biomolecule to a compound of any one of Formulas (I) to (IV) in a cell comprises contacting a cell comprising a modified biomolecule with a compound of any one of Formulas (I) to (IV) under conditions allowing the compound of any one of Formulas (I) to (IV) to come into contact with the modified biomolecule. In some embodiments, if the modified biomolecule is located on the surface of the cell, contacting the cell with a composition comprising the compound of any one of Formulas (I) to (IV) allows conjugation of the modified biomolecule. In some embodiments, when the modified biomolecule is located inside the cell, the cell may be contacted with a composition comprising the compound of any one of Formulas (I) to (IV) with or without prior fixing and/or permeabilization of the cell. In some embodiments, for example when the conjugation occurs via click reaction, the cell may also be contacted with a copper ion source, a reducing agent, and/or a copper ion chelator. Additional components, such as buffers, detergents, salts, and the like, can also be included in the conjugation reaction. One skilled in the art can select suitable additional components depending on the application.

The conjugation can be performed under aerobic or anaerobic conditions, such as under nitrogen or argon gas, and can be performed for any suitable length of time, such as, for example, from five minutes to six hours, from 10 minutes to 3 hours, from 20 minutes to 3 hours, or from 30 minutes to 2 hours. The reaction can be performed at a wide range of temperatures, for example, between 4° C. and 50° C., between 10° C. and 40° C., or between 15° C. and 30° C.

Cells may be fixed using any method, including, but not limited to treatment with 4% formaldehyde or methanol.

Cells may be permeabilized by any method, including but not limited to treatment with NP-40 buffer or 0.1% Triton buffer.

In some embodiments, a cell comprising more than one modified biomolecule is contacted with more than one compound of any one of Formulas (I) to (IV), wherein the compounds of Formulas (I) to (IV) are detectably different. In some such embodiments, the cell is contacted with two or more compounds of Formulas (I) to (IV) simultaneously or sequentially. Nonlimiting exemplary chemical handles that may be used in such multiplex reactions are described above.

Following conjugation, the conjugated biomolecules may be separated and/or detected according to methods known in the art. Exemplary such methods are discussed herein.

In some embodiments, a method of comprises:
  (a) contacting a cell comprising a modified biomolecule with a compound of any one of Formulas (I) to (IV) under conditions allowing conjugation of the modified biomolecule to the compound of formula compound of any one of Formulas (I) to (IV) to form a conjugated biomolecule; and
  (b) detecting the conjugated biomolecule.

Conjugation in Solution

In some embodiments, methods of conjugating a modified biomolecule to a compound of any one of Formulas (I) to (IV) in solution are provided. Such solutions include, but are not limited to, cell lysates, solutions of isolated biomolecules (in which the biomolecules are separated from at least some of the components of cells in which the biomolecules are ordinarily found), cell supernatants, liquid biological samples (described below), and the like.

In some embodiments, a method of conjugating a modified biomolecule to a compound of any one of Formulas (I) to (IV) in solution comprises contacting the modified biomolecule with a compound of any one of Formulas (I) to (IV) under conditions allowing the compound of any one of Formulas (I) to (IV) to react with the modified biomolecule via a click reaction, a 1,3-dipolar cycloaddition, or a Staudinger ligation. In some embodiments, for example when the conjugation occurs via click reaction, a copper ion source, a reducing agent, and/or a copper ion chelator may also be included in the solution. Additional components, such as buffers, detergents, salts, and the like, can also be included in the conjugation reaction. One skilled in the art can select suitable additional components depending on the application.

In some embodiments, more than one modified biomolecule is present in solution. In some such embodiments, more than one compound of any one of Formulas (I) to (IV) is also added to the solution and conjugated to the more that one modified biomolecules. In some embodiments, two or more compounds of Formulas (I) to (IV) are added to the solution sequentially or simultaneously. In some embodiments, the compounds of Formulas (I) to (IV) are detectably different. Nonlimiting exemplary chemical handles that may be used in such multiplex reactions are described above.

The conjugation can be performed under aerobic or anaerobic conditions, such as under nitrogen or argon gas, and can be performed for any suitable length of time, such as, for example, from five minutes to six hours, from 10 minutes to 3 hours, from 20 minutes to 3 hours, or from 30 minutes to 2 hours. The reaction can be performed at a wide range of temperatures, for example, between 4° C. and 50° C., between 10° C. and 40° C., or between 15° C. and 30° C.

Following conjugation, the conjugated biomolecules may be separated and/or detected according to methods known in the art. Exemplary such methods are discussed herein.

In some embodiments, a method of comprises:
(c) contacting a modified biomolecule with a compound of any one of Formulas (I) to (IV) under conditions allowing conjugation of the modified biomolecule to the compound of formula compound of any one of Formulas (I) to (IV) to form a conjugated biomolecule; and
(d) detecting the conjugated biomolecule.

In some embodiments, the modified biomolecule comprises an azide and the compound of any one of Formulas (I) to (IV) comprises a terminal alkyne. In some embodiments, the modified biomolecule comprises a terminal alkyne, an activated alkyne, or a phosphine, and the compound of any one of Formulas (I) to (IV) comprises an azide. In some embodiments, the method comprises separating the conjugated biomolecule. In some embodiments, the compound of any one of Formulas (I) to (IV) comprises a reporter molecule. In some embodiments, the compound of any one of Formulas (I) to (IV) comprises a fluorophore. In some embodiments, detecting comprises illuminating the conjugated biomolecule with an appropriate wavelength of light, such that the reporter molecule emits light, and observing the emitted light.

Conjugation on a Solid Support

In some embodiments, methods of conjugating a modified biomolecule to a compound of any one of Formulas (I) to (IV) on a solid support are provided. Nonlimiting exemplary such solid supports include the various solid supports discussed herein, including, but not limited to, solid and semi-solid matrixes, such as glass, slides, arrays, silica particles, polymeric particles, microtiter plates and polymeric gels. In some embodiments, the compound of any one of Formulas (I) to (IV) comprises a solid support as a substituent. In some embodiments, the modified biomolecule is bound to a solid support.

The modified biomolecule may be bound to a solid support through any means. For example, in some embodiments, the modified biomolecule may have been adsorbed onto a solid support through non-covalent interactions. In some embodiments, the modified biomolecule comprises a member of a binding pair, and is bound to a solid support that comprises the other member of the binding pair. In some embodiments, the modified biomolecule has been conjugated to a solid support through a prior reaction, which may be a click reaction, 1,3-dipolar cycloaddition, a Staudinger ligation, or other type of reaction. Thus, in some embodiments, the modified biomolecule is attached to a solid support using a functional group other than the chemical handle used for a click reaction, 1,3-dipolar cycloaddition, or Staudinger ligation, whereupon the attached modified biomolecule is then conjugated to a compound of any one of Formulas (I) to (IV) through the chemical handle in a click reaction, 1,3-dipolar cycloaddition, or Staudinger ligation. By way of example only, the modified biomolecule can be immobilized to a solid support using hydroxyl, carboxyl, amino, thiol, aldehyde, halogen, nitro, cyano, amido, urea, carbonate, carbamate, isocyanate, sulfone, sulfonate, sulfonamide or sulfoxide functional groups.

When conjugation of the biomolecule to a compound of any one of Formulas (I) to (IV) occurs on a solid support, in some embodiments, the reaction is carried out in a similar composition as is used for solution-phase conjugation.

In some embodiments, a method of comprises:
(e) contacting a modified biomolecule with a compound of any one of Formulas (I) to (IV) under conditions allowing conjugation of the modified biomolecule to the compound of formula compound of any one of Formulas (I) to (IV) to form a conjugated biomolecule, wherein the modified biomolecule or the compound of any one of Formulas (I) to (IV) is immobilized on a solid support; and
(f) detecting the conjugated biomolecule.

In some embodiments, the modified biomolecule comprises an azide and the compound of any one of Formulas (II) or (IV) comprises a terminal alkyne. In some embodiments, the modified biomolecule comprises a terminal alkyne, an activated alkyne, or a phosphine, and the compound of any one of Formulas (I) or (IV) comprises an azide. In some embodiments, the method comprises separating the conjugated biomolecule. In some embodiments, the compound of any one of Formulas (I) to (IV) comprises a reporter molecule. In some embodiments, the compound of any one of Formulas (I) to (IV) comprises a fluorophore. In some embodiments, detecting comprises illuminating the conjugated biomolecule with an appropriate wavelength of light, such that the reporter molecule emits light, and observing the emitted light.

Separation of Conjugated Biomolecules

In some embodiments, a conjugated biomolecule is separated following conjugation via a click reaction, a 1,3- dipolar cycloaddition, or a Staudinger ligation. Nonlimiting exemplary methods of separating conjugated biomolecules include sedimentation, centrifugation, magnetic attraction, chromatographic methods, and electrophoretic methods.

In some embodiments, separation of the conjugated biomolecule is facilitated by a substituent on a compound of any one of Formulas (I) to (IV) that has been conjugated to the biomolecule. As a nonlimiting example, the compound of any one of Formulas (I) to (IV) may comprise a member of a binding pair, which is then bound to the complementary member of the binding pair to separate the conjugated biomolecule. For example, in some embodiments, the compound of any one of Formulas (I) to (IV) comprises biotin such that the conjugated biomolecule may be separated by binding to a streptavidin-containing solid support, such as streptavidin-coated multiwell plates or streptavidin-coated microparticles. As a further non-limiting example, the compound of any one of Formulas (I) to (IV) may comprise a microparticle (including, for example, a magnetic microparticle) as a substituent, such that the conjugated biomolecule may be separated by centrifugation (or contact with a magnet if the microparticle is magnetic).

In some embodiments, conjugated biomolecules are separated by thin layer or column chromatography. Nonlimiting exemplary such chromatography includes size exclusion, ion exchange, and affinity chromatography. In some embodiments, conjugated biomolecules are separated using isoelectric focusing. In some embodiments, conjugated biomolecules are separated using electrophoresis. Nonlimiting exemplary electrophoresis includes gel electrophoresis (such as, for example, agarose gel electrophoresis and acrylamide gel electrophoresis), capillary electrophoresis, capillary gel electrophoresis, and slab gel electrophoresis. Gel electrophoresis can be denaturing or nondenaturing, and can include denaturing gel electrophoresis followed by nondenaturing gel electrophoresis (e.g., "2D" gels). The conjugated biomolecules may be detected at any time before, during, or after separation. In some embodiments, such as when the conjugated biomolecules are separated by gel electrophoresis, the conjugated biomolecules may be detected in the separation medium (e.g., the gel), either during or after separation.

One skilled in the art can select a suitable separation method according to the moieties conjugated to the conjugated biomolecule, the identity or type of biomolecule, and the particular application.

Detection of Conjugated Biomolecules

In some embodiments, the conjugated biomolecules are detected following conjugation. In some embodiments, a reporter molecule that is a substituent of a compound of any one of Formulas (I) to (IV) that has been conjugated to a biomolecule is used for detection. In some embodiments, a carrier molecule that is a substituent of a compound of any one of Formulas (I) to (IV) that has been conjugated to a biomolecule is used for detection. In some embodiments, a solid support that is a substituent of a compound of any one of Formulas (I) to (IV) that has been conjugated to a biomolecule is used for detection. The phrase "used for detection" encompasses direct or indirect detection of the reporter molecule, carrier molecule, or solid support. The conjugated biomolecules may be detected by any method. Many methods of detection are known in the art, and some non-limiting exemplary methods will be discussed below by way of illustration only. One skilled in the art can select a suitable detection method depending on the identity and/or properties of the reporter molecule, carrier molecule, solid support, biomolecule, and any other moieties associated therewith.

Detection of conjugated biomolecules may occur at any time following conjugation, and at any time before, during, or after separation, if such separation is carried out.

In some embodiments, the moieties used for detection are any fluorophores described herein that can be used as substituents on compounds of Formulas (I) to (IV). Non-limiting exemplary such fluorophores include fluoresceins, rhodamines, TAMRA, Alexa dyes, Cy Dyes, SYPRO dyes, and BODIPY dyes.

In some embodiments, a method comprises multiplexed detection of modified biomolecules, for example, by conjugating the modified biomolecules to compounds of Formulas (I) to (IV) comprising different reporter molecules. In some embodiments, the conjugation reaction can be carried out such that modified biomolecule comprising particular chemical handles are conjugated to compounds of Formulas (I) to (IV) comprising particular reporter molecules.

In some embodiments, in-gel fluorescence detection allows for quantitative differential analysis of biomolecules and is amenable to multiplexing with other protein gel stains. In some embodiments, utilizing fluorescent- and/or UV-excitable reporter molecules as substituents of compounds of Formulas (I) to (IV) allows for the multiplexed detection of biomolecules (such as, for example, glycoproteins, phosphoproteins, and total proteins) in the same 1-D or 2-D gels.

In some embodiments, detection of modified biomolecules (such as, for example, proteins) can be by Western blot, in which the modified biomolecules are separated by gel electrophoresis and transferred to a blotting membrane. The modified biomolecules may be conjugated on the blotting membrane to a compound of any one of Formulas (I) to (IV), and then detected. Alternatively, in some embodiments, modified biomolecules that have been previously conjugated to a compound of any one of Formulas (I) to (IV) can be separated by gel electrophoresis and transferred to a blotting membrane, and then detected.

Another potential aspect of "in gel" detection is the total detection of proteins in electrophoresis gels or Western blot membranes using a "universal" click chemistry, in which phenylboronic acid-containing molecules are tethered via a linker to an azide moiety or an alkyne moiety. The phenylboronic acid stably associates with the cis-diol moieties on glycoproteins under certain conditions. Such phenylboronic acid-containing molecules can be used, in some embodiments, to modify glycoproteins with either azide or alkyne moieties after electrophoretic separation. The azide or alkyne moieties can then be used to conjugate the glycoproteins to a compound of any one of Formulas (I) to (IV) comprising, for example, a reporter molecule, via click chemistry, activated alkyne chemistry, or Staudinger ligation. In some embodiments, the conjugated glycoproteins may then be detected, either directly or indirectly, using, for example, the reporter molecule. In some embodiments, glycoproteins of interest can then be isolated by excising portions of the gel comprising the modified glycoproteins, and the phenylboronic acid dissociated from the glycoproteins under acidic conditions, thereby releasing the conjugated compound of any one of Formulas (I) to (IV) from the glycoprotein. In some embodiments, the glycoprotein may then be identified using, for example, mass spectrometry.

In some embodiments, when detection comprises detecting an optical response, the conjugated biomolecules may be detected at any time by illumination with a wavelength of light that results in a detectable optical response, and observation with a means for detecting the optical response. In some embodiments, such illumination is by a violet or visible wavelength emission lamp, an arc lamp, a laser, or even sunlight or ordinary room light, wherein the wavelength of such sources overlap the absorption spectrum of the moiety being detected, such as a fluorophore or chromophore. In some embodiments, such illumination is by a violet or visible wavelength emission lamp, an arc lamp, a laser, or even sunlight or ordinary room light, wherein a fluorescent compound displays intense visible absorption as well as fluorescence emission.

In some embodiments, the illumination sources include, but are not limited to, hand-held ultraviolet lamps, mercury arc lamps, xenon lamps, argon lasers, laser diodes, blue laser diodes, and YAG lasers. These illumination sources are optionally integrated into laser scanners, flow cytometer, fluorescence microplate readers, standard or mini fluorometers, or chromatographic detectors. The fluorescence emission following illumination is optionally detected by visual inspection, or by use of any of the following devices: CCD cameras, video cameras, photographic film, laser scanning devices, fluorometers, photodiodes, photodiode arrays, quantum counters, epifluorescence microscopes, scanning microscopes, flow cytometers, fluorescence microplate readers, or by means for amplifying the signal such as photomultiplier tubes.

In some embodiments, for example, when a sample is examined using a flow cytometer, a fluorescence microscope, or a fluorometer, the instrument is optionally used to distinguish and/or discriminate between multiple fluorophores having detectably different optical properties. In some embodiments, when a sample is examined using a flow cytometer, examination of the sample optionally includes isolation of particles within the sample based on the fluorescence response by using a sorting device.

In certain embodiments, fluorescence is optionally quenched using either physical or chemical quenching agents.

Samples

The end user will determine the choice of the sample and the way in which the sample is prepared. Samples that can be used with the methods and compositions described herein include, but are not limited to, any biological derived material or aqueous solution that contains a modified biomolecule. In certain embodiments, a sample also includes material in which a modified biomolecule has been added. The sample that can be used with the methods and compositions described herein can be a biological fluid including, but not limited to, whole blood, plasma, serum, nasal secretions, sputum, saliva, urine, sweat, transdermal exudates, cerebrospinal fluid, or the like. In other embodiments, the sample are biological fluids that include tissue and cell culture medium wherein modified biomolecule of interest has been secreted into the medium. Cells used in such cultures include, but are not limited to, prokaryotic cells and eukaryotic cells that include primary cultures and immortalized cell lines. Such eukaryotic cells include, without limitation, ovary cells, epithelial cells, circulating immune cells, β cells, hepatocytes, and neurons. In certain embodiments, the sample may be whole organs, tissue or cells from an animal, including but not limited to, muscle, eye, skin, gonads, lymph nodes, heart, brain, lung, liver, kidney, spleen, thymus, pancreas, solid tumors, macrophages, mammary glands, mesothelium, and the like.

Kits

In some embodiments, kits are provided, wherein the kits comprise a compound of any one of Formulas (I) to (IV). In some embodiments, a kit further comprises a copper ion source. In some embodiments, a kit further comprises a reducing agent. In some embodiments, a kit further comprises a copper ion chelator. In some embodiments, a kit further comprises a reagent for modifying a biomolecule. Nonlimiting exemplary such copper ion sources, reducing agents, copper ion chelators, and reagents for modifying biomolecules are described herein.

In some embodiments, a kit further comprises a copper ion chelator.

A detailed description of the invention having been provided above, the following examples are given for the purpose of illustrating the invention and shall not be construed as being a limitation on the scope of the invention or claims.

EXAMPLES

Chemicals were purchased from Sigma-Aldrich, Alfa Aesar, TCI America, Fisher Scientific, Adesis Inc, Ak Scientific, Oakwood Chemicals, or Combi-Bloks unless specified otherwise. Analytical thin-layer chromatography was performed using 0.25 mm silica gel 60F254 plates and visualized with 254 nm UV light or with potassium permanganate staining. 1H NMR spectra were recorded on a Brucker 400 MHz. All samples were dissolved in $CDCl_3$, $CD_3OD$, $D_2O$, or d6-DMSO and chemical shifts (δ) are expressed in parts per million relative to TMS peak as an internal standard. Abbreviations are: s, singlet; d, doublet; t, triplet; q, quartet; m, multiplet; br, broad. Coupling constants (J) are reported in hertz (Hz). Mass spectra were recorded using electrospray ionization (ESI) on an Agilent 1956 mass spectrometer.

Example 1. Compound 1

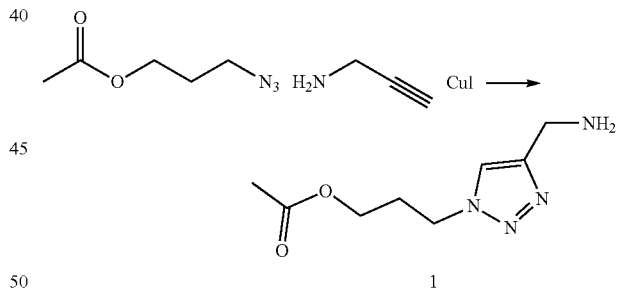

Copper(I) iodide (0.333 g, 1.746 mmol) was added to a solution of 3-azidopropyl acetate (5 g, 34.9 mmol, compound 1) and propargylamine (1.924 g, 34.9 mmol, compound 2) at r.t and the reaction mixture was stirred for ca. 30 min at r.t. According to TLC all azide was consumed, the reaction mixture was concentrated and the crude compound 1 was used without any further purification.

Example 2. Compound 2

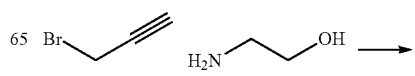

-continued

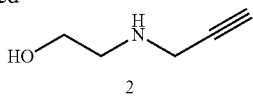

A solution of 2-aminoethanol (8.22 g, 134 mmol) in DCM (50 mL) was added to a solution of propargyl bromide (8 g, 67.2 mmol) at 4° C. over 10 min and the reaction mixture was stirred for 3 hours at 4° C. and was slowly warmed to r.t. over 30 min. The reaction mixture was concentrated and purified on 100 g of silica gel (DCM to 5% to 10%) to provide compound 2 as colorless oil.

Example 3. Compound 3

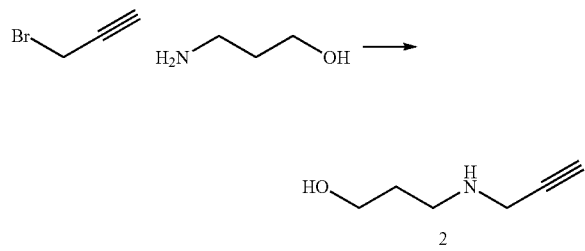

Compound 3 was prepared according to Example 3.

Example 4. Compound 4

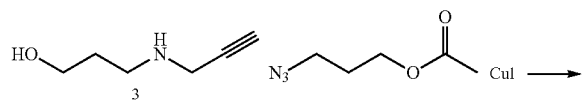

Copper(I) iodide (0.135 g, 0.707 mmol) was added to a solution of 3-(prop-2-yn-1-ylamino)propan-1-ol (1.6 g, 14.14 mmol, compound 9) and 3-azidopropyl acetate (2.93 g, 20.50 mmol, compound 1) at r.t and the reaction mixture was stirred for ca. 30 min at r.t. According to TLC all azide 1 was consumed, the reaction mixture was concentrated and the crude compound 4 was used without any further purification.

Example 5. Compound 5

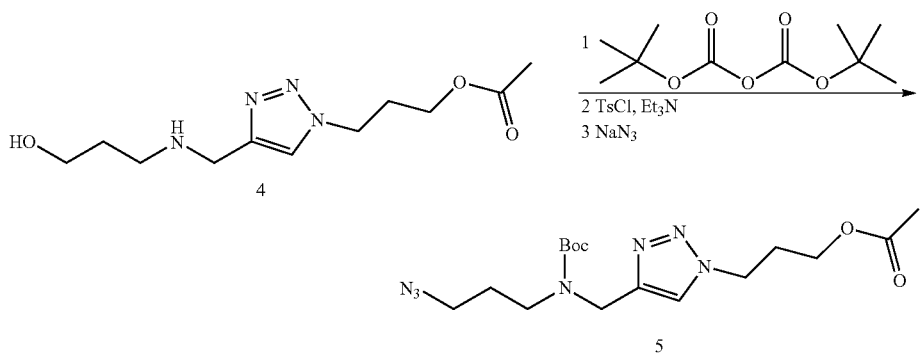

Di-tert-butyl dicarbonate (2.129 g, 9.75 mmol) was added to a solution of 3-(4-(((3-hydroxypropyl)amino)methyl)-1H-1,2,3-triazol-1-yl)propyl acetate (2 g, 7.80 mmol, compound 10) in MeOH 15 mL at r.t., and the reaction mixture was stirred overnight at r.t. According to TLC analysis compound 4 was consumed. Solvent was removed under reduced pressure and the crude re-dissolved in DCM, cooled to 4 C. Triethylamine (2.369 g, 23.41 mmol) was added followed by tosyl chloride (2.008 g, 10.53 mmol) and the reaction mixture was stirred for 12 hours at r.t. According to TLC analysis all intermediate was converted into tosylate. The crude material was transferred into separatory funnel, diluted with DCM (15 mL) washed with water, dried over sodium sulfate and the solvent was removed under reduced pressure. The crude was re-dissolved in DMF, sodium azide (0.685 g, 10.53 mmol) was added and the reaction mixture was stirred overnight at 60 C. Next day the solvent was removed under reduced pressure, and the crude was taken by EtOAc, washed with aqueous sodium bicarbonate, water, dried over sodium sulfate and solver was removed under reduced pressure. The crude was purified on silica gel (EtOAc:MeOH 100:1 to 10:1) to provide compound 5 as waxy solid.

Example 6. Compound 6

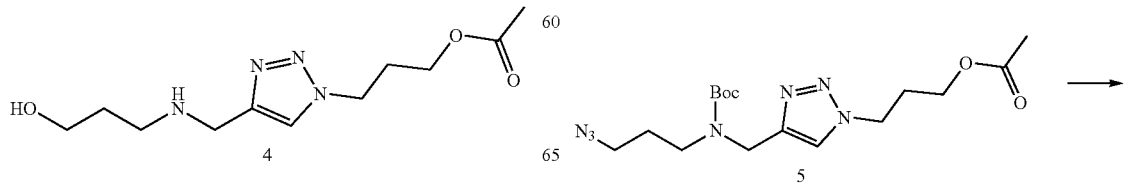

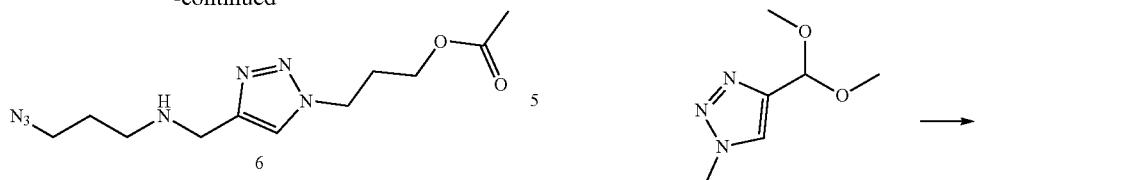

4 M HCl in dioxanes (5 mL) was added to a solution of compound 5 (1.69 g, 4.43 mmol) in dioxanes (5 mL) at 4 C and the reaction mixture was stirred for 30 minutes at 4 C. The solvent was removed under reduced pressure and the crude was purified on silica get (EtOAc:MeOH 25:1 to 5:1) to provide 398 mg of compound 6. MS (ESI, MH$^+$) 282.2

Example 7. Compound 7

Compound 7 was prepared according to Example 4-6. MS (ESI, MH$^+$) 268.1.

Example 8. Compound 9

Copper(I) iodide (2.16 g, 11.35 mmol) was added to a solution of oftert-butyl (3-azidopropyl)carbamate (50.0 g, 250 mmol) and propiolaldehyde diethyl acetal (29.1 g, 227 mmol) in DMF (150 mL) and the reaction mixture was stirred for 3 hours at r.t. According to GCMS and TCL analysis the reaction was complete. The solvent was removed under reduced pressure, and the crude tert-butyl (3-(4-(dimethoxymethyl)-1H-1,2,3-triazol-1-yl)propyl)carbamate was slowly crystallized at −20° C. overnight. The crude was washed with diethyl ether to provide 77 g of 8 as a grey solid that was used in the next step without any further purification.

A solution of 8 (10 g) was dissolved in DCM (150 mL) and a mixture of water (30 mL) and trifluoroacetic acid (30 mL) was added and the reaction mixture was stirred for 30 minutes at room temperature. According to TLC and GCMS analysis the reaction was completed. Saturated aqueous solution of sodium carbonate was added VERY CAREFULLY till pH>7. The organic layer was separated, washed with brine, and dried over anhydrous sodium sulfate. The solid was filtered off, and the solvent was removed under reduced pressure. The crude 9 was used in the next step without any further purification. $^1$H NMR (CDCl$_3$, 400 MHz) δ 10.15 (s, 1H), 8.30 (s, 1H), 4.87-4.79 (m, 1H), 4.52 (t, J=6.4 Hz, 2H), 3.18 (q, J=6.4 Hz, 2H), 2.15 (quint, J=6.4 Hz, 2H), 1.45 (s, 9H).

Example 8. Compound 10

A solution of crude 9 (1.0 g, 3.93 mmol) and 3-azidopropanamine (0.47 g, 4.72 mmol) in isopropanol (10 mL) was stirred for 30 minutes at 4° C. Sodium borohydrade (0.25 g, 6.67 mmol) was added at 4° C. in several small portions and the reaction mixture was stirred for an hour at 4° C., According to TLC and GCMS analysis the reaction was complete. The excess of sodium borohydride was carefully quenched with saturated aqueous solution of NaHCO$_3$ and the product was extracted with DCM (3×30 mL). The organic layer was dried over anhydrous sodium sulfate, the solid was filtered off, and the solvent was removed under reduced pressure. The crude was product was purified on silica gel (DCM:MeOH 0:100 to 85:15). MS (ESI, MH+) 339.2. $^1$H NMR (CDCl$_3$, 400 MHz) δ 7.55 (s, 1H), 4.81 (br.s, 1H), 4.41 (t, J=6.8 Hz, 2H), 3.90 (s. 2H), 3.39 (t. J=6.8 Hz, 2H), 3.14 (q, J=6.8 Hz, 2H), 2.76 (t, J=6.8 Hz, 2H), 2.08 (quint, J=6.8 Hz, 2H), 1.79 (quint, J=6.8 Hz, 2H), 1.45 (s, 9H).

Example 9. Compound 11

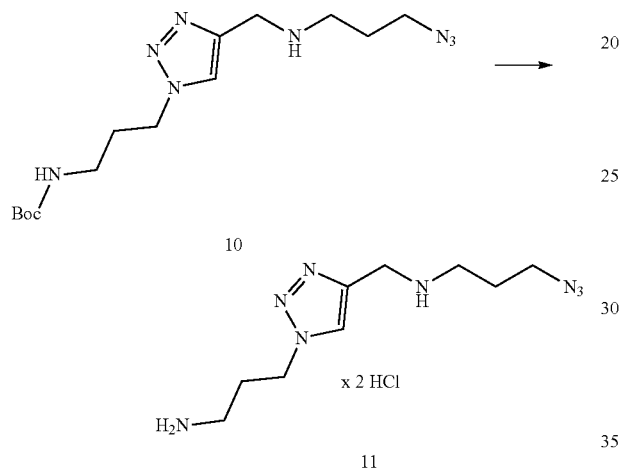

4M HCl in Dioxanes (50 mL) was added to a solution of 10 (3.14 g, 9.28 mmol) in dioxanes (10 mL) and the reaction mixture was stirred for 60 minutes at room temperature. Upon completion the reaction mixture was concentrated under reduced pressure and the crude was washed with diethyl ether and dried to provide 11 as white solid. $^1$H NMR (DMSO-d$_6$, 400 MHz) δ 9.68 (br.s, 2H), 8.38 (s, 1H), 8.34 (br.s, 3H), 4.57 (t, J=6.8 Hz, 2H), 4.28-4.21 (m, 2H), 3.50 (t, J=6.8 Hz, 2H), 3.03-2.92 (m, 2H), 2.80 (q, J=6.8 Hz, 2H), 2.20 (quint, J=6.8 Hz, 2H), 1.92 (quint, J=6.8 Hz, 2H).

Example 10. Compound 13

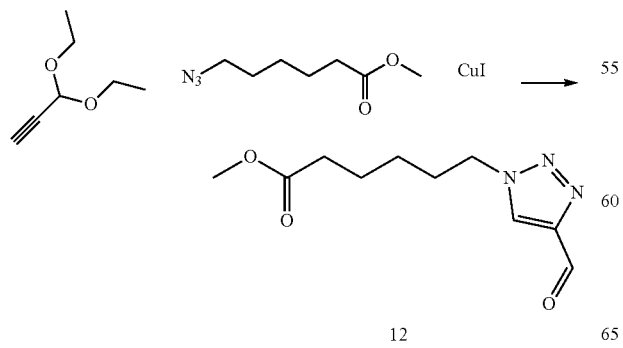

Copper(I) iodide (0.834 g, 4.38 mmol) was added to a solution of methyl 6-azidohexanoate (25.00 g, 146 mmol) and propiolaldehyde diethyl acetal (17.82 g, 146 mmol) in DMF (200 mL) and the reaction mixture was stirred overnight hours at ambient temperature. According to GCMS and TCL analysis methyl 6-azidohexanoate was completely consumed. The solvent was removed under reduced pressure, and the crude was re-dissolved in EtOAc (800 mL) and washed with 2×150 mL 0.5 M EDTA: saturated NaHCO$_3$1:1 (v:v), dried over anhydrous sodium sulfate. The solid was filtered off, and solvent was removed under reduced pressure. The crude diacetale re-dissolved in 600 mL of DCM and mixture of 30 mL of water and 15 mL of trifluoacetic acid was added. The reaction mixture was stirred for an hour. According to TLC analysis all intermediate diacetale was consumed. The reaction mixture quenched with saturated aqueous NaHCO$_3$, the organic layer was separated, washed with 2×150 mL of saturated aqueous NaHCO$_3$, dried over anhydrous sodium sulfate and concentrated under reduced pressure. The crude 12 was used without any further purification.

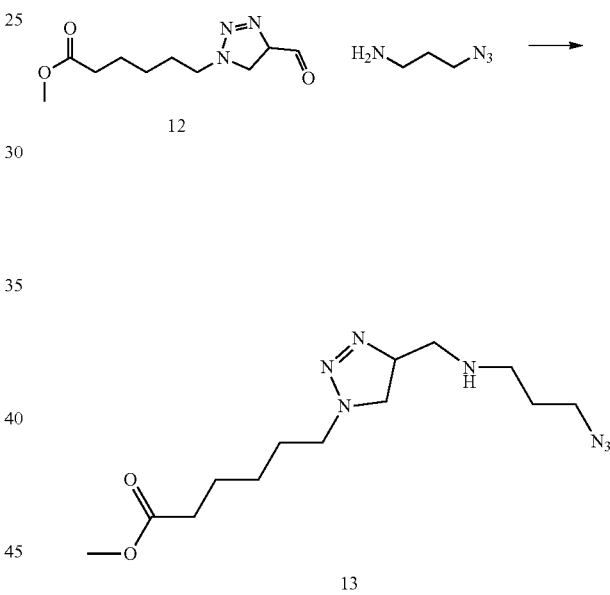

A solution of 12 (1.0 g, 4.44 mmol) and 3-azidopropanamine (0.58 g, 5.77 mmol) in isopropanol (10 mL) was stirred for 30 minutes at 4° C. Sodium borohydrade (0.25 g, 6.67 mmol) was added at 4° C. in several small portions and the reaction mixture was stirred for an hour at 4° C. According to TLC and GCMS analysis the reaction was complete. The excess of sodium borohydride was carefully quenched with saturated aqueous solution of NaHCO$_3$ and the product was extracted with DCM (3×30 mL). The organic layer was dried over anhydrous sodium sulfate, the solid was filtered off, and the solvent was removed under reduced pressure. The crude 13 was purified on silica gel (DCM:MeOH 0:100 to 80:10). MS (ESI, MH+) 310.3. $^1$H NMR (CDCl$_3$, 400 MHz) δ 7.45 (s, 1H), 4.34 (t, J=7.2 Hz, 2H), 3.90 (s, 2H), 3.66 (s, 3H), 3.38 (t, J=6.8 Hz, 2H), 2.77 (t, J=6.8 Hz, 2H), 2.31 (t, J=7.2 Hz, 2H), 1.92 (quint, J=7.2 Hz, 2H), 1.79 (quint, J=6.8 Hz, 2H), 1.67 (quint, J=7.2 Hz, 2H), 1.40-1.32 (m, 2H).

Example 11. Compound 15

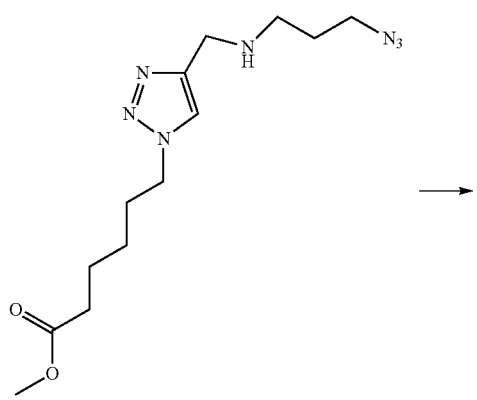

13

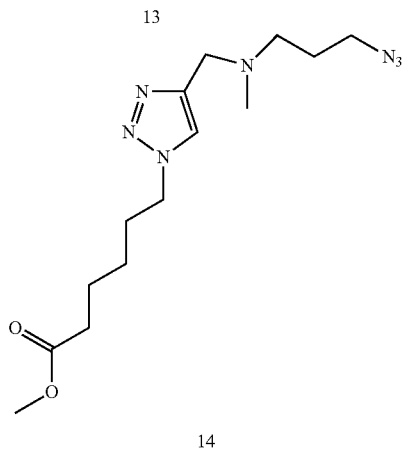

14

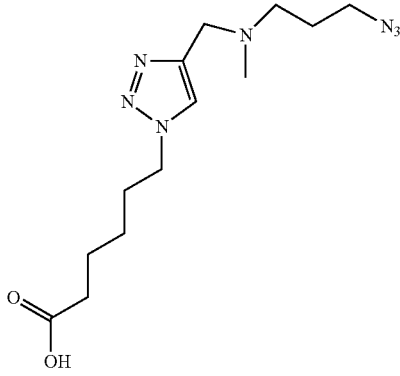

15

37% Aqueous formaldehyde (8.90 mL, 97 mmol) was added to a solution of 13 (1.5 g, 4.85 mmol) in acetonitrile (35 mL) and the reaction mixture was cooled to 4° C. Sodium cyanoborohydride (0.914 g, 14.55 mmol) was added at 4° C., ice-water bath was removed and the reaction mixture was stirred for 30 min. Glacial acetic acid was added dropwise until the solution tested neutral on wet pH paper. Stirring was continued for an additional 1 h, glacial acetic acid was added occasionally to maintain the pH near 7.5. Upon completion (TLC DCM/MeOH 10:1) a reaction mass was diluted with diethyl ether (60 mL) and carefully neutralized with aqueous solution of sodium carbonate until pH>8.5. Organic layer was separated and an aqueous layer was extracted with diethyl ether (2×30 mL). Combined organic extracts were dried over anhydrous sodium sulfate and solvents were removed under reduced pressure. The crude compound 14 was purified by flash chromatography silica gel (DCM/MeOH 100:0 to 90:10). MS (ESI, MH+) 324.2. $^1$H NMR (CDCl$_3$, 400 MHz) δ 7.46 (s, 1H), 4.35 (t, J=7.2 Hz, 2H), 3.69 (s, 2H), 3.67 (s, 3H), 3.34 (t, J=6.8 Hz, 2H), 2.48 (t, J=6.8 Hz, 2H), 2.32 (t, J=7.2 Hz, 2H), 2.25 (s, 3H), 1.93 (quint, J=7.2 Hz, 2H), 1.79 (quint, J=6.8 Hz, 2H), 1.67 (quint, J=7.2 Hz, 2H), 1.40-1.32 (m, 2H) ppm. A solution of lithium hydroxide hydrate (0.36 g, 8.66 mmol) in water (10 mL) was added to a solution of compound 14 at room temperature and the reaction mixture was stirred for 20-30 min. According to TLC analysis 14 was completely consumed, the reaction mixture neutralized by acetic acid (pH 4), and the solvent was removed under reduced pressure. The crude product was purified by C18 flash chromatography to provide 15 as colorless oil. $^1$H NMR (DMSO-d$_6$, 400 MHz) δ 7.97 (s, 1H), 4.31 (t, J=7.2 Hz, 2H), 3.57 (s, 2H), 3.34 (t, J=6.8 Hz, 2H), 2.34 (t, J=6.8 Hz, 2H), 2.15 (t, J=7.2 Hz, 2H), 2.12 (s, 3H), 1.80 (quint, J=7.2 Hz, 2H), 1.69 (quint, J=6.8 Hz, 2H), 1.50 (quint, J=7.2 Hz, 2H), 1.25-1.17 (m, 2H).

Example 12. Compound 16

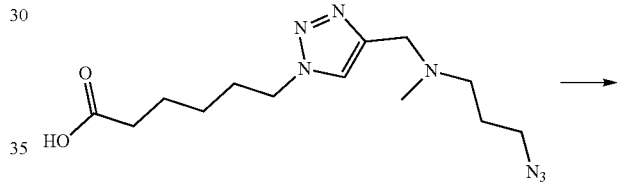

15

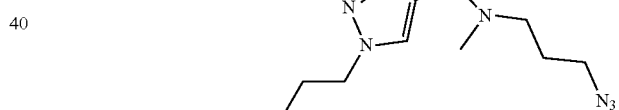

16

Example 13. Compound 18

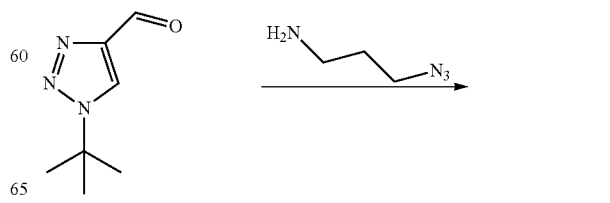

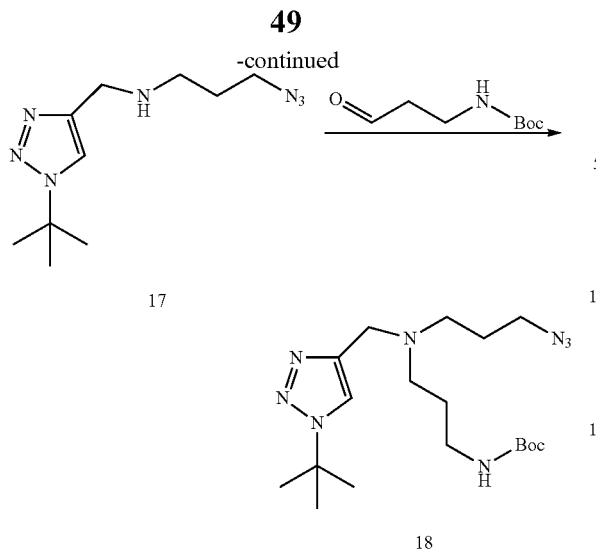

17

A solution of 1-(tert-butyl)-1H-1,2,3-triazole-4-carbaldehyde (1 g, 6.53 mmol) and 3-azidopropanamine (0.85 g, 8.49 mmol) in 2-propanol (10 mL) was stirred for 30 minutes at 4° C. Sodium borohydride (0.37 g, 9.79 mmol) was added to the reaction mixture at 4° C. in several portions and the resulting suspension was stirred at 4° C. for 60 minutes. According to TLC and GCMS analysis the reaction was complete. The excess of sodium borohydride was carefully quenched with saturated aqueous solution of NaHCO$_3$ and the product was extracted with DCM (3×30 mL). The organic layer was dried over anhydrous sodium sulfate, the solid was filtered off, and the solvent was removed under reduced pressure. The crude 17 was purified on silica gel (DCM:MeOH 0:100 to 90:10). $^1$H NMR (CDCl$_3$, 400 MHz) δ 7.53 (s, 1H), 3.89 (s, 2H), 3.39 (t, J=6.8 Hz, 2H), 2.77 (t, J=6.8 Hz, 2H), 1.80 (quint, J=6.8 Hz, 2H), 1.67 (s, 9H).

A solution of tert-butyl (3-oxopropyl)carbamate (0.5 g, 2.89 mmol) and 17 (0.53 g, 2.22 mmol) in DCM (20 mL) was stirred for 60 minutes at 4° C. Triacetoxy Borohydride (1.41 g, 6.66 mmol) was added to the reaction mixture at 4° C. in several portions and the resulting suspension was stirred at 4° C. for 60 minutes. According to TLC and GCMS analysis the reaction was complete. The excess of sodium borohydride was carefully quenched with saturated aqueous solution of NaHCO$_3$ and the product was extracted with DCM (3×50 mL). The organic layer was dried over anhydrous sodium sulfate, the solid was filtered off, and the solvent was removed under reduced pressure. The crude 18 was product was purified on silica gel (DCM:MeOH 0:100 to 95:5). MS (ESI, MH+) 395.1.

Example 14. Compound 19

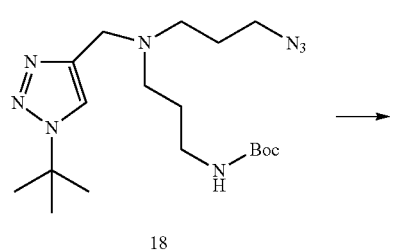

18

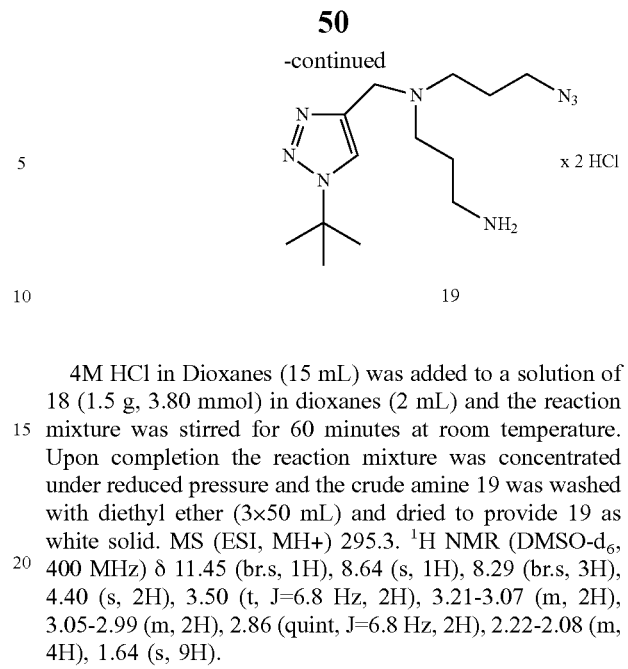

4M HCl in Dioxanes (15 mL) was added to a solution of 18 (1.5 g, 3.80 mmol) in dioxanes (2 mL) and the reaction mixture was stirred for 60 minutes at room temperature. Upon completion the reaction mixture was concentrated under reduced pressure and the crude amine 19 was washed with diethyl ether (3×50 mL) and dried to provide 19 as white solid. MS (ESI, MH+) 295.3. $^1$H NMR (DMSO-d$_6$, 400 MHz) δ 11.45 (br.s, 1H), 8.64 (s, 1H), 8.29 (br.s, 3H), 4.40 (s, 2H), 3.50 (t, J=6.8 Hz, 2H), 3.21-3.07 (m, 2H), 3.05-2.99 (m, 2H), 2.86 (quint, J=6.8 Hz, 2H), 2.22-2.08 (m, 4H), 1.64 (s, 9H).

Example 15. Compound 20

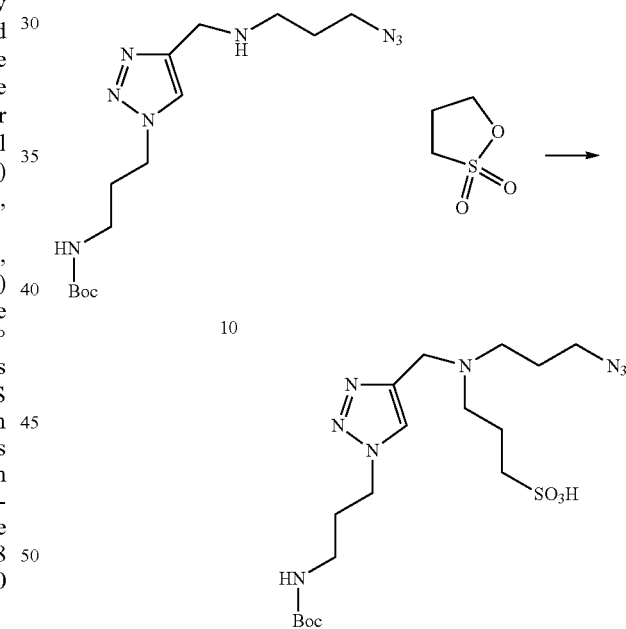

A solution of 10 (1 g, 2.95 mmol) and 1,3-propanesultone (0.38 g, 3.10 mmol) in acetonitrile (25 mL) was refluxed overnight. The reaction mixture was cooled to room temperature and solvent was removed under reduced pressure to provide crude 20 as an oil. The crude was purified on silica gel (DCM:MeOH 0:100 to 60:40). MS (ESI, 2MH+) 921. $^1$H NMR (DMSO-d$_6$, 400 MHz) δ 10.29 (br.s, 1H), 8.34 (s, 1H), 6.96 (t, J=5.4 Hz, 1H), 4.61-4.27 (m, 2H), 4.40 (t, J=6.8 Hz, 2H), 3.43 (t, J=6.8 Hz, 2H), 3.30-2.98 (m, 4H), 2.92 (q, J=6.4 Hz, 2H), 2.72-2.55 (m, 2H), 2.10-1.83 (m, 4H), 1.94 (quint, J=6.8 Hz, 2H), 1.38 (s, 9H).

Example 16. Compound 22

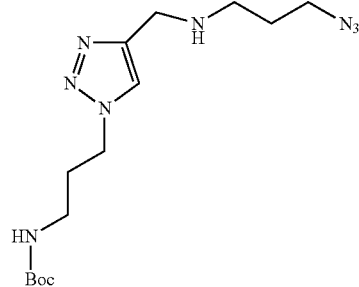

10

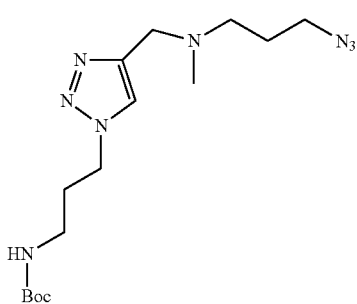

21

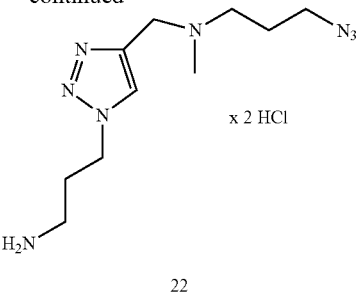

22

37% Aqueous formaldehyde (5.43 mL) was added to a solution of 10 (1.0 g, 2.95 mmol) in acetonitrile (25 mL) and the reaction mixture was cooled to 4° C. Sodium cyanoborohydride (0.56 g, 8.86 mmol) was added at 4° C., ice-water bath was removed, and the reaction mixture was stirred for 30 min. Glacial acetic acid was added dropwise until the solution tested neutral on wet pH paper. Stirring was continued for an additional 1 h, glacial acetic acid was added occasionally to maintain the pH near 7.5. Upon completion (TLC DCM/MeOH 10:1) solvent was removed under reduced pressure, and diethyl ether (60 mL) added followed by 40 mL of 2 M KOH. Organic layer was separated and an aqueous layer was extracted with diethyl ether (4×40 mL). Combined organic extracts were dried over anhydrous sodium sulfate and solvents were removed under reduced pressure. The crude 21 was purified by flash chromatography silica gel (DCM/MeOH 100:0 to 90:10). MS (ESI, MH+) 353.6. $^1$H NMR (CDCl$_3$, 400 MHz) δ 7.54 (s, 1H), 4.80 (br.s, 1H), 4.41 (t, J=6.8 Hz, 2H), 3.69 (s, 2H), 3.34 (t, J=6.8 Hz, 2H), 3.14 (q, J=6.4 Hz, 2H), 2.48 (t, J=6.8 Hz, 2H), 2.25 (s, 3H), 2.09 (quint, J=6.4 Hz, 2H), 1.79 (quint, J=6.8 Hz, 2H), 1.45 (s, 9H). Compound 22 was prepared according to Example 9.

Example 17. Compound 23

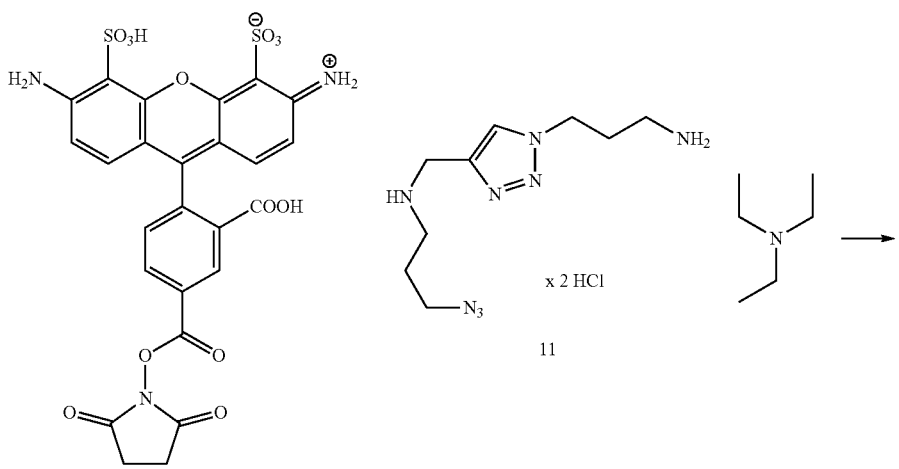

11

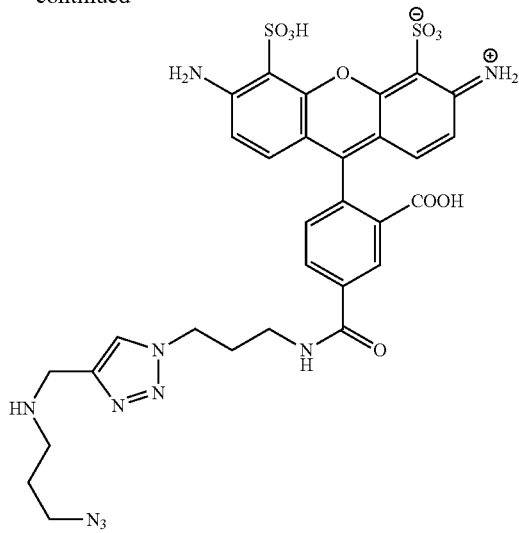

23

A solution of Compound 11 (83 mg) and triethylamine (0.353 mg, 0.504 mL, 3.48 mmol) in DMF (3 mL) was added to a solution of AFDye 488 NHS (Click Chemistry Tools, 0.22 g, 0.348 mmol) in DMF (5 mL). The reaction mixture was stirred for 30 mn at ambient temperature. According to HPLC analysis all AFDye 488 NHS ester was consumed. The reaction mixture was concentrated, and the crude purified in prepHPLC column (C-18, 21.2×250 mm, 35 mL/min, Water/MeOH 0-20% gradient over 30 min). MS (ESI): MH+=755.2 (positive mode).

Example 18. Compound 24

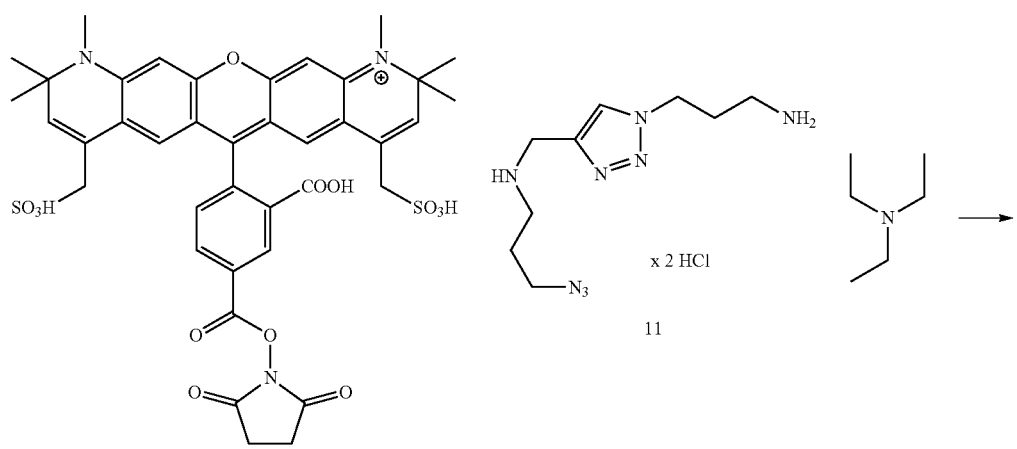

11

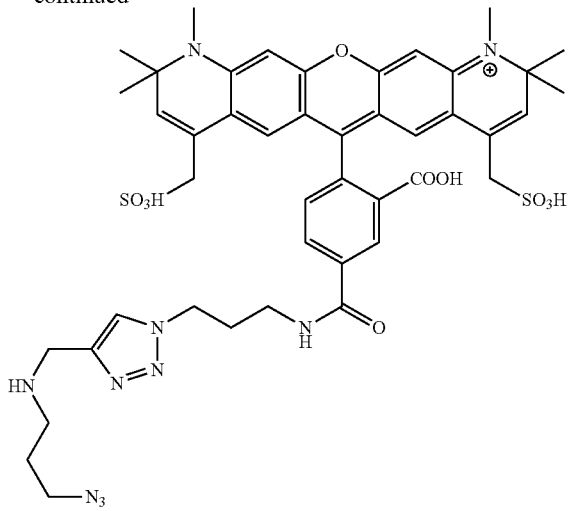

24

A solution of 11 (140 mg) and triethylamine (0.595 mg, 0.849 mL, 5.87 mmol) in DMF (3 mL) was added to a solution of AFDye 594 NHS (Click Chemistry Tools, 0.482 g, 0.587 mmol) in DMF (5 mL). The reaction mixture was stirred for 30 mn at ambient temperature. According to HPLC analysis all AFDye 594 NHS ester was consumed. The reaction mixture was concentrated, and the crude purified in prepHPLC column (C-18, 21.2×250 mm, 35 mL/min, Water/MeOH 10-75% gradient over 30 min). MS (ESI): MH+=943.3 (positive mode).

Example 19. Compounds 25-31

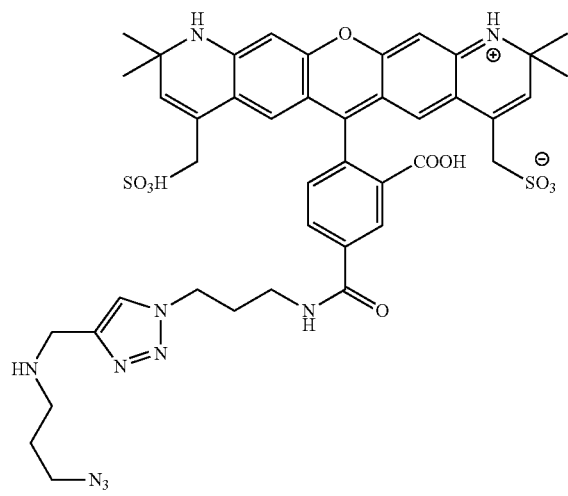

25

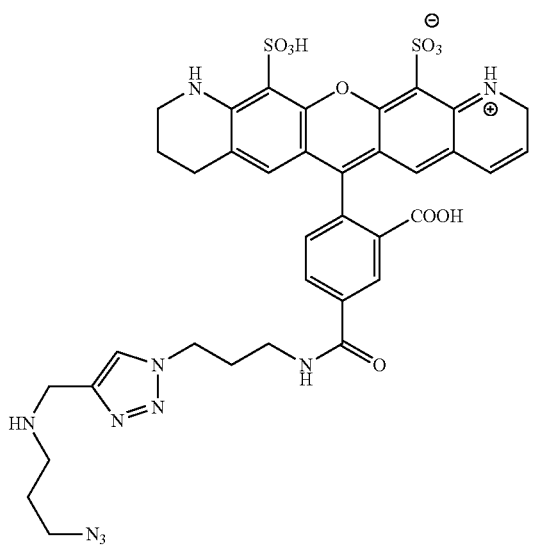

26

-continued
27
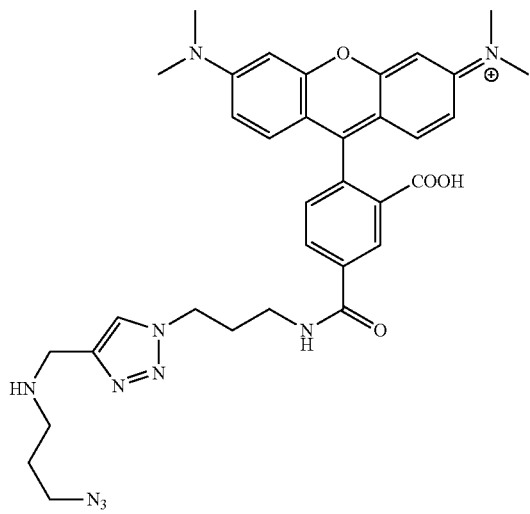
28
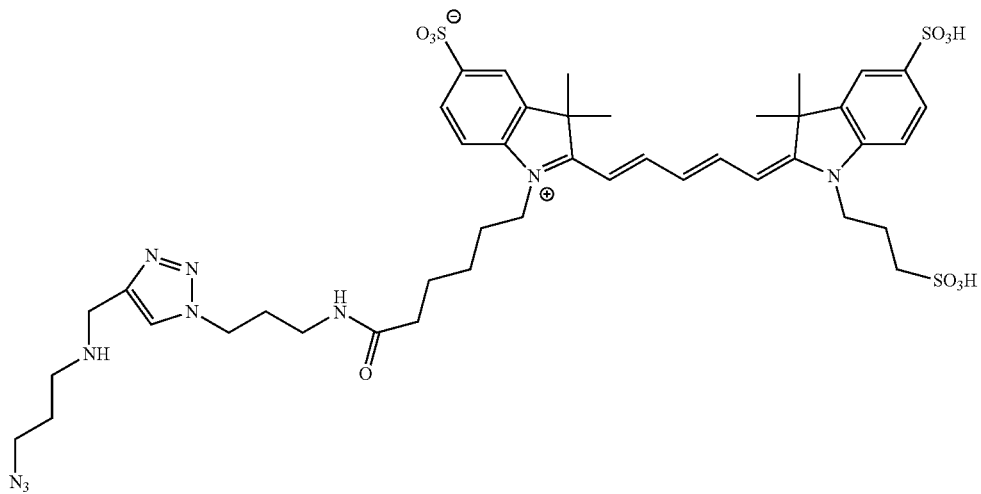
29
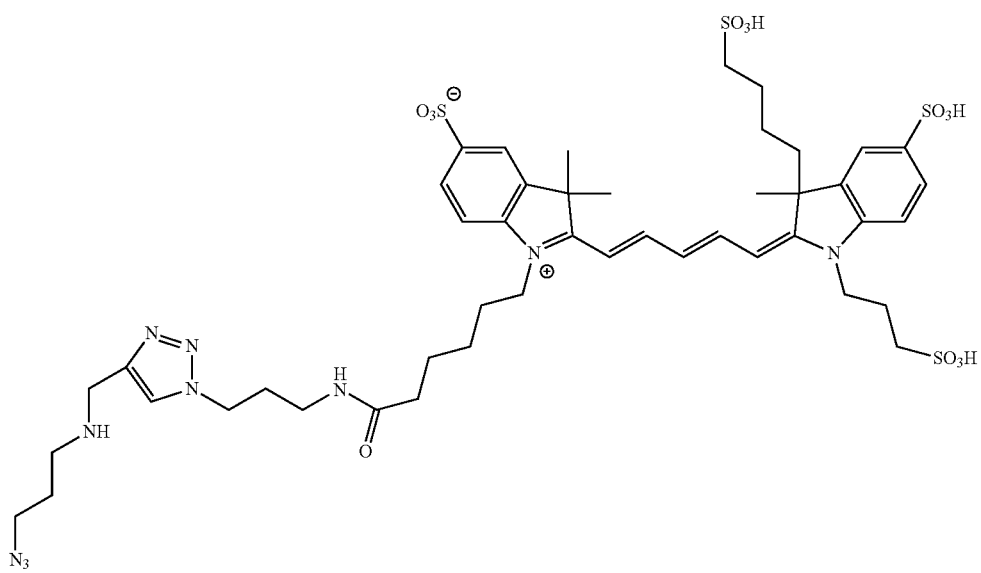

-continued
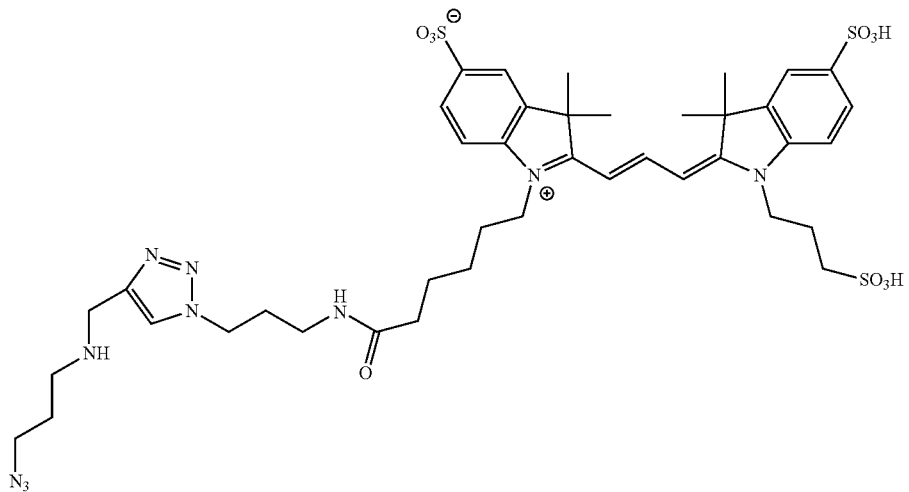
30
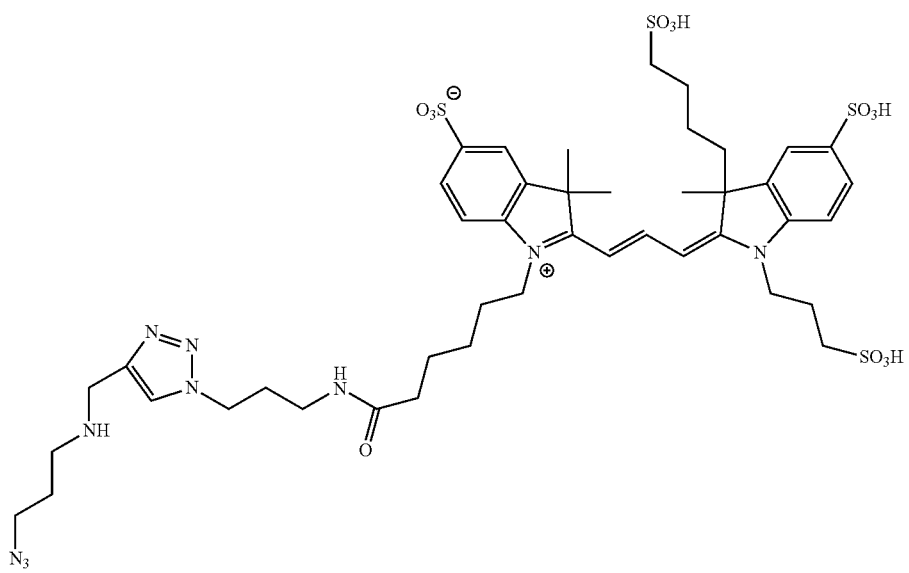
31
Compounds 25-31 were prepared according to Examples 18 using corresponding activated ester and compound 11.
Example 20. Compound 36
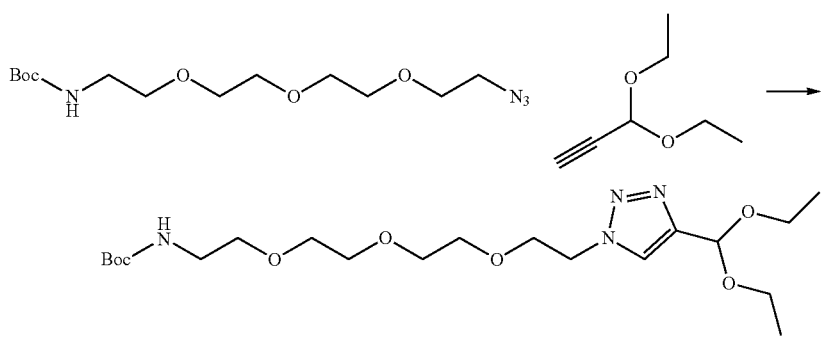
32

Copper(I) iodide (0.68 g, 3.57 mmol) was added to a solution of methyl tert-butyl (2-(2-(2-(2-azidoethoxy)ethoxy)ethoxy)ethyl)carbamate (25.00 g, 79 mmol) and propiolaldehyde diethyl acetal (9.15 g, 71.4 mmol) in DMF (75 mL) and the reaction mixture was stirred overnight at ambient temperature. According to TLC analysis azide was completely consumed. The solvent was removed under reduced pressure, and the crude 32 was used in the next step without any further purification.

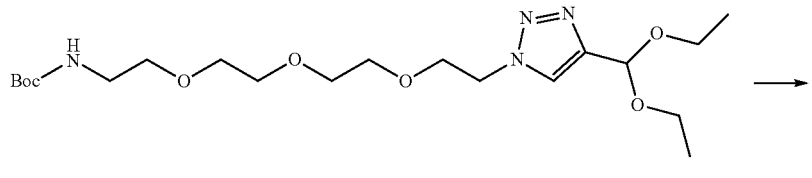

32

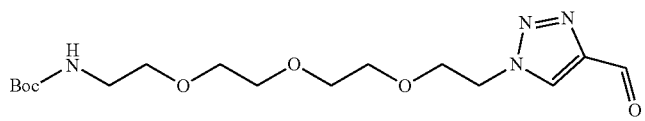

33

The crude diacetale 32 was dissolved in 600 mL of DCM and mixture of 30 mL of water and 15 mL of trifluoacetic acid was added. The reaction mixture was stirred for an hour. According to TLC analysis all diacetale 32 was consumed. The reaction mixture quenched with saturated aqueous NaHCO₃, the organic layer was separated, washed with 2×150 mL of saturated aqueous NaHCO₃, 0.5 M EDTA, dried over anhydrous sodium sulfate and concentrated under reduced pressure. The crude was used without any further purification. ¹H NMR (CDCl₃, 400 MHz) δ 10.15 (s, 1H), 8.40 (s, 1H), 5.03 (br.s, 1H), 4.64 (t, J=4.8 Hz, 2H), 3.91 (t, J=4.8 Hz, 2H), 3.67-3.52 (m, 11H), 3.34-3.26 (m, 2H), 1.43 (s, 9H).

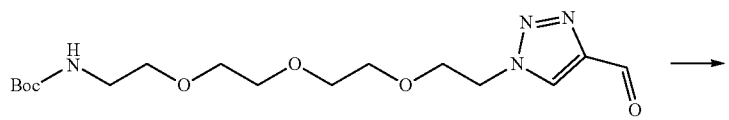

33

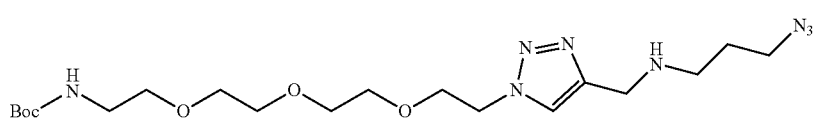

34

A solution of 33 (7 g, 18.80 mmol) and 3-azidopropanamine (2.44 g, 24.4 mmol) in 2-propanol (50 mL) was stirred for 30 minutes at 4° C. Sodium borohydride (1.07 g, 28.2 mmol) was added to the reaction mixture at 4° C. in several portions and the resulting suspension was stirred at 4° C. for 60 minutes. According to TLC analysis the reaction was complete. The excess of sodium borohydride was carefully quenched with saturated aqueous solution of NaHCO$_3$ and the product was extracted with DCM (2×150 mL). The organic layer was dried over anhydrous sodium sulfate, the solid was filtered off, and the solvent was removed under reduced pressure. The crude 34 was purified on silica gel (DCM:MeOH 0:100 to 85:15). $^1$H NMR (CDCl$_3$, 400 MHz) δ 7.66 (s, 1H), 5.17 (br.s, 1H), 4.54 (t, J=5.2 Hz, 2H), 3.90 (s, 2H), 3.88 (t, J=5.2 Hz, 2H), 3.61 (d, J=3.6 Hz, 8H), 3.54 (t, J=5.2 Hz, 2H), 3.38 (t, J=6.8 Hz, 2H), 3.31 (q, J=5.2 Hz, 2H), 2.76 (t, J=6.8 Hz, 2H), 1.79 (quint, J=6.8 Hz, 2H), 1.44 (s, 9H).

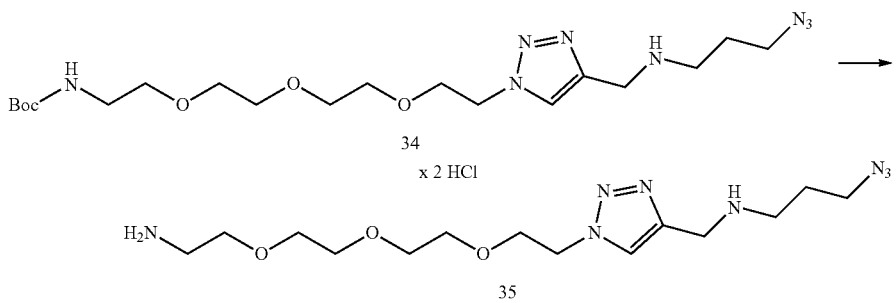

6M HCl in Dioxanes (40 mL) was added to a solution of 34 (3.5 g, 7.67 mmol) in dioxanes (10 mL) and the reaction mixture was stirred for 60 minutes at room temperature. Upon completion the reaction mixture was concentrated under reduced pressure and the crude product was washed with diethyl ether (3×50 mL) and dried to provide 35 as a colorless oil.

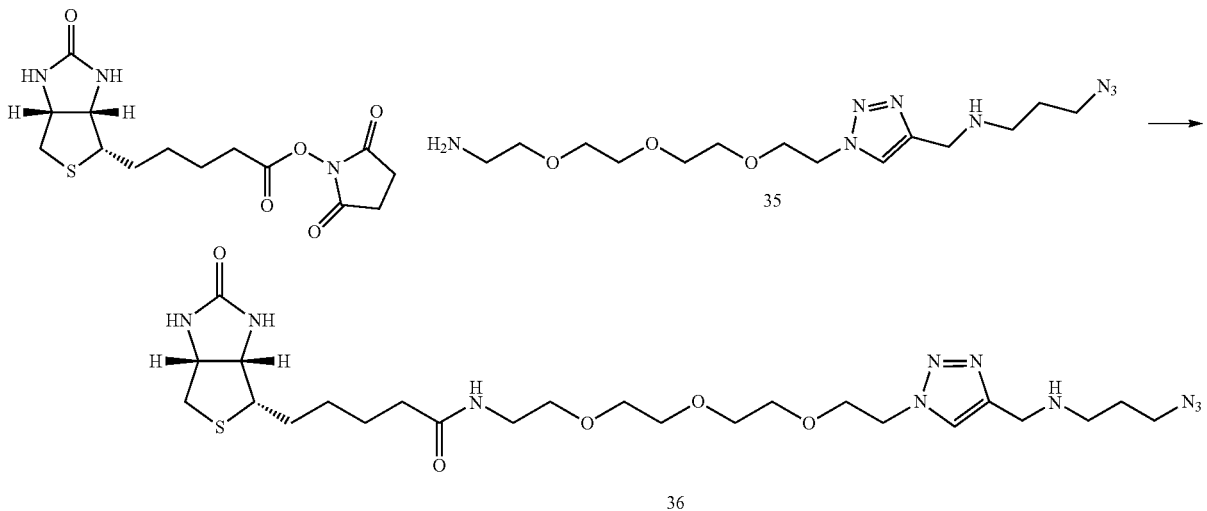

A solution of Biotin NHS Ester (2.36 g, 6.91 mmol), 35 (3.28 g, 7.68 mmol) and triethylamine (4.66 g, 46.1 mmol) in DMF (30 mL) was stirred for 30 mn at ambient temperature. According to HPLC analysis the reaction was complete. The reaction mixture was concentrated. The crude was product was purified on silica gel (DCM:MeOH 0:100 to 60:40) to provide 36 as amorphous solid. MS (ESI): MH+=. $^1$H NMR (DMSO-d$_6$, 400 MHz) δ 8.10 (s, 1H), 7.87 (t, J=5.6 Hz, 1H), 7.30 (br.s, 1H), 6.43 (s, 1H), 6.38 (s, 1H), 4.54 (t, J=5.2 Hz, 2H), 4.32-4.29 (m, 1H), 4.14-4.11 (m, 1H), 4.00 (s, 2H), 3.81 (t, J=5.2 Hz, 2H), 3.54-3.46 (m, 8H), 3.44 (t, J=6.8 Hz, 2H), 3.38 (t, J=6.4 Hz, 2H), 3.20-3.15 (m, 3H), 3.12-3.07 (m, 1H), 2.84-2.77 (m, 3H), 2.58 (d, J=12.4 Hz, 1H), 2.06 (t, J=7.2 Hz, 2H), 1.80 (quint, J=7.2 Hz, 2H), 1.65-1.57 (m, 1H), 1.54-1.41 (m, 3H), 1.35-1.25 (m, 2H).

Example 21. Compound 38

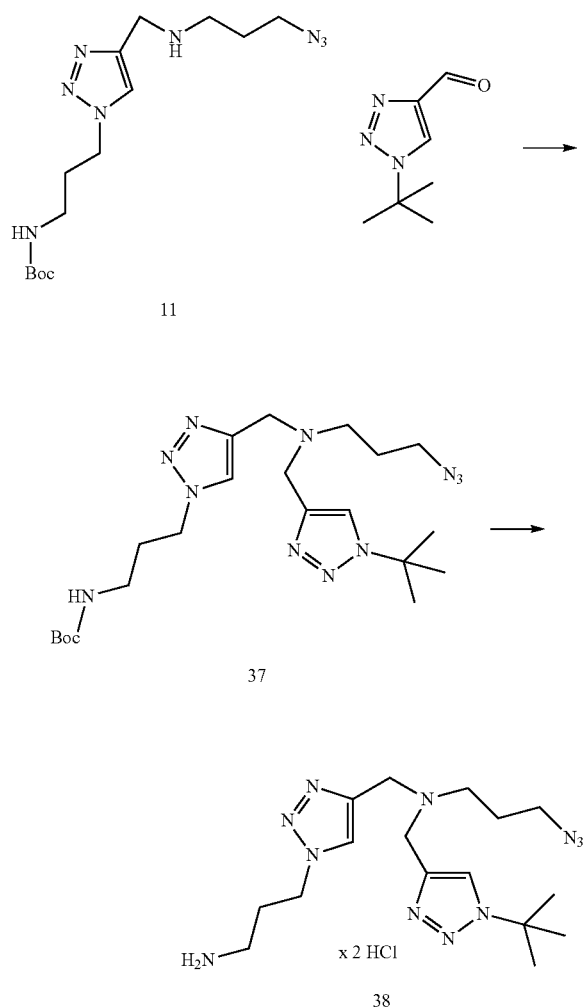

A solution of 11 (0.64 g, 1.89 mmol) was added to a solution of 1-(tert-butyl)-1H-1,2,3-triazole-4-carbaldehyde (0.35 g, 2.27 mmol) in DCM (25 mL) was stirred for one hour at 4° C. Sodium Triacetoxy Borohydride (1.20 g, 5.67 mmol) was added at 4° C. in 4 portions, ice-water bath was removed and the reaction mixture was stirred overnight at room temperature. Aqueous sodium bicarbonate was added dropwise. The reaction mixture was transferred into separatory funnel, the organic layer was separated, and the aqueous layer was extracted with DCM (3×70 mL). Combined organic extracts were dried over anhydrous sodium sulfate and solvents were removed under reduced pressure. The crude 37 was purified by flash chromatography silica gel (DCM/MeOH 100:0 to 90:10).

A solution of 37 in 4 M HCl in Dioxanes was stirred for one hour at room temperature. Upon completion (TLC/HPLC analysis) the solvent was removed under reduced pressure and the crude product was triturated with ether to provide 175 mg of compound 38 as white solid. $^1$H NMR (DMSO-$d_6$, 400 MHz) δ 11.64 (br.s, 1H), 8.54 (s, 1H), 8.52 (s, 1H), 8.35 (br.s, 3H), 4.60 (t, J=7.2 Hz, 2H), 4.50-4.36 (m, 4H), 3.45 (t, J=6.6 Hz, 2H), 3.02 (t, J=7.2 Hz, 2H), 2.85-2.77 (m, 2H), 2.19 (quint, J=7.2 Hz, 2H), 2.10 (quint, J=6.6 Hz, 2H), 1.64 (s, 9H).

Example 22. Compound 39

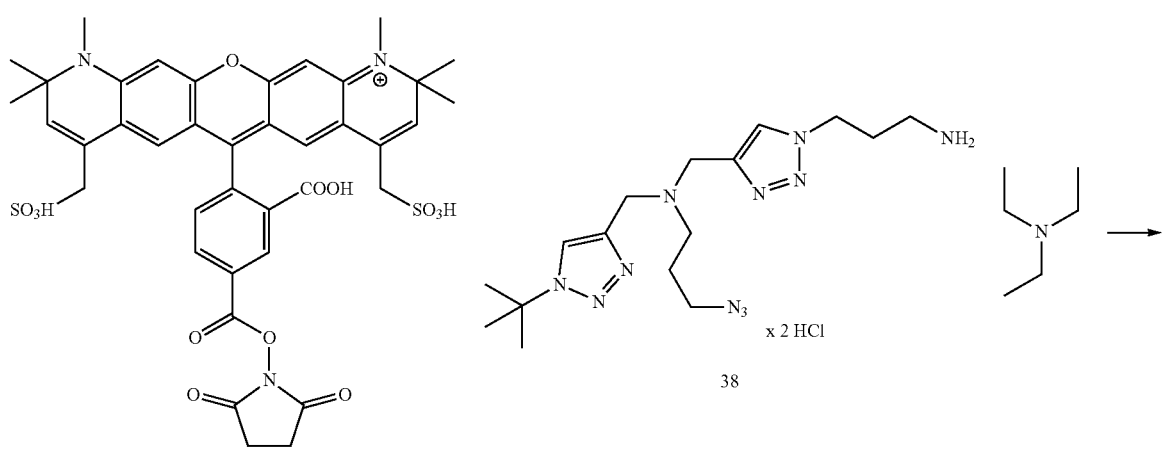

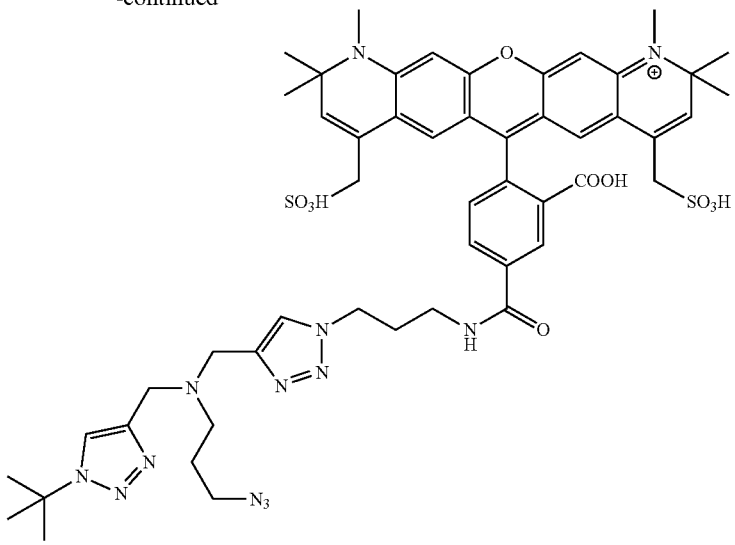

39

A solution of 38 (200 mg) and triethylamine (0.526 mg, 0.751 mL, 5.19 mmol) in DMF (3 mL) was added to a solution of AFDye 594 NHS (Click Chemistry Tools, 0.400 g, 0.487 mmol) in DMF (5 mL). The reaction mixture was stirred for 30 mn at ambient temperature. According to HPLC analysis all AFDye 594 NHS ester was consumed. The reaction mixture was concentrated, and the crude purified in prepHPLC column (C-18, 21.2×250 mm, 35 mL/mL, Water/MeOH 10-75% gradient over 30 min). MS (ESI): MH+=1080.4 (positive mode).

Example 23. Compound 40, 41 and 42

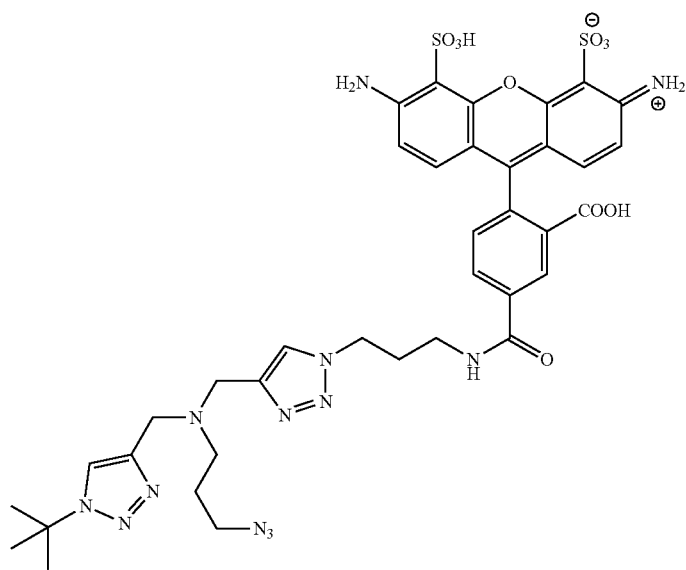

40

-continued
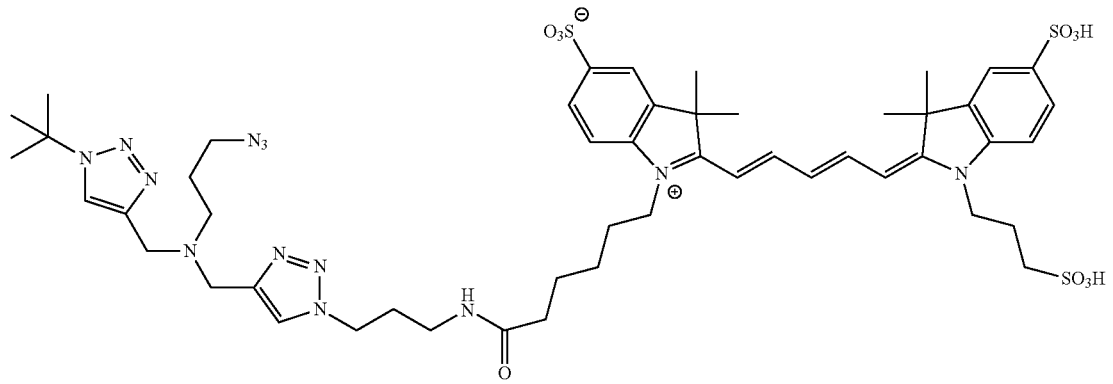
41
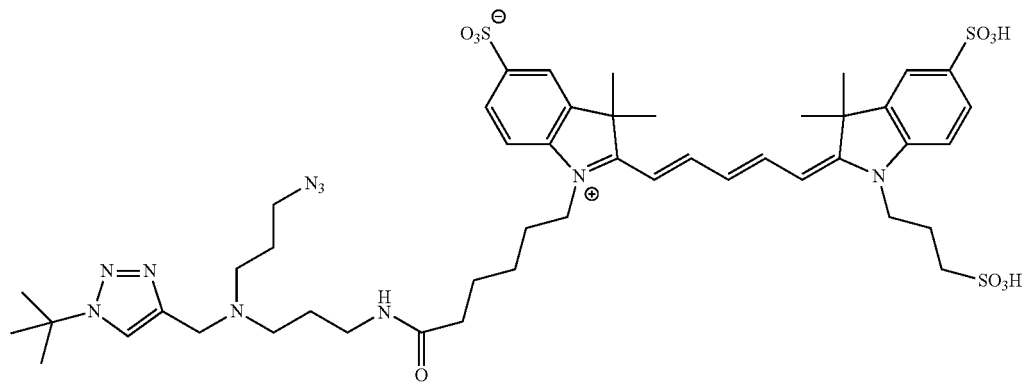
42
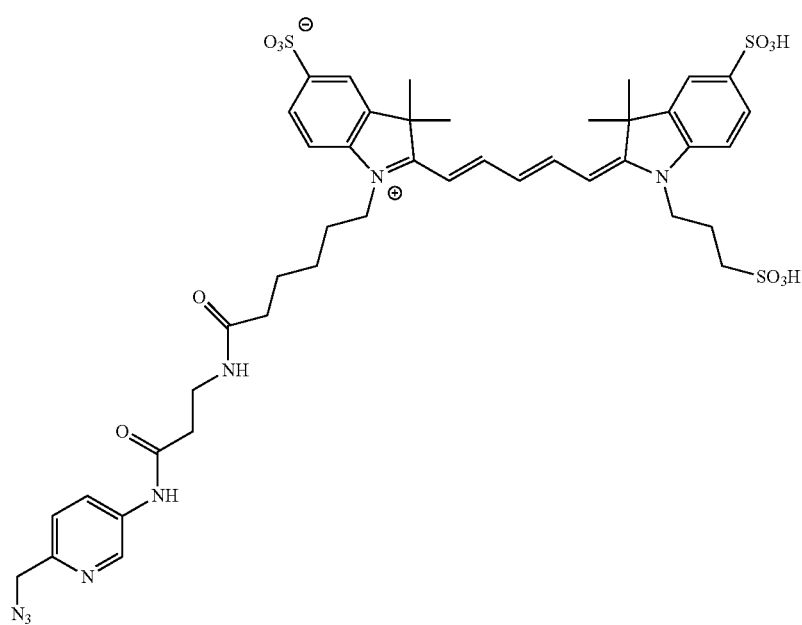
43

Compounds 40, 41 and 42 were prepared according to Examples 22 using corresponding activated ester and compound 38.

Example 24. Kinetics Measurements

A solution of Cy5 Picolyl Azide (43), 30, 41, and 42 (5.4 µM final concentration), copper sulfate (3.125 µM final concentration), THPTA (0 or 6.25 µM final concentration) and sodium ascorbate (118.75 µM) was added to a suspension of Alkyne Agarose (Click Chemistry Tools, 150 µL) in 1.8 mL of BupH buffer, pH 7.5. The concentration of azides in solution was measured by OD 650 after removing the resin.

| | Compound | | | | | | | |
|---|---|---|---|---|---|---|---|---|
| | 30 | 30 | 41 | 41 THPTA | 43 | 43 | 42 | 42 |
| t, min | Yes | No | Yes | No | Yes | No | Yes | No |
| 0 | 0.96 | 0.99 | 0.99 | 1.04 | 1.03 | 1.05 | 1.01 | 0.94 |
| 1 | 0.30 | 0.47 | 0.37 | 0.56 | 0.83 | 0.99 | 0.78 | 0.90 |
| 2 | 0.10 | 0.20 | 0.12 | 0.29 | 0.54 | 0.91 | 0.68 | 0.89 |
| 3 | 0.05 | 0.08 | 0.05 | 0.15 | 0.44 | 0.84 | 0.55 | 0.76 |
| 4 | 0.03 | 0.03 | 0.02 | 0.08 | 0.36 | 0.82 | 0.47 | 1.07 |
| 5 | 0.03 | 0.06 | 0.02 | 0.05 | 0.28 | 0.76 | 0.40 | 0.69 |

Example 25. Cell Lysate Labeling with Compound 36

HEK293T cells were lysed with Lysis Buffer (50 mM Tris-HCl pH 8.0, 1.5 mM MgCl2, 0.3% Triton X-100, 1% SDS, 0.2 mM PMSF, 3000 U Benzonase). After lysis, extracts were cleared by centrifugation and BSA-alkyne was added (75 µg per sample). The click reaction conditions: 50 µM of compound 36, 1 mM copper (II) sulfate, 2 mM THPTA, 5 mM sodium ascorbate. The click reaction was run for 1.5 hours at room temperature, proteins were precipitated with Methanol/Chloroform, dissolved in Resuspension Buffer (50 mM Tris-HCl pH 7.5, 150 mM NaCl, 1% SDS) and incubated for 1.5 h with Streptavidin-agarose. After incubation and excessive washings, proteins were released by heating to 95° C. for 10 min in Release Buffer (2% SDS, 3 mM Biotin, 6M Urea in PBS), dissolved in sample buffer and separated by PAGE. Finally, proteins were stained with Coomassie blue.

Example 26. Visualizing EdU-Labeled DNA

Whole blood from patients was collected in vacutainer tubes containing sodium heparin (BD vacutainer). Peripheral blood mononuclear cells were isolated from whole blood by density gradient centrifugation using Ficoll-Hypaque (Pharmacia). Cells recovered from the interface were washed twice in RPMI (Lonza) and frozen in 10% DMSO. Leukapheresis was performed according to the standard procedures of the American Red Cross. Peripheral blood mononuclear cells (PBMC) were seeded, and the proliferation of T cells was stimulated by incubation with 0.5 µg/ml of anti-CD3 antibodies for 4 days. Cells were treated with 10 uM of EdU for 1.5 hours. harvested, fixed with 3.7% PFA/PBS, and permeabilized with 1% Saponin in PBS. Cells were labeled for 30 min with either compound 30 or 41 at 3 µM, 2 µM, 1.2 µM, 1 µM, or 0.4 µM of fluorophore, 1 mM copper sulfate, 11 mM ascorbic acid. After wash with PBS, stained cells were analyzed on an LSRII or the FACS Aria (BD Biosciences). Data analysis was performed using either Winlist (Verity Software House) or FACSDiva (Becton Dickinson) software.

Example 27. Visualizing OPP-Labeled Proteins

HEK293T cells were treated with 15 µM of OPP for 30 min. After that, they were fixed with 3.7% PFA/PBS, washed with PBS, permeabilized with 0.5% Triton X-100 in PBS and washed again. Then, the cells were labeled for 20 min with either compound 23, 24, 40, 41 and picolyl azide conjugated to Alexa Fluor 488 and Alexa Fluor 594 dyes (4.5 µM), 0.25 mM, 0.5 mM, 1 mM copper sulfate with or without 0.5, 1, or 2 mM THPTA respectively. Concentration of ascorbic acid in all cases was 6 mM. The cells were washed with 0.5 mM EDTA, 2 mM sodium azde in PBS, stained with Hoechst 33342. Negative controls were cell treated treated with DMSO. Images were captured on Leica SP8 White Light Laser Confocal microscope.

Example 28. Immobilization of Compound 15 onto Agarose

A solution of Compound 15 (0.25 g, 0.81 mmon) in DCM (6 mL) was added N-hydroxysuccinimide (0.11 g, 0.93 mmol) and DIC (0.138 g, 1.1 mmol) at r.t., and the reaction mixture was stirred for 30 min at room temperature. According to TLC analysis (DCM:MeOH as 5:1) Compound 15 was completely consumed. The reaction mixture was concentrated and the crude NHS ester of Compound 15 was used without any further purification.

A crude activated ester of Compound 15 was dissolved in 2 mL of DMSO and added to 10 mL of 50% slurry of low density agarose amine in PBS, pH 7.5 buffer. The mixture was agitated overnight at room temperature. The azide activated beads were centrifuged at 1000 g for 5 min, supernatant was discharged, and the beads were washed with water ones and 3 times with 20% EtOH in water.

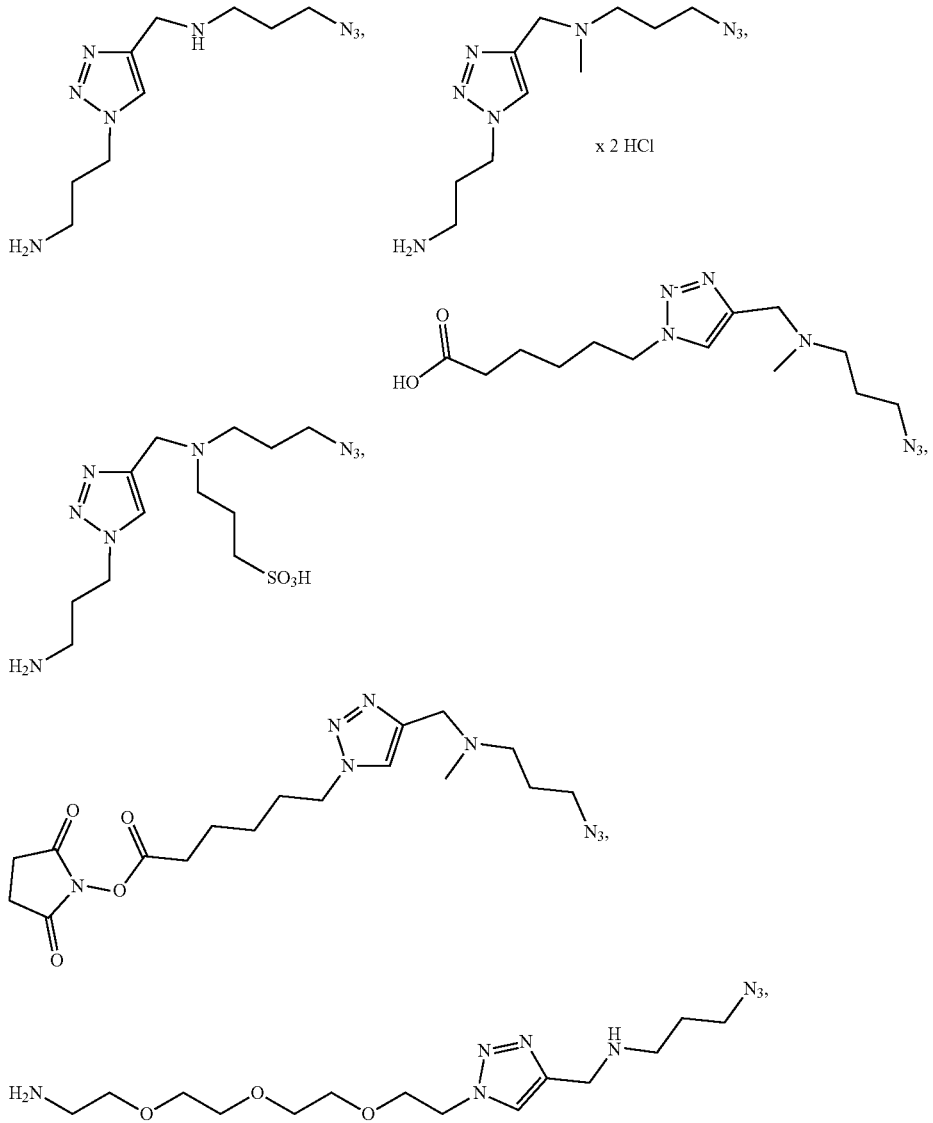

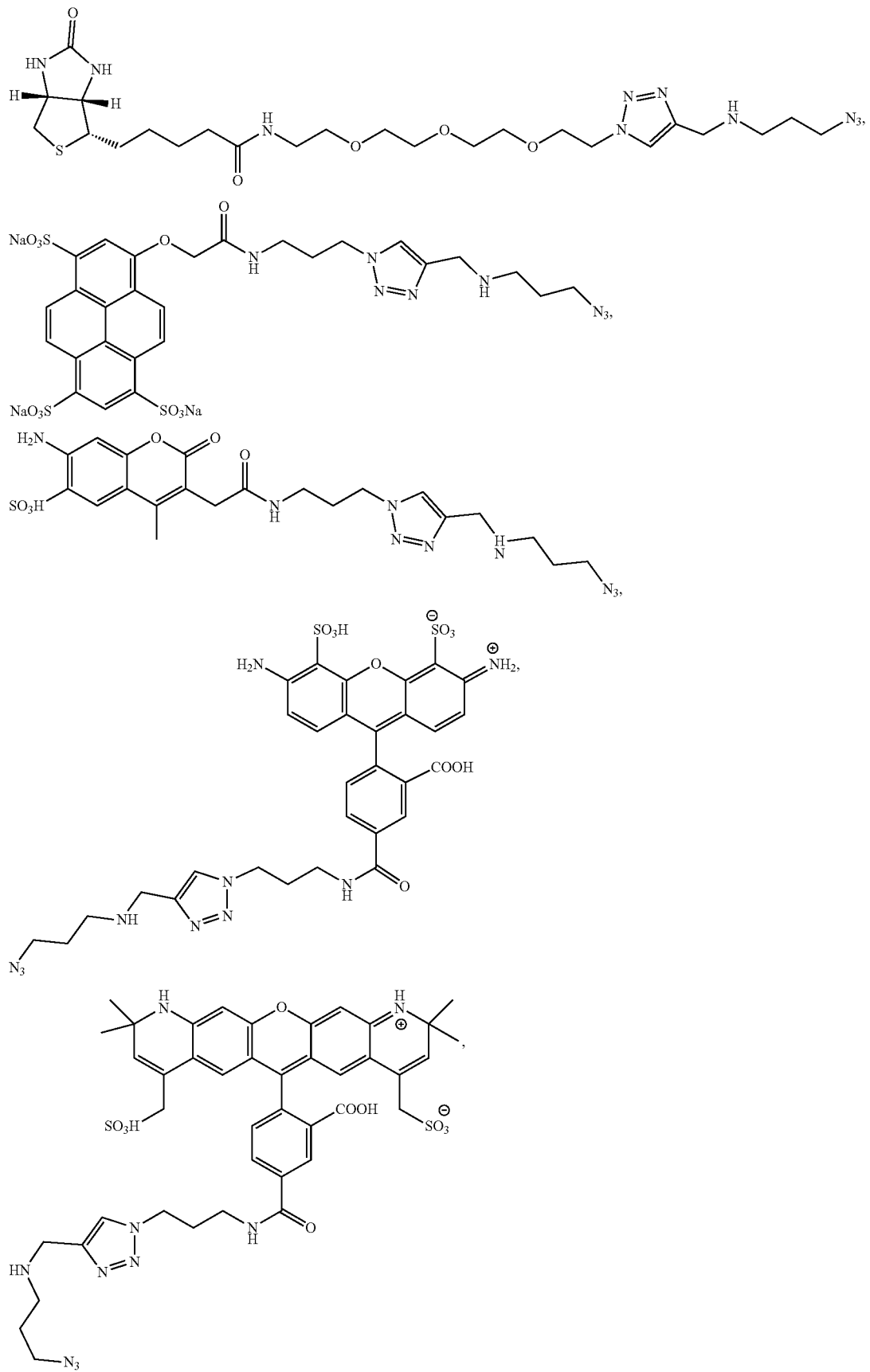

77 78
-continued
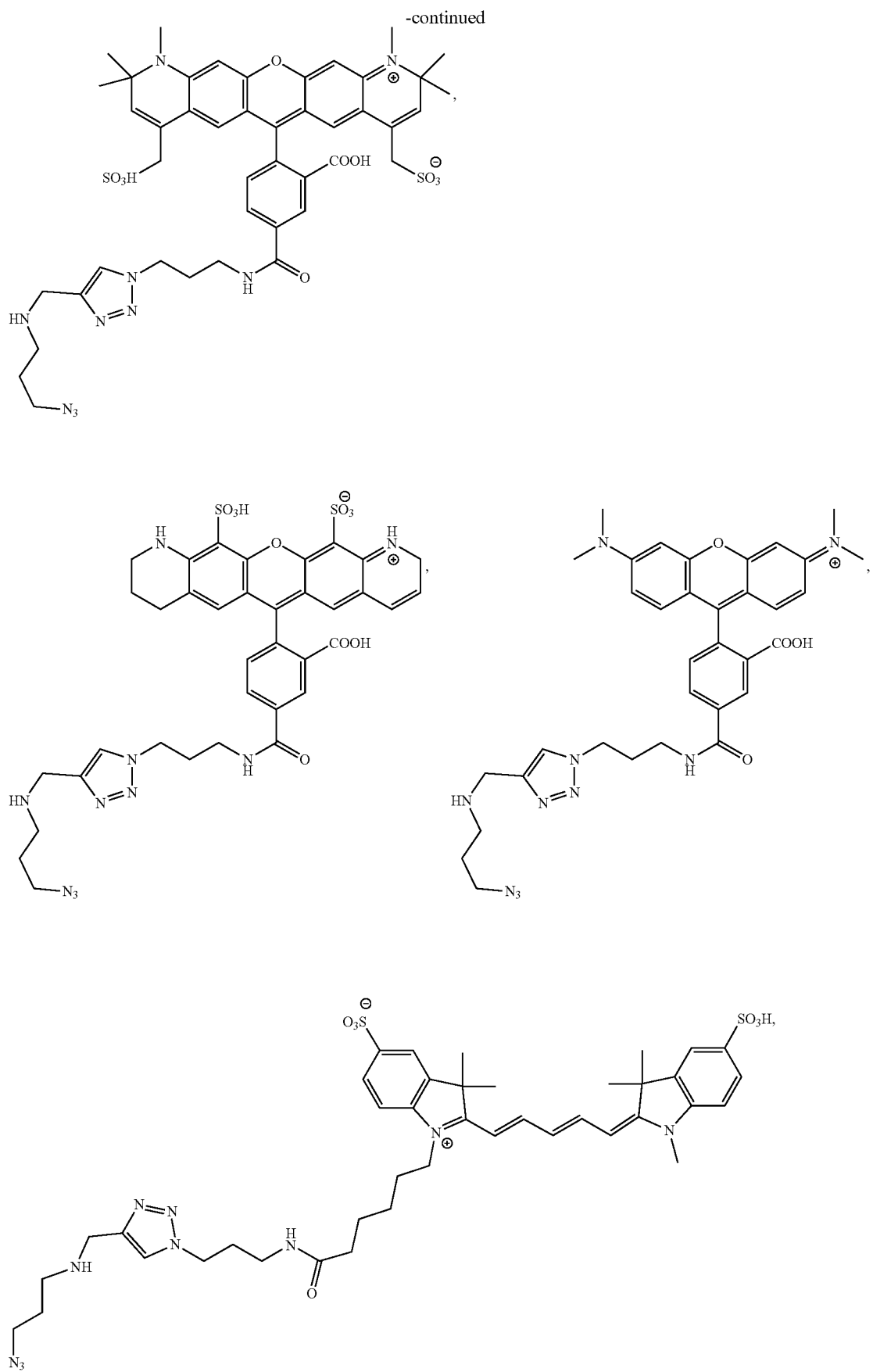

-continued
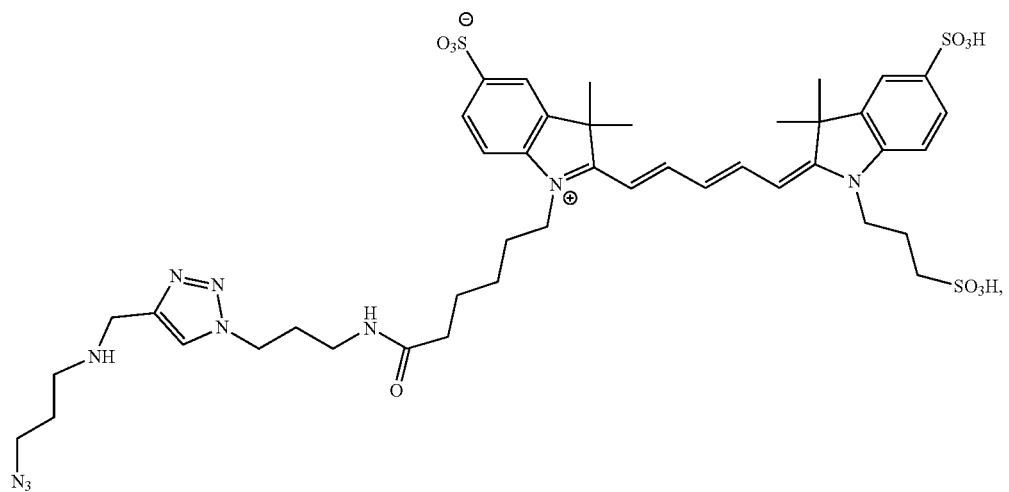
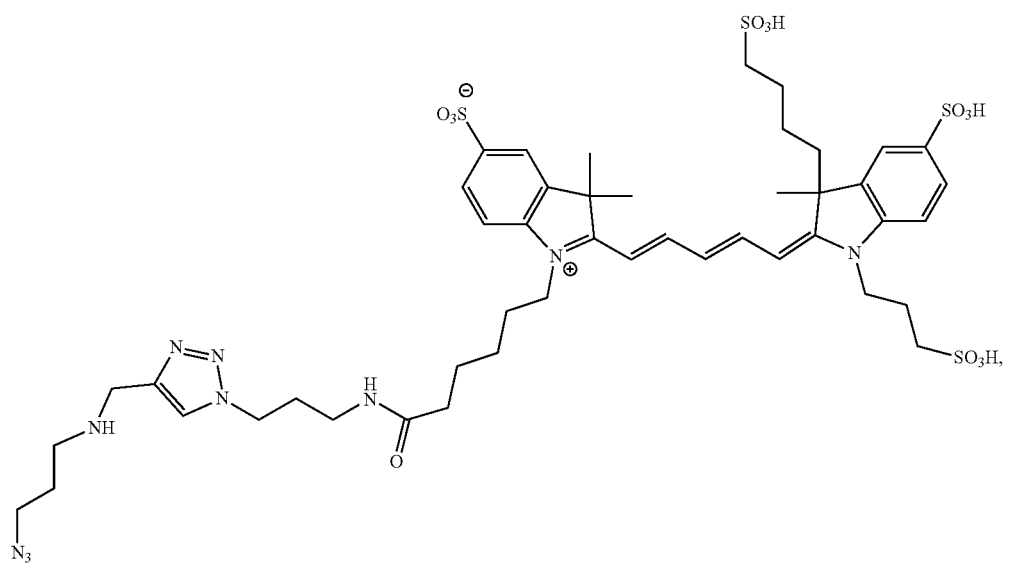
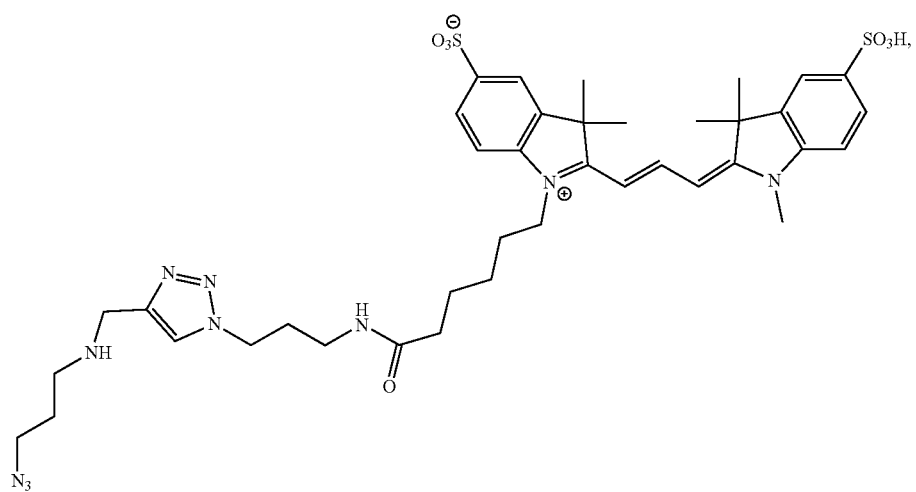

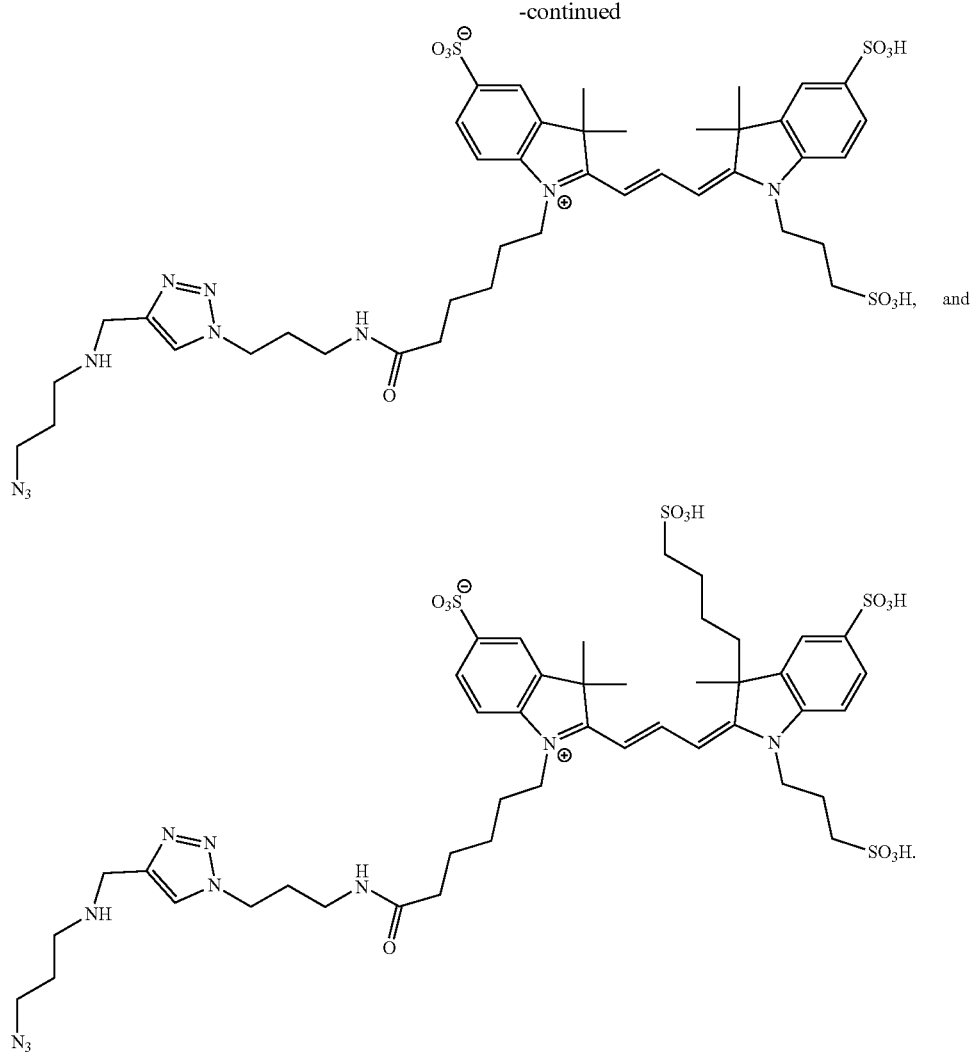

The invention claimed is:
1. A compound of the formula:

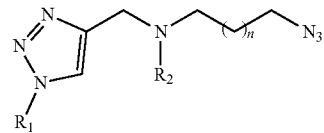

wherein:
n=0, 1, 2, 3 or 4
$R_2$ is a hydrogen, alkyl, or alkyl-$SO_3A$,
where A is H or counterion,
$R_1$ comprises X-L-, wherein:
X is a reporter molecule, a solid support, a carboxylic acid, an activated ester of carboxylic acid, an amine, a hydrazine, a haloacetamide, an alky halide, an isothiocynate, or a maleimide group,
L is a single covalent bond or L is a covalent linkage having 1-24 non-hydrogen atoms selected from C, N, O, P and S and composed of any combinations of single, double, triple or aromatic carbon-carbon bonds, carbon-nitrogen bonds, nitrogen-nitrogen bonds, carbon-oxygen bonds, carbon-sulfur bonds, phosphorus-oxygen bonds and phosphorus-nitrogen bonds in the form of alkyl, heteroalkyl, cycloalkyl, heterocycloalkyl, alkoxy, substituted alkoxy, substituted alkyl, substituted heteroalkyl, substituted cycloalkyl, substituted heterocycloalkyl, aryl, heteroaryl, substituted aryl, arylalkyl, substituted arylalkyl, and substituted heteroaryl.

2. The compound of claim 1 wherein the reporter molecule comprises at least one of a fluorophore, a chromophore, a fluorescent protein, a phosphorescent dye, or a tandem dye.

3. The compound of claim 1 wherein the reporter molecule is xanthene, coumarine, cyanine, pyrene, oxazine, borapolyazaindacene, or carbopyranine.

4. The compound of claim 1 wherein the reporter molecule is a biotin.

5. The compound of claim 1 wherein the solid support is an aerogel, hydrogel, a resin, a silica gel, a bead, a biochip, a microfluidic chip, a silicon ship, a multi-well plate, a membrane, a polymeric membrane, a particle, a derivatized plastic film, a glass bead, a plastic bead, alumina gel, polysaccharide, poly(acrylate), polystyrene, poly(acrylamide), agarose, agar, cellulose, dextrain, starch, heparin, glycogen, amylopectin, nitrocellulose, polyvinylchloride, polypropylene, polyethylene, nylon, latex bead, magnetic bead, paramagnetic bead, superparamagnetic bead, or a magnetic support.

6. A method of modifying a biomolecule comprising the step of reacting a solution of biomolecule comprising an alkyne moiety with a compound of claim 1 to provide a modified biomolecule.

7. The method of claim 6, wherein the solution further comprises copper ions.

8. The method according to claim 6, wherein the method further comprises at least one reducing agent.

9. The method according to claim 6, wherein the method further comprises a copper chelator.

10. A kit comprising a compound of claim 1.

11. The kit of claim 10, wherein the kit comprises a copper ion source.

12. The kit of claim 10 wherein the kit further comprises at least one reducing agent.

13. The kit of claim 10, wherein the kit further comprises a copper chelator.

14. A compound selected from: